(12) United States Patent
Conklin et al.

(10) Patent No.: US 6,329,175 B1
(45) Date of Patent: Dec. 11, 2001

(54) INTERFERON-ε

(75) Inventors: Darrell C. Conklin; Francis J. Grant, both of Seattle; Mark W. Rixon, Issaquah; Wayne Kindsvogel, Seattle, all of WA (US)

(73) Assignee: ZymoGenetics, Inc., Seattle, WA (US)

( * ) Notice: Subject to any disclaimer, the term of this patent is extended or adjusted under 35 U.S.C. 154(b) by 0 days.

(21) Appl. No.: 09/397,992

(22) Filed: Sep. 16, 1999

Related U.S. Application Data

(60) Provisional application No. 60/101,012, filed on Sep. 18, 1998, provisional application No. 60/118,578, filed on Feb. 5, 1999, and provisional application No. 60/142,766, filed on Jul. 8, 1999.

(51) Int. Cl.[7] .............................. C07H 21/04; C12N 5/00; C12N 5/10; C12N 1/20; C12N 1/15
(52) U.S. Cl. ...................... 435/69.51; 536/23.52; 435/325; 435/348; 435/349; 435/410; 435/252.3; 435/254.1; 435/255.1; 435/320.1; 530/351
(58) Field of Search ................... 435/69.51, 325, 435/348, 349, 410, 252.3, 254.1, 253.1, 320.1; 536/23.52; 530/351

(56) References Cited

FOREIGN PATENT DOCUMENTS

WO99/29863   6/1999   (WO).

*Primary Examiner*—Yvonne Eyler
*Assistant Examiner*—Janet L. Andres
(74) *Attorney, Agent, or Firm*—Phillip B. C. Jones

(57) ABSTRACT

Interferons represent an important class of biopharmaceutical products, which have a proven track record in the treatment of a variety of medical conditions, including the treatment of certain autoimmune diseases, the treatment of particular cancers, and the enhancement of the immune response against infectious agents. To date, four types of interferons have been found in humans: interferon-α, interferon-β, interferon-γ, and interferon-ω. The present invention provides new forms of human and murine interferon, "interferon-ε," which have applications in diagnosis and therapy.

22 Claims, 4 Drawing Sheets

```
            10        20        30        40        50        60
zifne-1  MIIKHFFGTVLVLLASTTIFSLDLKLIIFQQRQVNQESLKLLNKLQTLSIQQCLPHRKNF
                  ..  .:: :  ::: :.   :::  ..    ::    ::
1AU1                   MSYNLLGFLQRSSNFQCQKLLWQLNG-RLEYCLKDRMNF
                              10        20         30

70        80        90       100       110       120
zifne-1  LLPQKSLSPQQYQKGHALAILHEMLQQIFSLFRANISLDGWEENHTEKFLIQLHQQLEYL
          .:.  . ::.::  :   .:::::::::::. :  .:::  .:::.  . ..:::::::
1AU1     DIPEEIKQLQQFQKEDAALTIYEMLQNIFAIFRQDSSSTGWNETIVENLLANVYHQINHL
            40        50        60        70        80        90

130       140       150       160       170       180
zifne-1  EALMGLEAEKLSGTLGSDNLRLQVKMYFRRIHDYLENQDYSTCAWAIVQVEISRCLFFVF
         ....  :: . : .    :...: .. :: ...  ....  ::::::::.::  ....
1AU1     KTVLEEKLEKEDFTRGKLMSSLHLKRYYGRILHYLKAKEYSHCAWTIVRVEILRNFYFIN
            100       110       120       130       140       150

190       200
zifne-1  SLTEKLSKQGRPLNDMKQELTTEFRSPR
              ::
1AU1     RLTGYLRN
            160
```

FIG. 1

SEQUENCE LISTING

<160> NUMBER OF SEQ ID NOS: 33

<210> SEQ ID NO 1
<211> LENGTH: 1234
<212> TYPE: DNA
<213> ORGANISM: Homo sapiens
<220> FEATURE:
<221> NAME/KEY: CDS
<222> LOCATION: (454)...(1077)

<400> SEQUENCE: 1

```
aggtgctgat aagcctttgg taagttttac tccatgaaag actattactg aaaaaaacgt     60
aatctcaata aaagaacttt aataagcttg actaaatatt tagaaagcac attgtgttca    120
gtgaaacttt gtatataatg aatagaataa taaagatta tgttggatga ctagtctgta    180
attgcctcaa ggaaagcata caatgaataa gttattttgg tacttcctca aaatagccaa    240
cacaataggg aaatggagaa aatgtactct gaacaccatg aaaagggaac ctgaaaatct    300
aatgtgtaaa cttggagaaa tgacattaga aaacgaaagc aacaaaagag aacactctcc    360
aaaataatct gagatgcatg aaaggcaaac attcactaga gctggaattt ccctaagtct    420
atgcagggat aagtagcata tttgaccttc acc atg att atc aag cac ttc ttt     474
                                   Met Ile Ile Lys His Phe Phe
                                    1               5 gga act gtg ttg gtg ctg ctg gcc tct acc act atc ttc tct cta gat     522
Gly Thr Val Leu Val Leu Leu Ala Ser Thr Thr Ile Phe Ser Leu Asp
            10                  15                  20 ttg aaa ctg att atc ttc cag caa aga caa gtg aat caa gaa agt tta     570
Leu Lys Leu Ile Ile Phe Gln Gln Arg Gln Val Asn Gln Glu Ser Leu
        25                  30                  35 aaa ctc ttg aat aag ttg caa acc ttg tca att cag cag tgt cta cca     618
Lys Leu Leu Asn Lys Leu Gln Thr Leu Ser Ile Gln Gln Cys Leu Pro
40                  45                  50                  55 cac agg aaa aac ttt ctg ctt cct cag aag tct ttg agt cct cag cag     666
His Arg Lys Asn Phe Leu Leu Pro Gln Lys Ser Leu Ser Pro Gln Gln
                60                  65                  70 tac caa aaa gga cac act ctg gcc att ctc cat gag atg ctt cag cag     714
Tyr Gln Lys Gly His Thr Leu Ala Ile Leu His Glu Met Leu Gln Gln
            75                  80                  85 atc ttc agc ctc ttc agg gca aat att tct ctg gat ggt tgg gag gaa     762
Ile Phe Ser Leu Phe Arg Ala Asn Ile Ser Leu Asp Gly Trp Glu Glu
        90                  95                 100 aac cac acg gag aaa ttc ctc att caa ctt cat caa cag cta gaa tac     810
Asn His Thr Glu Lys Phe Leu Ile Gln Leu His Gln Gln Leu Glu Tyr
    105                 110                 115 cta gaa gca ctc atg gga ctg gaa gca gag aag cta agt ggt act ttg     858
Leu Glu Ala Leu Met Gly Leu Glu Ala Glu Lys Leu Ser Gly Thr Leu
120                 125                 130                 135 ggt agt gat aac ctt aga tta caa gtt aaa atg tac ttc cga agg atc     906
Gly Ser Asp Asn Leu Arg Leu Gln Val Lys Met Tyr Phe Arg Arg Ile
                140                 145                 150 cat gat tac ctg gaa aac cag gac tac agc acc tgt gcc tgg gcc att     954
His Asp Tyr Leu Glu Asn Gln Asp Tyr Ser Thr Cys Ala Trp Ala Ile
            155                 160                 165 gtc caa gta gaa atc agc cga tgt ctg ttc ttt gtg ttc agt ctc aca    1002
Val Gln Val Glu Ile Ser Arg Cys Leu Phe Phe Val Phe Ser Leu Thr
        170                 175                 180 gaa aaa ctg agc aaa caa gga aga ccc ttg aac gac atg aag caa gag    1050
Glu Lys Leu Ser Lys Gln Gly Arg Pro Leu Asn Asp Met Lys Gln Glu
```

```
            185                 190                 195
ctt act aca gag ttt aga agc ccg agg taggtggagg gactagagga        1097
Leu Thr Thr Glu Phe Arg Ser Pro Arg
200                 205 cttctccaga catgattctt catagagtgg taatacaatt tatagtacaa tcacattgct  1157
ttgattttgt gtatatatat atttatctgt gttttaagat tgtgcatatt gaccacaatt  1217 gttttttacct gcccggg                                                1234

<210> SEQ ID NO 2
<211> LENGTH: 208
<212> TYPE: PRT
<213> ORGANISM: Homo sapiens

<400> SEQUENCE: 2

Met Ile Ile Lys His Phe Phe Gly Thr Val Leu Val Leu Leu Ala Ser
 1               5                  10                  15

Thr Thr Ile Phe Ser Leu Asp Leu Lys Leu Ile Ile Phe Gln Gln Arg
             20                  25                  30

Gln Val Asn Gln Glu Ser Leu Lys Leu Leu Asn Lys Leu Gln Thr Leu
         35                  40                  45

Ser Ile Gln Gln Cys Leu Pro His Arg Lys Asn Phe Leu Leu Pro Gln
 50                  55                  60

Lys Ser Leu Ser Pro Gln Gln Tyr Gln Lys Gly His Thr Leu Ala Ile
 65                  70                  75                  80

Leu His Glu Met Leu Gln Gln Ile Phe Ser Leu Phe Arg Ala Asn Ile
             85                  90                  95

Ser Leu Asp Gly Trp Glu Glu Asn His Thr Glu Lys Phe Leu Ile Gln
            100                 105                 110

Leu His Gln Gln Leu Glu Tyr Leu Glu Ala Leu Met Gly Leu Glu Ala
        115                 120                 125

Glu Lys Leu Ser Gly Thr Leu Gly Ser Asp Asn Leu Arg Leu Gln Val
130                 135                 140

Lys Met Tyr Phe Arg Arg Ile His Asp Tyr Leu Glu Asn Gln Asp Tyr
145                 150                 155                 160

Ser Thr Cys Ala Trp Ala Ile Val Gln Val Glu Ile Ser Arg Cys Leu
                165                 170                 175

Phe Phe Val Phe Ser Leu Thr Glu Lys Leu Ser Lys Gln Gly Arg Pro
            180                 185                 190

Leu Asn Asp Met Lys Gln Glu Leu Thr Thr Glu Phe Arg Ser Pro Arg
        195                 200                 205

<210> SEQ ID NO 3
<211> LENGTH: 624
<212> TYPE: DNA
<213> ORGANISM: Artificial Sequence
<220> FEATURE:
<223> OTHER INFORMATION: This degenerate sequence encodes the amino acid
      sequence of SEQ ID NO:2.
<221> NAME/KEY: variation
<222> LOCATION: (1)...(624)
<223> OTHER INFORMATION: n is any nucleotide

<400> SEQUENCE: 3
atgathatha arcayttytt yggnacngtn ytngtnytny tngcnwsnac nacnathtty    60
wsnytngayy tnaarytnat hathttycar carmgncarg tnaaycarga rwsnytnaar  120
ytnytnaaya arytncarac nytnwsnath carcartgyy tnccncaymg naaraaytty  180
```

```
ytnytnccnc araarwsnyt nwsnccncar cartaycara arggncayac nytngcnath      240
ytncaygara tgytncarca rathttywsn ytnttymgng cnaayathws nytngayggn      300
tgggargara aycayacnga raarttyytn athcarytnc aycarcaryt ngartayytn      360
gargcnytna tgggnytnga rgcngaraar ytnwsnggna cnytnggnws ngayaayytn      420
mgnytncarg tnaaratgta yttym

```
            140                 145                 150
cat gat tac ctg gaa aac cag gac tac agc acc tgt gcc tgg gcc att    954
His Asp Tyr Leu Glu Asn Gln Asp Tyr Ser Thr Cys Ala Trp Ala Ile
            155                 160                 165 gtc caa gta gaa atc agc cga tgt ctg ttc ttt gtg ttc agt ctc aca   1002
Val Gln Val Glu Ile Ser Arg Cys Leu Phe Phe Val Phe Ser Leu Thr
            170                 175                 180 gaa aaa ctg agc aaa caa gga aga ccc ttg aac gac atg aag caa gag   1050
Glu Lys Leu Ser Lys Gln Gly Arg Pro Leu Asn Asp Met Lys Gln Glu
            185                 190                 195 ctt act aca gag ttt aga agc ccg agg taggtggagg gactagagga         1097
Leu Thr Thr Glu Phe Arg Ser Pro Arg
200                 205 cttctccaga catgattctt catagagtgg taatacaatt tatagtacaa tcacattgct  1157
ttgattttgt gtatatatat atttatctgt gttttaagat tgtgcatatt gaccacaatt  1217
gtttttacct gcccggg                                                 1234

<210> SEQ ID NO 5
<211> LENGTH: 208
<212> TYPE: PRT
<213> ORGANISM: Homo sapiens

<400> SEQUENCE: 5

Met Ile Ile Lys His Phe Phe Gly Thr Val Leu Val Leu Leu Ala Ser
1               5                   10                  15

Thr Thr Ile Phe Ser Leu Asp Leu Lys Leu Ile Ile Phe Gln Gln Arg
            20                  25                  30

Gln Val Asn Gln Glu Ser Leu Lys Leu Leu Asn Lys Leu Gln Thr Leu
        35                  40                  45

Ser Ile Gln Gln Cys Leu Pro His Arg Lys Asn Phe Leu Leu Pro Gln
    50                  55                  60

Lys Ser Leu Ser Pro Gln Gln Tyr Gln Lys Gly His Ala Leu Ala Ile
65                  70                  75                  80

Leu His Glu Met Leu Gln Gln Ile Phe Ser Leu Phe Arg Ala Asn Ile
                85                  90                  95

Ser Leu Asp Gly Trp Glu Glu Asn His Thr Glu Lys Phe Leu Ile Gln
            100                 105                 110

Leu His Gln Gln Leu Glu Tyr Leu Glu Ala Leu Met Gly Leu Glu Ala
        115                 120                 125

Glu Lys Leu Ser Gly Thr Leu Gly Ser Asp Asn Leu Arg Leu Gln Val
    130                 135                 140

Lys Met Tyr Phe Arg Arg Ile His Asp Tyr Leu Glu Asn Gln Asp Tyr
145                 150                 155                 160

Ser Thr Cys Ala Trp Ala Ile Val Gln Val Glu Ile Ser Arg Cys Leu
                165                 170                 175

Phe Phe Val Phe Ser Leu Thr Glu Lys Leu Ser Lys Gln Gly Arg Pro
            180                 185                 190

Leu Asn Asp Met Lys Gln Glu Leu Thr Thr Glu Phe Arg Ser Pro Arg
        195                 200                 205

<210> SEQ ID NO 6
<211> LENGTH: 624
<212> TYPE: DNA
<213> ORGANISM: Artificial Sequence
<220> FEATURE:
<223> OTHER INFORMATION: This degenerate sequence encodes the amino acid
      sequence of SEQ ID NO:5.
```

<210> SEQ ID NO 7
<211> LENGTH: 166
<212> TYPE: PRT
<213> ORGANISM: Homo sapiens
<221> NAME/KEY: variation
<222> LOCATION: (1)...(624)
<223> OTHER INFORMATION: n is any nucleotide

<400> SEQUENCE: 6

```
atgathatha arcayttytt yggnacngtn ytngtnytny tngcnwsnac nacnathtty      60
wsnytngayy tnaarytnat hathttycar carmgncarg tnaaycarga rwsnytnaar    120
ytnytnaaya arytncarac nytnwsnath

```
ctctgcttcc agtcccatga g                                              21

<210> SEQ ID NO 9
<211> LENGTH: 21
<212> TYPE: DNA
<213> ORGANISM: Artificial Sequence
<220> FEATURE:
<223> OTHER INFORMATION: PCR primer

<400> SEQUENCE: 9
ggacacactc tggccattct c                                              21

<210> SEQ ID NO 10
<211> LENGTH: 20
<212> TYPE: DNA
<213> ORGANISM: Artificial Sequence
<220> FEATURE:
<223> OTHER INFORMATION: PCR primer

<400> SEQUENCE: 10
aaactttctg cttcctcaga                                                20

<210> SEQ ID NO 11
<211> LENGTH: 20
<212> TYPE: DNA
<213> ORGANISM: Artificial Sequence
<220> FEATURE:
<223> OTHER INFORMATION: PCR primer

<400> SEQUENCE: 11
cccaaagtac cacttagctt                                                20

<210> SEQ ID NO 12
<211> LENGTH: 26
<212> TYPE: DNA
<213> ORGANISM: Artificial Sequence
<220> FEATURE:
<223> OTHER INFORMATION: PCR primer

<400> SEQUENCE: 12
tctagctgtt gatgaagttg aatgag                                         26

<210> SEQ ID NO 13
<211> LENGTH: 27
<212> TYPE: DNA
<213> ORGANISM: Artificial Sequence
<220> FEATURE:
<223> OTHER INFORMATION: PCR primer

<400> SEQUENCE: 13
ccatcctaat acgactcact atagggc                                        27

<210> SEQ ID NO 14
<211> LENGTH: 23
<212> TYPE: DNA
<213> ORGANISM: Artificial Sequence
<220> FEATURE:
<223> OTHER INFORMATION: PCR primer

<400> SEQUENCE: 14
actcactata gggctcgagc ggc                                            23

<210> SEQ ID NO 15
<211> LENGTH: 23
<212> TYPE: DNA
<213> ORGANISM: Artificial Sequence
```

```
<220> FEATURE:
<223> OTHER INFORMATION: PCR primer

<400> SEQUENCE: 15
agggcaaata tttctctgga tgg                                               23

<210> SEQ ID NO 16
<211> LENGTH: 24
<212> TYPE: DNA
<213> ORGANISM: Artificial Sequence
<220> FEATURE:
<223> OTHER INFORMATION: PCR primer

<400> SEQUENCE: 16
agggataagt agcatatttg acct                                              24

<210> SEQ ID NO 17
<211> LENGTH: 30
<212> TYPE: DNA
<213> ORGANISM: Artificial Sequence
<220> FEATURE:
<223> OTHER INFORMATION: PCR primer

<400> SEQUENCE: 17
tgtactataa attgtattac cactctatga                                        30

<210> SEQ ID NO 18
<211> LENGTH: 18
<212> TYPE: DNA
<213> ORGANISM: Artificial Sequence
<220> FEATURE:
<223> OTHER INFORMATION: PCR primer

<400> SEQUENCE: 18
agccgatgtc tgttctttt                                                    18

<210> SEQ ID NO 19
<211> LENGTH: 18
<212> TYPE: DNA
<213> ORGANISM: Artificial Sequence
<220> FEATURE:
<223> OTHER INFORMATION: PCR primer

<400> SEQUENCE: 19
cctcgggctt ctaaactc                                                     18

<210> SEQ ID NO 20
<211> LENGTH: 16
<212> TYPE: PRT
<213> ORGANISM: Artificial Sequence
<220> FEATURE:
<223> OTHER INFORMATION: Peptide linker

<400> SEQUENCE: 20

Gly Gly Ser Gly Gly Ser Gly Gly Gly Ser Gly Gly Gly Gly Ser
1               5                   10                  15

<210> SEQ ID NO 21
<211> LENGTH: 20
<212> TYPE: DNA
<213> ORGANISM: Artificial Sequence
<220> FEATURE:
<223> OTHER INFORMATION: PCR primer

<400> SEQUENCE: 21
gcctctacca ctatcttctc                                                   20
```

<210> SEQ ID NO 22
<211> LENGTH: 20
<212> TYPE: DNA
<213> ORGANISM: Artificial Sequence
<220> FEATURE:
<223> OTHER INFORMATION: PCR primer

<400> SEQUENCE: 22
ggtcttcctt gtttgctcag                                           20

<210> SEQ ID NO 23
<211> LENGTH: 2313
<212> TYPE: DNA
<213> ORGANISM: Mouse
<220> FEATURE:
<221> NAME/KEY: CDS
<222> LOCATION: (779)...(1354)

<400> SEQUENCE: 23

```
ttctcacaat cttgttatct ttaactggtt tcatgtattc atagaggacc aaacacatttg    60 tagccattgt actgaacttg taggttgtgc atactatgct gctatcatga ggctataatc    120
acaatctttt gataagtttt acttttatct tattttgtaa gctaaaatat tagatattaa    180
actgattggg tgaaatataa aatagttcaa ggttattggt acatattttc acattaatat    240
gcccaaatac ttgtgcacat ttacagttgt acatgaagtt tcaaagttat cagcctgtgg    300
atttcaatgt ttacctcaga gtgtgctctg gccactacca gatctataat aaataatact    360
ccatgaaata ccactgcttg aaaaggaag cttgctctca ataaagtgc attactaagc     420 ctgagtaagc atttagaaag tgcattgtgt tagttaaggc ttgtacgtaa taaataatga    480
gtggtaatag taggtcagag tggacaacta tcattgtctc aagacaagtg cacagtgaag    540
ccagctcttt cgttacttcc tcaaacagca acacaatggg gaatgtaaag gaatgttcc    600 ataaaaccct ggaatgggaa ccagaaaacc taaggtataa acttgggaaa cgacgtacaa    660
ggaaacacag acaacagaaa agaacaccct ccctcagggt ttcagatgcg tgagaggtaa    720
atatttccca gaactggagt ggtacaaggt gtgcagagat ccctgtgtgc cctccacc     778
```

| atg gtt cac aga cag ctc cct gaa acg gtg ttg ctg ctc ttg gtt tct | 826 |
|---|---|
| Met Val His Arg Gln Leu Pro Glu Thr Val Leu Leu Leu Leu Val Ser | |
| 1               5                  10                  15       | |

| tcc act atc ttc tcc cta gaa ccg aaa cgg att ccc ttc caa ttg tgg | 874 |
|---|---|
| Ser Thr Ile Phe Ser Leu Glu Pro Lys Arg Ile Pro Phe Gln Leu Trp | |
|         20                 25                  30               | |

| atg aac aga gaa agc cta caa cta ctg aaa cct ttg cca agc tcg tca | 922 |
|---|---|
| Met Asn Arg Glu Ser Leu Gln Leu Leu Lys Pro Leu Pro Ser Ser Ser | |
|     35                  40                  45                  | |

| gtc cag cag tgt cta gca cac agg aag aat ttc ctg ctt cct cag cag | 970 |
|---|---|
| Val Gln Gln Cys Leu Ala His Arg Lys Asn Phe Leu Leu Pro Gln Gln | |
| 50                  55                  60                      | |

| cct gtg agt cct cac cag tac caa gag gga cag gtg ctg gct gtt gtg | 1018 |
|---|---|
| Pro Val Ser Pro His Gln Tyr Gln Glu Gly Gln Val Leu Ala Val Val | |
| 65                  70                  75                  80  | |

| cac gag atc ctt cag cag atc ttc acg ctc ctc cag aca cat ggg act | 1066 |
|---|---|
| His Glu Ile Leu Gln Gln Ile Phe Thr Leu Leu Gln Thr His Gly Thr | |
|             85                  90                  95          | |

| atg ggc att tgg gag gaa aac cat ata gaa aaa gtc tta gct gcg ctt | 1114 |
|---|---|
| Met Gly Ile Trp Glu Glu Asn His Ile Glu Lys Val Leu Ala Ala Leu | |
|                 100                 105                 110     | |

| cac cgg cag ctg gaa tac gtg gag tca ctg ggt gga ctg aac gca gcg | 1162 |

-continued

```
His Arg Gln Leu Glu Tyr Val Glu Ser Leu Gly Gly Leu Asn Ala Ala
            115                 120                 125 cag aag agt ggg ggc tcg agt gcg cag aac ctt agg tta cag att aaa      1210
Gln Lys Ser Gly Gly Ser Ser Ala Gln Asn Leu Arg Leu Gln Ile Lys
        130                 135                 140 gca tac ttc agg agg atc cac gat tac ttg gaa aac caa agg tac agc      1258
Ala Tyr Phe Arg Arg Ile His Asp Tyr Leu Glu Asn Gln Arg Tyr Ser
145                 150                 155                 160 agc tgt gcc tgg atc att gtc cag aca gaa atc cac cgc tgt atg ttc      1306
Ser Cys Ala Trp Ile Ile Val Gln Thr Glu Ile His Arg Cys Met Phe
                165                 170                 175 ttt gtg ttc agg ttc aca aca tgg ctg agc aga caa gac cca gac cct      1354
Phe Val Phe Arg Phe Thr Thr Trp Leu Ser Arg Gln Asp Pro Asp Pro
            180                 185                 190 tgaacactga gaagcaagag ccaacagggg atttgaaaga cataggttgg tggcggagtg    1414
ggaggagcta tatgaacatg atttgtttct ttttggtgta agtggctgc attgttttgc     1474
ttctgcccag gtttaactgt gttctaagat ggcatgcatt gcaatatcca ttttgccatg    1534
ccatgttatg ttttctacca acttcaaatt atttaggaat taaaattaat tcattaaaat    1594
ttcataattg gttcttcagt ggtgaaattt cgtagaattt tgccgttaga tacgatgagc    1654
tatctcgata atgtagtgag cattccttaa catacagcat taattcatgt ttaccagaac    1714
ttgttagcat caatccatga atatttctat tacaaagaca aatagaaat acggccaaaa     1774
ggtgtgaaca attttcagaa gaatgaaaac agattcaatc tcactcatta taataataat   1834
aatgcagatt acaactgaat agcatgctgt ttttaaccta ttaactaaca cctcaaggtt    1894
taattaagaa aaaatatgca gactcaacac atttctgaga aagcaggaac ttttcctgtg    1954
tgctagactc tgtcgggtga ttagttaatg aatgctctta caatttgcta gatcagcaga    2014
agttagtgta agcaacttca cctaagagaa caagattctc ttgacgagaa cgtgatgttt    2074
tctctacaaa agtacataga gaaaaataaa agcaaaaaaa aagtaaaacg tgtataagta    2134
gtatatttgt gtaaaaccat gaagtaatct taatatttgt actgactaca tgtgaagaac    2194
taaagaacac acgagaaata aatggtaagg attaattatt ggtctgtgga ggccgacttg    2254
agggatgggg ggcaggaaga agagggaagg agagcctttg ctcttgtttc tgtggtagc     2313
```

<210> SEQ ID NO 24
<211> LENGTH: 192
<212> TYPE: PRT
<213> ORGANISM: Mouse

<400> SEQUENCE: 24

```
Met Val His Arg Gln Leu Pro Glu Thr Val Leu Leu Leu Leu Val Ser
  1               5                  10                  15

Ser Thr Ile Phe Ser Leu Glu Pro Lys Arg Ile Pro Phe Gln Leu Trp
                 20                  25                  30

Met Asn Arg Glu Ser Leu Gln Leu Leu Lys Pro Leu Pro Ser Ser Ser
            35                  40                  45

Val Gln Gln Cys Leu Ala His Arg Lys Asn Phe Leu Pro Gln Gln
         50                  55                  60

Pro Val Ser Pro His Gln Tyr Gln Glu Gly Gln Val Leu Ala Val Val
 65                  70                  75                  80

His Glu Ile Leu Gln Gln Ile Phe Thr Leu Leu Gln Thr His Gly Thr
                     85                  90                  95

Met Gly Ile Trp Glu Glu Asn His Ile Glu Lys Val Leu Ala Ala Leu
                100                 105                 110
```

His Arg Gln Leu Glu Tyr Val Glu Ser Leu Gly Leu Asn Ala Ala
        115                 120                 125

Gln Lys Ser Gly Gly Ser Ser Ala Gln Asn Leu Arg Leu Gln Ile Lys
    130                 135                 140

Ala Tyr Phe Arg Arg Ile His Asp Tyr Leu Glu Asn Gln Arg Tyr Ser
145                 150                 155                 160

Ser Cys Ala Trp Ile Ile Val Gln Thr Glu Ile His Arg Cys Met Phe
                165                 170                 175

Phe Val Phe Arg Phe Thr Thr Trp Leu Ser Arg Gln Asp Pro Asp Pro
                180                 185                 190

<210> SEQ ID NO 25
<211> LENGTH: 576
<212> TYPE: DNA
<213> ORGANISM: Artificial Sequence
<220> FEATURE:
<223> OTHER INFORMATION: This degenerate sequence encodes the amino acid
      sequence of SEQ ID NO:24.
<221> NAME/KEY: variation
<222> LOCATION: (1)...(576)
<223> OTHER INFORMATION: N is any nucleotide.

<400> SEQUENCE: 25
atggtncaym gncarytncc ngaracngtn ytnytnytny tngtnwsnws nacnathtty      60
wsnytngarc cnaarmgnat hccnttycar ytntggatga aymgngarws nytncarytn     120
ytnaarccny tnccnwsnws nwsngtncar cartgyytng cncaymgnaa raayttyytn     180
ytnccncarc arccngtnws nccncaycar taycargarg gncargtnyt ngcngtngtn     240
caygarathy tncarcarat httyacnytn ytncaracnc ayggnacnat gggnathtgg     300
gargaraayc ayathgaraa rgtnytngcn gcnytncaym gncarytnga rtaygtngar     360
wsnytnggng gnytnaaygc ngcncaraar wsnggnggnw snwsngcnca raayytnmgn     420
ytncaratha argcntaytt ymgnmgnath caygaytayy tngaraayca rmgntaywsn     480
wsntgygcnt ggathathgt ncaracngar athcaymgnt gyatgttytt ygtnttymgn     540
ttyacnacnt ggytnwsnmg ncargayccn gayccn                              576

<210> SEQ ID NO 26
<211> LENGTH: 193
<212> TYPE: PRT
<213> ORGANISM: Artificial Sequence
<220> FEATURE:
<223> OTHER INFORMATION: Truncated interferon-epsilon.

<400> SEQUENCE: 26

Met Ile Ile Lys His Phe Phe Gly Thr Val Leu Val Leu Leu Ala Ser
1               5                   10                  15

Thr Thr Ile Phe Ser Leu Asp Leu Lys Leu Ile Ile Phe Gln Gln Arg
            20                  25                  30

Gln Val Asn Gln Glu Ser Leu Lys Leu Leu Asn Lys Leu Gln Thr Leu
        35                  40                  45

Ser Ile Gln Gln Cys Leu Pro His Arg Lys Asn Phe Leu Leu Pro Gln
    50                  55                  60

Lys Ser Leu Ser Pro Gln Gln Tyr Gln Lys Gly His Thr Leu Ala Ile
65                  70                  75                  80

Leu His Glu Met Leu Gln Gln Ile Phe Ser Leu Phe Arg Ala Asn Ile
                85                  90                  95

Ser Leu Asp Gly Trp Glu Glu Asn His Thr Glu Lys Phe Leu Ile Gln

```
                  100                 105                 110
Leu His Gln Gln Leu Glu Tyr Leu Glu Ala Leu Met Gly Leu Glu Ala
            115                 120                 125

Glu Lys Leu Ser Gly Thr Leu Gly Ser Asp Asn Leu Arg Leu Gln Val
    130                 135                 140

Lys Met Tyr Phe Arg Arg Ile His Asp Tyr Leu Glu Asn Gln Asp Tyr
145                 150                 155                 160

Ser Thr Cys Ala Trp Ala Ile Val Gln Val Glu Ile Ser Arg Cys Leu
                165                 170                 175

Phe Phe Val Phe Ser Leu Thr Glu Lys Leu Ser Lys Gln Asp Glu Asp
            180                 185                 190

Pro

<210> SEQ ID NO 27
<211> LENGTH: 192
<212> TYPE: PRT
<213> ORGANISM: Artificial Sequence
<220> FEATURE:
<223> OTHER INFORMATION: Truncated interferon-epsilon.

<400> SEQUENCE: 27

Met Ile Ile Lys His Phe Phe Gly Thr Val Leu Val Leu Leu Ala Ser
1               5                   10                  15

Thr Thr Ile Phe Ser Leu Asp Leu Lys Leu Ile Ile Phe Gln Gln Arg
            20                  25                  30

Gln Val Asn Gln Glu Ser Leu Lys Leu Leu Asn Lys Leu Gln Thr Leu
        35                  40                  45

Ser Ile Gln Gln Cys Leu Pro His Arg Lys Asn Phe Leu Leu Pro Gln
    50                  55                  60

Lys Ser Leu Ser Pro Gln Gln Tyr Gln Lys Gly His Thr Leu Ala Ile
65                  70                  75                  80

Leu His Glu Met Leu Gln Gln Ile Phe Ser Leu Phe Arg Ala Asn Ile
                85                  90                  95

Ser Leu Asp Gly Trp Glu Glu Asn His Thr Glu Lys Phe Leu Ile Gln
            100                 105                 110

Leu His Gln Gln Leu Glu Tyr Leu Glu Ala Leu Met Gly Leu Glu Ala
        115                 120                 125

Glu Lys Leu Ser Gly Thr Leu Gly Ser Asp Asn Leu Arg Leu Gln Val
    130                 135                 140

Lys Met Tyr Phe Arg Arg Ile His Asp Tyr Leu Glu Asn Gln Asp Tyr
145                 150                 155                 160

Ser Thr Cys Ala Trp Ala Ile Val Gln Val Glu Ile Ser Arg Cys Leu
                165                 170                 175

Phe Phe Val Phe Ser Leu Thr Glu Lys Leu Ser Lys Gln Glu Asp Pro
            180                 185                 190

<210> SEQ ID NO 28
<211> LENGTH: 15
<212> TYPE: DNA
<213> ORGANISM: Artificial Sequence
<220> FEATURE:
<223> OTHER INFORMATION: Mutated coding sequence.

<400> SEQUENCE: 28
gacccagacc cttag                                                    15

<210> SEQ ID NO 29
```

```
<211> LENGTH: 193
<212> TYPE: PRT
<213> ORGANISM: Artificial Sequence
<220> FEATURE:
<223> OTHER INFORMATION: Truncated interferon-epsilon.

<400> SEQUENCE: 29

Met Ile Ile Lys His Phe Phe Gly Thr Val Leu Val Leu Leu Ala Ser
 1               5                  10                  15

Thr Thr Ile Phe Ser Leu Asp Leu Lys Leu Ile Ile Phe Gln Gln Arg
             20                  25                  30

Gln Val Asn Gln Glu Ser Leu Lys Leu Leu Asn Lys Leu Gln Thr Leu
         35                  40                  45

Ser Ile Gln Gln Cys Leu Pro His Arg Lys Asn Phe Leu Leu Pro Gln
     50                  55                  60

Lys Ser Leu Ser Pro Gln Gln Tyr Gln Lys Gly His Thr Leu Ala Ile
 65                  70                  75                  80

Leu His Glu Met Leu Gln Gln Ile Phe Ser Leu Phe Arg Ala Asn Ile
                 85                  90                  95

Ser Leu Asp Gly Trp Glu Glu Asn His Thr Glu Lys Phe Leu Ile Gln
             100                 105                 110

Leu His Gln Gln Leu Glu Tyr Leu Glu Ala Leu Met Gly Leu Glu Ala
         115                 120                 125

Glu Lys Leu Ser Gly Thr Leu Gly Ser Asp Asn Leu Arg Leu Gln Val
    130                 135                 140

Lys Met Tyr Phe Arg Arg Ile His Asp Tyr Leu Glu Asn Gln Asp Tyr
145                 150                 155                 160

Ser Thr Cys Ala Trp Ala Ile Val Gln Val Glu Ile Ser Arg Cys Leu
                165                 170                 175

Phe Phe Val Phe Ser Leu Thr Glu Lys Leu Ser Lys Gln Asp Pro Asp
            180                 185                 190

Pro

<210> SEQ ID NO 30
<211> LENGTH: 13
<212> TYPE: PRT
<213> ORGANISM: Artificial Sequence
<220> FEATURE:
<223> OTHER INFORMATION: Motif.
<221> NAME/KEY: VARIANT
<222> LOCATION: (1)...(1)
<223> OTHER INFORMATION: Xaa is Leu, Phe, or Ile.
<221> NAME/KEY: VARIANT
<222> LOCATION: (2)...(2)
<223> OTHER INFORMATION: Xaa is His or Tyr.
<221> NAME/KEY: VARIANT
<222> LOCATION: (4)...(4)
<223> OTHER INFORMATION: Xaa is Val, Met, or Leu.
<221> NAME/KEY: VARIANT
<222> LOCATION: (5)...(5)
<223> OTHER INFORMATION: Xaa is Ile, Met, or Leu.
<221> NAME/KEY: VARIANT
<222> LOCATION: (7)...(7)
<223> OTHER INFORMATION: Xaa is Gln or Asn.
<221> NAME/KEY: VARIANT
<222> LOCATION: (8)...(8)
<223> OTHER INFORMATION: Xaa is Thr, Ile, Ser, or Val.
<221> NAME/KEY: VARIANT
<222> LOCATION: (10)...(10)
<223> OTHER INFORMATION: Xaa is Asn, Ser, Ala.
<221> NAME/KEY: VARIANT
<222> LOCATION: (11)...(11)
<223> OTHER INFORMATION: Xaa is Leu or Ile.

<400> SEQUENCE: 30
```

```
Xaa Xaa Glu Xaa Xaa Gln Xaa Xaa Phe Xaa Xaa Phe Arg
 1               5                   10
```

<210> SEQ ID NO 31
<211> LENGTH: 13
<212> TYPE: PRT
<213> ORGANISM: Artificial Sequence
<220> FEATURE:
<223> OTHER INFORMATION: Motif.
<221> NAME/KEY: VARIANT
<222> LOCATION: (3)...(3)
<223> OTHER INFORMATION: Xaa is Phe, Ser, Asp, Thr, or His.
<221> NAME/KEY: VARIANT
<222> LOCATION: (7)...(7)
<223> OTHER INFORMATION: Xaa is Glu, Ala, or Thr.
<221> NAME/KEY: VARIANT
<222> LOCATION: (8)...(8)
<223> OTHER INFORMATION: Xaa is Val, Thr, or Ile.
<221> NAME/KEY: VARIANT
<222> LOCATION: (10)...(10)
<223> OTHER INFORMATION: Xaa is Arg or Gln.
<221> NAME/KEY: VARIANT
<222> LOCATION: (11)...(11)
<223> OTHER INFORMATION: Xaa is Ala, Met, Leu, or Val.

<400> SEQUENCE: 31

```
Tyr Ser Xaa Cys Ala Trp Xaa Xaa Val Xaa Xaa Glu Ile
 1               5                   10
```

<210> SEQ ID NO 32
<211> LENGTH: 9
<212> TYPE: DNA
<213> ORGANISM: Artificial Sequence
<220> FEATURE:
<223> OTHER INFORMATION: Nucleotide sequence.

<400> SEQUENCE: 32 atgcacggg                                                                     9

<210> SEQ ID NO 33
<211> LENGTH: 9
<212> TYPE: DNA
<213> ORGANISM: Artificial Sequence
<220> FEATURE:
<223> OTHER INFORMATION: Nucleotide sequence.

<400> SEQUENCE: 33 cccgtgcat                                                                     9

INTERFERON-ε

CROSS-REFERENCE TO RELATED APPLICATIONS

This application claims the benefit of U.S. Provisional application No. 60/101,012 (filed Sep. 18, 1998), No. 60/118,578 (filed Feb. 5, 1999), and No. 60/142,766 (filed Jul. 8, 1999), the contents of which are incorporated by reference.

TECHNICAL FIELD

The present invention relates generally to a new cytokine having diagnostic and therapeutic uses. In particular, the present invention relates to a novel interferon, designated "interferon-ε," and to nucleic acid molecules encoding interferon-ε.

BACKGROUND OF THE INVENTION

Cellular differentiation of multicellular organisms is controlled by hormones and polypeptide growth factors. These diffusible molecules allow cells to communicate with each other and act in concert to form tissues and organs, and to repair and regenerate damaged tissue. Examples of hormones and growth factors include the steroid hormones, parathyroid hormone, follicle stimulating hormone, the interferons, the interleukins, platelet derived growth factor, epidermal growth factor, and granulocyte-macrophage colony stimulating factor, among others.

Hormones and growth factors influence cellular metabolism by binding to receptor proteins. Certain receptors are integral membrane proteins that bind with the hormone or growth factor outside the cell, and that are linked to signaling pathways within the cell, such as second messenger systems. Other classes of receptors are soluble intracellular molecules.

Of particular interest, from a therapeutic standpoint, are the interferons (reviews on interferons are provided by De Maeyer and De Maeyer-Guignard, "Interferons," in *The Cytokine Handbook 3rd Edition,* Thompson (ed.), pages 491–516 (Academic Press Ltd. 1998), and by Walsh, *Biopharmaceuticals: Biochemistry and Biotechnology,* pages 158–188 (John Wiley & Sons 1998)). Interferons exhibit a variety of biological activities, and are useful for the treatment of certain autoimmune diseases, particular cancers, and the enhancement of the immune response against infectious agents, including viruses, bacteria, fungi, and protozoa. To date, six forms of interferon have been identified, which have been classified into two major groups. The so-called "type I" interferons include interferon-α, interferon-β, interferon-ω, interferon-δ, and interferon-τ. Currently, interferon-γ and one subclass of interferon-α are the only type II interferons.

Type I interferons are thought to be derived from the same ancestral gene, and the type I interferons have retained sufficient similar structure to act by the same cell surface receptor. The α-chain of the human interferon-α/β receptor comprises an extracellular N-terminal domain, which has the characteristics of a class II cytokine receptor. Interferon-γ does not share significant homology with the type I interferons or with the type II interferon-α subtype, but shares a number of biological activities with the type I interferons.

In humans, at least 16 non-allelic genes code for different subtypes of interferon-α, while interferons β and ω are encoded by single genes. Type I interferon genes are clustered in the short arm of chromosome 9. Unlike typical structural human genes, interferon-α, interferon-β, and interferon-ω lack introns. A single gene for human interferon-γ is localized on chromosome 12 and contains three introns. To date, interferon-τ has been described only in cattle and sheep, while interferon-δ has been described only in pigs.

It is believed that all cells may be capable of producing interferons α and β in response to viral infection, double-stranded RNA molecules, growth factors, and cytokines. Normally, however, interferon-α is produced by lymphocytes, macrophages, and monocytes, while interferon-β is synthesized by fibroblasts and some epithelial cells. Interferon-γ is produced by T cells or natural killer cells.

Clinicians are taking advantage of the multiple activities of interferons by using the proteins to treat a wide range of conditions. For example, one form of interferon-α has been approved for use in more than 50 countries for the treatment of medical conditions such as hairy cell leukemia, renal cell carcinoma, basal cell carcinoma, malignant melanoma, AIDS-related Kaposi's sarcoma, multiple myeloma, chronic myelogenous leukemia, non-Hodgkin's lymphoma, laryngeal papillomatosis, mycosis fungoides, condyloma acuminata, chronic hepatitis B, hepatitis C, chronic hepatitis D, and chronic non-A, non-B/C hepatitis. The U.S. Food and Drug Administration has approved the use of interferon-β to treat multiple sclerosis, a chronic disease of the nervous system. Interferon-γ is used to treat chronic granulomatous diseases, in which the interferon enhances the patient's immune response to destroy infectious bacterial, fungal, and protozoal pathogens. Clinical studies also indicate that interferon-γ may be useful in the treatment of AIDS, leishmaniasis, and lepromatous leprosy.

Although new uses of known interferons may be discovered, a need exists for the provision of new interferons for biopharmaceuticals.

SUMMARY OF THE INVENTION

The present invention provides a novel interferon, designated "interferon-ε." The present invention also provides interferon-ε polypeptides and interferon-ε fusion proteins, as well as nucleic acid molecules encoding such polypeptides and proteins.

In particular, the present invention provides isolated polypeptides having an amino acid sequence that is at least 70% identical to an amino acid sequence selected from the group consisting of (a) amino acid residues 22–208 of SEQ ID NO:2, (b) amino acid residues 22–208 of SEQ ID NO:5, (c) the amino acid sequence of SEQ ID NO:2, and (d) the amino acid sequence of SEQ ID NO:5, wherein the isolated polypeptide either specifically binds with an antibody that specifically binds with a polypeptide having the amino acid sequence of either SEQ ID NO:2 or SEQ ID NO:5, or exhibits anti-viral activity or anti-proliferative activity. The present invention also provides isolated polypeptides having an amino acid sequence that is at least 80%, or at least 90%, identical to one of amino acid sequences (a)–(d). Examples of such polypeptides include polypeptides comprising the amino acid sequence of either SEQ ID NO:2 or SEQ ID NO:5. The present invention also contemplates isolated polypeptides comprising a first amino acid sequence consisting of amino acid residues 22 to 208 of either SEQ ID NO:2 or SEQ ID NO:5, as well as polypeptides that further comprise a signal secretory sequence that resides in an amino-terminal position relative to the first amino acid sequence, wherein the signal secretory sequence comprises amino acid residues 1 to 21 of the amino acid sequence of SEQ ID NO:2. The present invention also includes various truncated variant interferon-ε polypeptides, as described below.

The present invention further provides pharmaceutical compositions that comprise such polypeptides, and a pharmaceutically acceptable carrier.

The present invention also includes variant human interferon-ε polypeptides, wherein the amino acid sequence of the variant is characterized by at least one amino acid substitution within SEQ ID NO:2 selected from the group consisting of: (a) an alanine residue for Thr$^{77}$, (b) a threonine residue for Ser$^{38}$, (c) a valine residue for Ile$^{80}$, (d) an aspartate residue for Glu$^{107}$, and (e) a valine residue for Ile$^{167}$. Additional variant human interferon-ε polypeptides include those in which the amino acid sequence of the variant polypeptide shares an identity with the amino acid sequence of SEQ ID NO:2 selected from the group consisting of at least 70% identity, at least 80% identity, at least 90% identity, at least 95% identity, or greater than 95% identity, and wherein any difference between the amino acid sequence of the variant polypeptide and the amino acid sequence of SEQ ID NO:2 is due to one or more conservative amino acid substitutions.

The present invention also includes human interferon polypeptides that comprise the amino acid sequence motif "[LFI][HY]E[VML][IML]Q[QN][TISV]F[NSA][LI]FR," (SEQ ID NO:30), wherein the motif is further defined by at least one condition selected from the group consisting of: (a) the first residue is L, (b) the second residue is H, (c) the seventh residue is Q, (d) the tenth residue is S, and (e) the eleventh residue is L. The present invention further provides human interferon polypeptides that comprise the amino acid sequence motif "YS[PSDTH]CAW[EAT][VTI]V[RQ][AMLV]EI," (SEQ ID NO:31), wherein the motif is further defined by at least one condition selected from the group consisting of: (a) the third residue is T, (b) the seventh residue is A, and (c) the tenth residue is Q.

The present invention further provides human interferon polypeptides that comprise an amino acid sequence consisting of amino acid residues 189 to 208 of SEQ ID NO:2. Suitable polypeptides include those in which the amino acid sequence occurs at the C-terminus of the polypeptide.

The present invention also contemplates polypeptides consisting of amino acid residues 22 to 94 of either SEQ ID NO:2 or SEQ ID NO:5.

The present invention also provides isolated nucleic acid molecules that encode an interferon-ε polypeptide, wherein the nucleic acid molecule is selected from the group consisting of (a) a nucleic acid molecule comprising the nucleotide sequence of SEQ ID NO:3, (b) a nucleic acid molecule comprising the nucleotide sequence of SEQ ID NO:6, (c) a nucleic acid molecule that remains hybridized following stringent wash conditions to a nucleic acid molecule consisting of the nucleotide sequence of SEQ ID NO:1, or the complement of SEQ ID NO:1, and (d) a nucleic acid molecule that remains hybridized following stringent wash conditions to a nucleic acid molecule consisting of the nucleotide sequence of SEQ ID NO:4, or the complement of SEQ ID NO:4. Such nucleic acid molecules include those in which any difference between the amino acid sequence encoded by the nucleic acid molecule and the corresponding amino acid sequence of either SEQ ID NO:2 or SEQ ID NO:5 is due to a conservative amino acid substitution.

The present invention further provides isolated nucleic acid molecules, comprising the nucleotide sequence of nucleotides 517 to 1077 of either SEQ ID NO:1 or SEQ ID NO:4, isolated nucleic acid molecules comprising the nucleotide sequence of nucleotides 454 to 1077 of either SEQ ID NO:1 or SEQ ID NO:4, and isolated nucleic acid molecules comprising the nucleotide sequence of nucleotides 1 to 1234 of either SEQ ID NO:1 or SEQ ID NO:4.

The present invention also includes murine interferon-ε, such as isolated polypeptides comprising a first amino acid sequence consisting of amino acid residues 22 to 192 of SEQ ID NO:24. These polypeptides can further comprise a signal secretory sequence that resides in an amino-terminal position relative to the first amino acid sequence, wherein the signal secretory sequence comprises amino acid residues 1 to 21 of the amino acid sequence of SEQ ID NO:24. Examples of variant murine interferon-ε molecules include isolated polypeptides having an amino acid sequence that is at least 70%, at least 80%, or at least 90% identical to either amino acid residues 22–192 of SEQ ID NO:24, or the amino acid sequence of SEQ ID NO:24, wherein the isolated polypeptide either (a) specifically binds with an antibody that specifically binds with a polypeptide consisting of the amino acid sequence of SEQ ID NO:24, or (b) exhibits anti-viral activity or anti-proliferative activity. Additional variant murine interferon-ε polypeptides include those in which the amino acid sequence of the variant polypeptide shares an identity with the amino acid sequence of SEQ ID NO:24 selected from the group consisting of at least 70% identity, at least 80% identity, at least 90% identity, at least 95% identity, or greater than 95% identity, and wherein any difference between the amino acid sequence of the variant polypeptide and the amino acid sequence of SEQ ID NO:24 is due to one or more conservative amino acid substitutions.

The present invention further contemplates isolated nucleic acid molecules that encode an interferon-ε polypeptide, wherein the nucleic acid molecule is selected from the group consisting of (a) a nucleic acid molecule comprising the nucleotide sequence of SEQ ID NO:25, and (b) a nucleic acid molecule that remains hybridized following stringent wash conditions to a nucleic acid molecule consisting of the nucleotide sequence of SEQ ID NO:23, or the complement of SEQ ID NO:23. Such nucleic acid molecules include those in which any difference between the amino acid sequence encoded by the nucleic acid molecule and the corresponding amino acid sequence of SEQ ID NO:24 is due to a conservative amino acid substitution. An illustrative nucleic acid molecule that encodes murine interferon-ε comprises the nucleotide sequence of nucleotides 842 to 1354 of SEQ ID NO:23.

The present invention further provides chimeric interferon-ε proteins having the structure: [hA or mA]-[hAB or mAB]-[hB or mB]-[hBC or mBC]-[hC or mC]-[hCD or mCD]-[hD or mD]-[hDE or mDE]-[hE or, mE], wherein the designations "A" through "E" indicate an interferon-ε helix region, designations "AB" through "DE" indicate an interferon-ε loop region, and "h" and "m" refer to human interferon-ε and murine interferon-ε, respectively. Illustrative chimeric interferon-ε proteins include polypeptides having the structure [mA]-[hAB]-[hB]-[hBC]-[hC]-[mCD]-[mD]-[hDE]-[mE], [mA]-[hAB]-[hB]-[hBC]-[mC]-[hCD]-[hD -]-[mDE]-[hE], [mA]-[hAB]-[hB]-[hBC]-[mC]-[hCD]-[mD]-[mDE]-[hE], and [hA]-[mAB]-[mB]-[mBC]-[mC]-[hCD]-[hD]-[mDE]-[hE]. Such chimeric interferon-ε proteins can further comprise at least one of (a) a signal sequence, wherein the signal sequence is located in an N-terminal position, and (b) a human interferon-ε C-terminal amino acid sequence or a murine interferon-ε C-terminal amino acid sequence. An illustrative human interferon-ε C-terminal amino acid sequence comprises amino acid residues 185 to 208 of SEQ ID NO:2, and an illustrative murine interferon-ε C-terminal amino acid sequence comprises amino acid residues 184 to 192 of SEQ ID NO:24. The present invention also includes nucleic acid molecules encoding such chimeric interferon-ε proteins.

The present invention also provides vectors and expression vectors comprising such nucleic acid molecules, recombinant host cells comprising such vectors and expression vectors, and recombinant viruses comprising such expression vectors. These expression vectors and recombinant host cells can be used to prepare interferon-ε polypeptides. In addition, the present invention provides pharmaceutical compositions, comprising a pharmaceutically acceptable carrier and at least one of such an expression vector or recombinant virus. Preferably, such pharmaceutical compositions comprise a human interferon-ε gene, a murine interferon-ε gene, or a variant thereof.

The present invention further contemplates antibodies and antibody fragments that specifically bind with interferon-ε polypeptides. Such antibodies include polyclonal antibodies, murine monoclonal antibodies, humanized antibodies derived from murine monoclonal antibodies, and human monoclonal antibodies. Examples of antibody fragments include $F(ab')_2$, $F(ab)_2$, Fab', Fab, Fv, scFv, and minimal recognition units.

The present invention also provides methods for detecting the presence of interferon-ε RNA in a biological sample, comprising the steps of:

(a) contacting an interferon-ε nucleic acid probe under hybridizing conditions with either (i) test RNA molecules isolated from the biological sample, or (ii) nucleic acid molecules synthesized from the isolated RNA molecules, wherein the probe has a nucleotide sequence comprising a portion of the nucleotide sequence selected from the group consisting of SEQ ID NO:1, the complement of SEQ ID NO:1, SEQ ID NO:4, and the complement of SEQ ID NO:4, and (b) detecting the formation of hybrids of the nucleic acid probe and either the test RNA molecules or the synthesized nucleic acid molecules, wherein the presence of the hybrids indicates the presence of interferon-ε RNA in the biological sample.

In addition, the presence of interferon-ε polypeptide in a biological sample can be detected by methods that comprise the steps of (a) contacting the biological sample with an antibody, or an antibody fragment, that specifically binds with a polypeptide having the amino acid sequence of either SEQ ID NO:2 or SEQ ID NO:5, wherein the contacting is performed under conditions that allow the binding of the antibody or antibody fragment to the biological sample, and (b) detecting any of the bound antibody or bound antibody fragment.

The present invention also provides kits for detecting interferon-ε nucleic acid molecules or interferon-ε polypeptides. For example, a kit for detection of interferon-ε nucleic acid molecules may comprise a container that comprises a nucleic acid molecule, wherein the nucleic acid molecule is selected from the group consisting of (a) a nucleic acid molecule comprising the nucleotide sequence of nucleotides 517 to 1077 of SEQ ID NO:1, (b) a nucleic acid molecule comprising the complement of the nucleotide sequence of SEQ ID NO:1, (c) a nucleic acid molecule that is a fragment of (a) consisting of at least eight nucleotides, (d) a nucleic acid molecule that is a fragment of (a) consisting of at least eight nucleotides, (e) a nucleic acid molecule comprising the nucleotide sequence of nucleotides 517 to 1077 of SEQ ID NO:4, (f) a nucleic acid molecule comprising the complement of the nucleotide sequence of SEQ ID NO:4, (g) a nucleic acid molecule that is a fragment of (e) consisting of at least eight nucleotides, and (h) a nucleic acid molecule that is a fragment of (f) consisting of at least eight nucleotides. Such kits may further comprise a second container that comprises one or more reagents capable of indicating the presence of the nucleic acid molecule. A kit for detection of interferon-ε polypeptide may comprise a container that comprises an antibody, or an antibody fragment, that specifically binds with a polypeptide having the amino acid sequence of either SEQ ID NO:2 or SEQ ID NO:5.

The present invention also contemplates isolated nucleic acid molecules comprising a nucleotide sequence that encodes an interferon-ε secretion signal sequence and a nucleotide sequence that encodes a biologically active polypeptide, wherein the interferon-ε secretion signal sequence comprises an amino acid sequence of residues 1 to 21 of SEQ ID NO:2. Illustrative biologically active polypeptides include Factor VIIa, proinsulin, insulin, follicle stimulating hormone, tissue type plasminogen activator, tumor necrosis factor, interleukin, colony stimulating factor, interferon, erythropoietin, and thrombopoietin. Moreover, the present invention provides fusion proteins comprising an interferon-ε secretion signal sequence and a polypeptide, wherein the interferon-ε secretion signal sequence comprises an amino acid sequence of residues 1 to 21 of SEQ ID NO:2. Additional fusion proteins comprise an interferon-ε moiety and an immunoglobulin moiety. An illustrative immunoglobulin moiety is an immunoglobulin heavy chain constant region, such as a human $F_c$ fragment. The present invention also includes isolated nucleic acid molecules that encode such fusion proteins.

The present invention also contemplates anti-idiotype antibodies, or anti-idiotype antibody fragments, that specifically bind with an anti-interferon-ε antibody or antibody fragment, wherein the anti-idiotype antibody, or anti-idiotype antibody fragment, possesses anti-viral activity or anti-proliferative activity.

The present invention further provides: (1) isolated polypeptides having an amino acid sequence consisting of amino acid residues 27–94 of either SEQ ID NO:2 or SEQ ID NO:5, (2) isolated polypeptides that comprise a peptide segment having amino acid residues 173 to 188 of SEQ ID NO:2, and (3) isolated polypeptides that comprise a first peptide segment having amino acid residues 173 to 188 of SEQ ID N0:2 and a second peptide segment that resides in a carboxyl-terminal position relative to the first peptide segment, wherein the second peptide segment has the amino acid sequence of amino acid residues 185 to 208 of SEQ ID NO:2. The present invention also includes isolated nucleic acid molecules that encode these polypeptides.

The present invention includes methods for detecting the presence of murine interferon-ε RNA in a biological sample, comprising the steps of: (a) contacting an interferon-ε nucleic acid probe under hybridizing conditions with either (i) test RNA molecules isolated from the biological sample, or (ii) nucleic acid molecules synthesized from the isolated RNA molecules, wherein the probe has a nucleotide sequence comprising a portion of the nucleotide sequence of either SEQ ID NO:23, or the complement of SEQ ID NO:23, and (b) detecting the formation of hybrids of the nucleic acid probe and either the test RNA molecules or the synthesized nucleic acid molecules, wherein the presence of the hybrids indicates the presence of interferon-ε RNA in the biological sample. The present invention also provides methods for detecting the presence of murine interferon-ε in a biological sample, comprising the steps of: (a) contacting the biological sample with an antibody, or an antibody fragment, that specifically binds with a polypeptide consisting of the amino acid sequence of SEQ ID NO:24, wherein the contacting is performed under conditions that allow the binding of the antibody or antibody fragment to the biological sample, and (b) detecting any of the bound antibody or bound antibody fragment. The present invention also contemplates kits for performing these methods.

The present invention also provides expression vectors comprising a murine interferon-ε promoter, wherein the promoter comprises nucleotides 1 to 778 of SEQ ID NO:23.

The present invention further includes methods for detecting an alteration in chromosome 9. In particular, human interferon-ε nucleotide sequences can be used to examine chromosome 9p, for example, in the 9p22.2 region. Illustrative chromosomal aberrations at the interferon-ε gene locus include aneuploidy, gene copy number changes, insertions, deletions, restriction site changes and rearrangements. These aberrations can occur within flanking sequences, including upstream promoter and regulatory regions, and can be manifested as physical alterations within a coding sequence or changes in gene expression level. Such methods are effected by examining is the interferon-ε gene and its gene products. In general, suitable assay methods include molecular genetic techniques known to those in the art, such as restriction fragment length polymorphism analysis, short tandem repeat analysis employing polymerase chain reaction techniques, ligation chain reaction, ribonuclease protection assays, use of single-nucleotide polymorphisms, protein truncation assays, and other genetic linkage techniques known in the art.

In particular, the present invention provides methods for diagnosing an alteration in the interferon-ε gene of an individual, comprising: (a) amplifying nucleic acid molecules that encode interferon-ε from RNA isolated from a biological sample of the individual, and (b) detecting a mutation in the amplified nucleic acid molecules, wherein the presence of a mutation indicates an alteration in the interferon-ε gene. Similarly, methods of detecting a chromosome 9p22.2 abnormality in a subject comprise: (a) amplifying nucleic acid molecules that encode interferon-ε from RNA isolated from a biological sample of the subject, and (b) detecting a mutation in the amplified nucleic acid molecules, wherein the presence of a mutation indicates a chromosome 9p22.2 abnormality. In variations of these methods, the detecting step is performed by comparing the nucleotide sequence of the amplified nucleic acid molecules to the nucleotide sequence of SEQ ID NOs:1 or 4. Alternatively, the detecting step can be performed by fractionating the amplified nucleic acid molecules and control nucleic acid molecules that encode the amino acid sequence of SEQ ID NOs:2 or 5, and comparing the lengths of the fractionated amplified and control nucleic acid molecules. Exemplary methods for amplification include polymerase chain reaction or reverse transcriptase-polymerase chain reaction.

The present invention also includes methods for detecting a chromosome 9p22.2 abnormality in a subject comprising: (a) amplifying nucleic acid molecules that encode interferon-ε from RNA isolated from a biological sample of the subject, (b) transcribing the amplified nucleic acid molecules to express interferon-ε mRNA, (c) translating interferon-ε mRNA to produce interferon-ε polypeptides, and (d) detecting a mutation in the interferon-ε polypeptides, wherein the presence of a mutation indicates a chromosome 9p22.2 abnormality. In variations of these methods, the detection step can be performed by fractionating, under denaturing conditions, the interferon-ε polypeptides and control polypeptides that encode the amino acid sequence of SEQ ID NOs:2 or 5, and comparing the sizes of the fractionated amplified and control polypeptides. Similar methods can be used to detect a mutation of an interferon-ε gene in an individual.

The present invention further includes methods of inhibiting a viral infection of cells, comprising the step of administering a composition comprising interferon-ε to the cells. For example, the composition can be a pharmaceutical composition, which is administered in a therapeutically effective amount to a subject which has a viral infection. In vivo treatment of a viral infection can provide at least one physiological effect selected from the group consisting of decreased viral titer, decreased detectable viral antigen, and increased anti-viral antibody titer.

The present invention also includes methods of inhibiting the proliferation of tumor cells, comprising the step of administering a composition comprising interferon-ε to the tumor cells. In an in vivo approach, the composition is a pharmaceutical composition, administered in a therapeutically effective amount to a subject which has a tumor. Such in vivo administration can provide at least one physiological effect selected from the group consisting of decreased number of tumor cells, decreased metastasis, decreased size of a solid tumor, and increased necrosis of a tumor.

The present invention further includes methods of treating a lymphoproliferative disorder in a subject, comprising the step of administering a therapeutically effective amount of pharmaceutical composition to the subject, wherein the pharmaceutical composition comprises interferon-ε. Illustrative lymphoproliferative disorders include B-cell lymphoma, chronic lymphatic leukemia, and acute lymphatic leukemia.

Methods of treatment can be performed with interferon-ε polypeptides and variants, including human interferon-ε, murine interferon-ε, chimeric interferon-ε, and the like.

These and other aspects of the invention will become evident upon reference to the following detailed description and the attached drawings. In addition, various references are identified below and are incorporated by reference in their entirety.

BRIEF DESCRIPTION OF THE DRAWINGS

FIG. 1 shows the pairwise sequence alignment between that amino acid sequence an interferon-ε ("zifne-1") [SEQ ID NO:5] and the amino acid sequence of human interferon-β (PDB code 1AU1) [SEQ ID NO:7]. The sequences have 38% identity over an overlap region of 162 amino acids.

conditioned medium from BHK cells transfected with an expression vector comprising a DHFR gene and a nucleotide sequence encoding murine interferon-ε with a Glu-Glu tag; Untagged mIFNE CM: conditioned medium from BHK cells transfected with an expression vector comprising a DHFR gene and a nucleotide sequence encoding murine interferon-ε.

Figure 4:
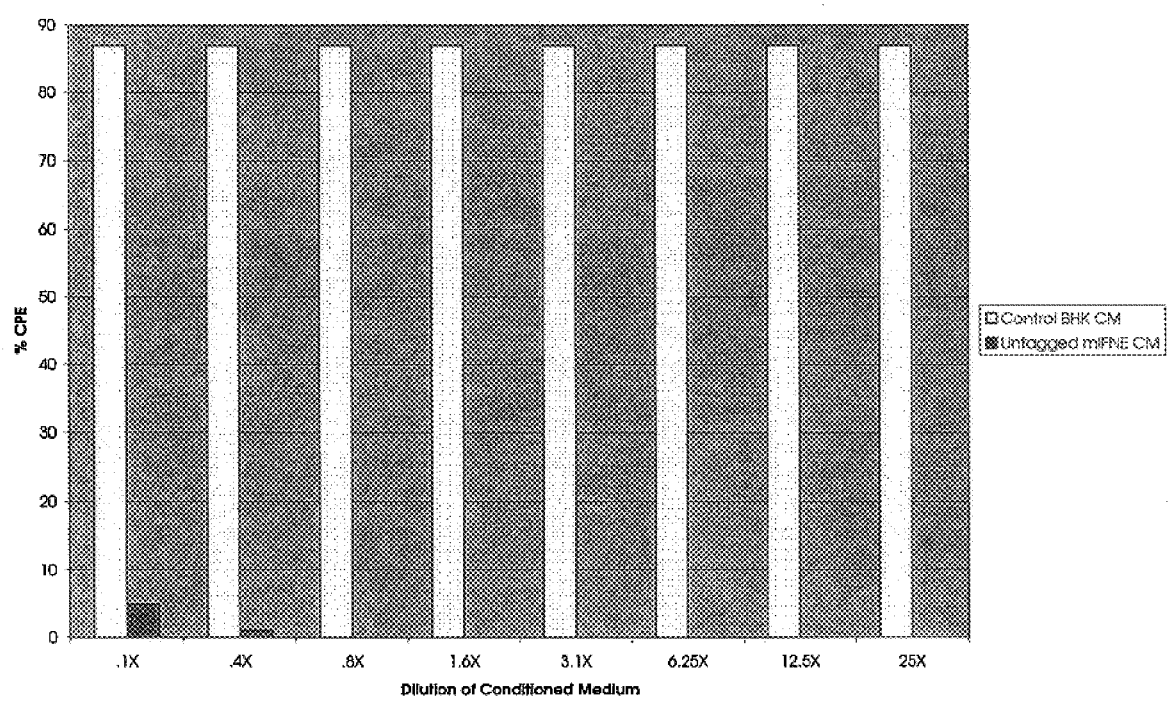

FIG. 4 shows the antiviral effect of murine interferon-ε on human HeLa cells infected with encephalomyocarditis virus. Abbreviations are provided in the previous paragraph.

DETAILED DESCRIPTION OF THE INVENTION

1. Overview

Prior to the discovery of the novel interferon described herein, the interferon family was believed to be comprised of six broad classes of molecules. The alpha, omega, beta, and delta interferons are all highly related in sequence, while the gamma class is not. In addition, there are several highly structurally related members in the alpha class. Functionally, interferons are characterized by their anti-viral and anti-proliferative responses in cells.

The amino acid sequence of a new human interferon, initially designated as "zifne," was found to be approximately equally similar to the alpha, beta, and delta classes. Based on the divergence of zifne from the alpha, beta and delta classes, zifne is proposed to be the first known member of a distinct "epsilon" class of interferon. The localization of the interferon-ε gene to human chromosome 9p22.2 is consistent with the designation of interferon-ε as a new Type I interferon.

A nucleic acid molecule containing a sequence that encodes human zifne has the nucleotide sequence of SEQ ID NO:1. The encoded polypeptide has the following amino acid sequence: MIIKHFFGTV LVLLASTTIF SLDLKLI- IFQ QRQVNQESLK LLNKLQTLSI QQCLPHRKNF LLPQKSLSPQ QYQKGHTLAI LHEMLQQIFS LFRANISLDG WEENHTEKFL IQLHQQLEYL EALMGLEAEK LSGTLGSDNL RLQVKMYFRR IHDYLENQDY STCAWAIVQV EISRCLFFVF SLTEKL- SKQG RPLNDMKQEL TTEFRSPR (SEQ ID NO:2). Thus, the zifne form of an interferon-ε gene encodes a polypeptide of 208 amino acids. The signal sequence for interferon-ε can be predicted as comprising $Met^1$ through $Ser^{21}$ of SEQ ID NO:2. The mature peptide for interferon-ε begins at $Leu^{22}$, and a monomer of interferon-ε will have a predicted molecular weight of approximately 24 kD. A homodimer of interferon-ε will have a molecular weight of approximately 48 kD. These predicted molecular weights do not include the extra mass contributed by carbohydrate chains potentially branching from N-linked glycosylation sites, as discussed below.

An allelic variant of the zifne gene has also been identified (designated as "zifne-1"). This variant interferon-ε contains an alanine residue at position 77, in place of a threonine residue, as shown in SEQ ID NO:5. The mutation is due to a substitution of a guanosine nucleotide for an adenine nucleotide at position 682, as shown in SEQ ID NO:4. FIG. 1 shows a pairwise sequence alignment of zifne-1 with human interferon-β.

A murine ortholog of the human interferon-ε gene has also been isolated. The murine interferon-ε polypeptide has the following amino acid sequence: MVHRQLPETV LLLLVSSTIF SLEPKRIPFQ LWMNRESLQL LKPLPSSSVQ QCLAHRKNFL LPQQPVSPHQ YQEGQVLAVV HEILQQIFTL LQTHGTMGIW EENHIEKVLA ALHRQLEYVE SLGGLNAAQK SGGSSAQNLR LQIKAYFRRI HDYLENQRYS SCAWI- IVQTE IHRCMFFVFR FTTWLSRQDP DP (SEQ ID NO:24). A genomic DNA fragment that contains the murine interferon-ε gene has the nucleotide sequence provided in SEQ ID NO:23, wherein murine interferon-ε is encoded by nucleotides 779 to 1354. The murine interferon-ε gene has been mapped to mouse chromosome 4 (framework marker D4Mit245, located at 42.5 centimorgans), in a region syntenic to the human interferon-ε locus. The murine interferon-α/-β gene cluster is also located at chromosome 4.

Interferon-ε is a helical cytokine in the interferon class. As such, the polypeptide is characterized by four helices in an up-up-down-down bundle with an extra helix formed by the loop between the third and fourth helices. Thus, helix E in the interferon class corresponds to helix D in the non interferon class of four helix bundle cytokines. Table 5 describes structural features of human interferon-ε.

A human interferon-ε polypeptide having the amino acid sequence of SEQ ID NO:2 or SEQ ID NO:5 will contain at least one disulfide bond, which is formed by $Cys^{53}$ and $Cys^{163}$. Similarly, cysteine residues are located at positions 52 and 162 in the illustrative murine form of zifne (SEQ ID NO:24). In the human forms, $Cys^{53}$ is located at the top of the AB loop, while $Cys^{163}$ is located at the top of helix E. There is also a free cysteine residue ($Cys^{175}$), which may participate in an intermolecular disulfide bond with another interferon-ε monomer. There are two potential N-linked glycosylation sites in the interferon-ε forms described herein. These sites, located at $Asn^{95}$ and $Asn^{104}$, reside in the short connecting loop between helices B and C. Human interferon beta has a single glycosylation site in the BC loop.

Motif analysis of 55 interferon family members from various species has revealed a few residues which appear to be immutable throughout the family. It is expected that disrupting any one of these residues will inactivate the function of any interferon, including interferon-ε. In reference to SEQ ID NO:2 or SEQ ID NO:5, these residues are $Cys^{53}$, $Gln^{71}$, $Gln^{86}$, $Leu^{155}$, $Cys^{163}$, $Ala^{164}$, and $Trp^{165}$. In reference to SEQ ID NO:24, these residues are $Cys^{52}$, $Gln^{70}$, $Gln^{85}$, $Leu^{154}$, $Cys^{162}$, $Ala^{163}$, and $Trp^{164}$.

As mentioned above, $Cys^{53}$ and $Cys^{163}$ form a necessary disulfide bond in the human interferon-ε polypeptide. $Gln^{86}$ is a polar residue on a highly exposed location of helix B and is predicted to be involved in receptor binding. $Gln^{71}$ lies at the bottom of the AB loop and is also highly exposed and may be involved in receptor binding. $Leu^{155}$, $Ala^{164}$ and $Trp^{165}$ have side chains pointing into the core of the structure, and are predicted to be essential for protein structural stability.

Hybridization analyses indicate that the human interferon-ε gene is strongly expressed in placental tissue, and to a lesser extent, in tracheal tissue. Human interferon-ε RNA was also detected in uterine tissue and in benign heart tumor tissue. In contrast, little or no interferon-ε gene expression was detectable in tissues such as heart, lung, brain, liver, skeletal muscle, kidney, spleen, thymus, prostate, testis, ovary, small intestine, colon, peripheral blood lymphocytes, stomach, thyroid, spinal cord, lymph node, adrenal gland, or pancreas. These results show that interferon-ε sequences can be used differentiate among various tissues.

Studies have also shown that human interferon-ε gene expression can be stimulated by typical interferon inducers, such as IL-1β, polyinosinic acid-polycytidylic acid, and tumor necrosis factor-α (TNF-α), in cultured human umbilical vein endothelial cells, and human neonatal dermal fibroblasts. In contrast, interferon-ε gene expression appears to be constitutive in human coronary artery smooth muscle cells, human microvascular endothelial cells, and normal human bronchial epithelial cells.

2. Definitions

In the description that follows, a number of terms are used extensively. The following definitions are provided to facilitate understanding of the invention.

As used herein, "nucleic acid" or "nucleic acid molecule" refers to polynucleotides, such as deoxyribonucleic acid (DNA) or ribonucleic acid (RNA), oligonucleotides, fragments generated by the polymerase chain reaction (PCR), and fragments generated by any of ligation, scission, endonuclease action, and exonuclease action. Nucleic acid molecules can be composed of monomers that are naturally-occurring nucleotides (such as DNA and RNA), or analogs of naturally-occurring nucleotides (e.g., α-enantiomeric forms of naturally-occurring nucleotides), or a combination of both. Modified nucleotides can have alterations in sugar moieties and/or in pyrimidine or purine base moieties. Sugar modifications include, for example, replacement of one or more hydroxyl groups with halogens, alkyl groups, amines, and azido groups, or sugars can be functionalized as ethers or esters. Moreover, the entire sugar moiety can be replaced with sterically and electronically similar structures, such as aza-sugars and carbocyclic sugar analogs. Examples of modifications in a base moiety include alkylated purines and pyrimidines, acylated purines or pyrimidines, or other well-known heterocyclic substitutes. Nucleic acid monomers can be linked by phosphodiester bonds or analogs of such linkages. Analogs of phosphodiester linkages include phosphorothioate, phosphorodithioate, phosphoroselenoate, phosphorodiselenoate, phosphoroanilothioate, phosphoranilidate, phosphoramidate, and the like. The term "nucleic acid molecule" also includes so-called "peptide nucleic acids," which comprise naturally-occurring or modified nucleic acid bases attached to a polyamide backbone. Nucleic acids can be either single stranded or double stranded.

The term "complement of a nucleic acid molecule" refers to a nucleic acid molecule having a complementary nucleotide sequence and reverse orientation as compared to a reference nucleotide sequence. For example, the sequence 5'ATGCACGGG 3' (SEQ ID NO:32) is complementary to 5' CCCGTGCAT 3' (SEQ ID NO:33).

The term "contig" denotes a nucleic acid molecule that has a contiguous stretch of identical or complementary sequence to another nucleic acid molecule. Contiguous sequences are said to "overlap" a given stretch of a nucleic acid molecule either in their entirety or along a partial stretch of the nucleic acid molecule.

The term "degenerate nucleotide sequence" denotes a sequence of nucleotides that includes one or more degenerate codons as compared to a reference nucleic acid molecule that encodes a polypeptide. Degenerate codons contain different triplets of nucleotides, but encode the same amino acid residue (i.e., GAU and GAC triplets each encode Asp).

The term "structural gene" refers to a nucleic acid molecule that is transcribed into messenger RNA (mRNA), which is then translated into a sequence of amino acids characteristic of a specific polypeptide.

An "isolated nucleic acid molecule" is a nucleic acid molecule that is not integrated in the genomic DNA of an organism. For example, a DNA molecule that encodes a growth factor that has been separated from the genomic DNA of a cell is an isolated DNA molecule. Another example of an isolated nucleic acid molecule is a chemically-synthesized nucleic acid molecule that is not integrated in the genome of an organism. A nucleic acid molecule that has been isolated from a particular species is smaller than the complete DNA molecule of a chromosome from that species.

A "nucleic acid molecule construct" is a nucleic acid molecule, either single- or double-stranded, that has been modified through human intervention to contain segments of nucleic acid combined and juxtaposed in an arrangement not existing in nature.

"Linear DNA" denotes non-circular DNA molecules having free 5' and 3' ends. Linear DNA can be prepared from closed circular DNA molecules, such as plasmids, by enzymatic digestion or physical disruption.

"Complementary DNA (cDNA)" is a single-stranded DNA molecule that is formed from an mRNA template by the enzyme reverse transcriptase. Typically, a primer complementary to portions of nRNA is employed for the initiation of reverse transcription. Those skilled in the art also use the term "cDNA" to refer to a double-stranded DNA molecule consisting of such a single-stranded DNA molecule and its complementary DNA strand. The term "cDNA" also refers to a clone of a cDNA molecule synthesized from an RNA template.

A "promoter" is a nucleotide sequence that directs the transcription of a structural gene. Typically, a promoter is located in the 5' non-coding region of a gene, proximal to the transcriptional start site of a structural gene. Sequence elements within promoters that function in the initiation of transcription are often characterized by consensus nucleotide sequences. These promoter elements include RNA polymerase binding sites, TATA sequences, CAAT sequences, differentiation-specific elements (DSEs; McGehee et al., *Mol. Endocrinol.* 7:551 (1993)), cyclic AMP response elements (CREs), serum response elements (SREs; Treisman, *Seminars in Cancer Biol.* 1:47 (1990)), glucocorticoid response elements (GREs), and binding sites for other transcription factors, such as CRE/ATF (O'Reilly et al., *J Biol. Chem.* 267:19938 (1992)), AP2 (Ye et al., *J. Biol. Chem.* 269:25728 (1994)), SP1, cAMP response element binding protein (CREB; Loeken, *Gene Expr.* 3:253 (1993)) and octamer factors (see, in general, Watson et al., eds., *Molecular Biology of the Gene,* 4th ed. (The Benjamin/Cummings Publishing Company, Inc. 1987), and Lemaigre and Rousseau, *Biochem. J* 303:1 (1994)). If a promoter is an inducible promoter, then the rate of transcription increases in response to an inducing agent. In contrast, the rate of transcription is not regulated by an inducing agent if the promoter is a constitutive promoter. Repressible promoters are also known.

A "core promoter" contains essential nucleotide sequences for promoter function, including the TATA box and start of transcription. By this definition, a core promoter may or may not have detectable activity in the absence of specific sequences that may enhance the activity or confer tissue specific activity.

A "regulatory element" is a nucleotide sequence that modulates the activity of a core promoter. For example, a regulatory element may contain a nucleotide sequence that binds with cellular factors enabling transcription exclusively or preferentially in particular cells, tissues, or organelles. These types of regulatory elements are normally associated with genes that are expressed in a "cell-specific," "tissue-specific," or "organelle-specific" manner. For example, the interferon-ε regulatory element preferentially induces gene expression in placental, tracheal, and uterine tissues, as opposed to lung, brain, liver, kidney, spleen, thymus, prostate, testis, ovary, small intestine, and pancreas tissues.

An "enhancer" is a type of regulatory element that can increase the efficiency of transcription, regardless of the distance or orientation of the enhancer relative to the start site of transcription.

"Heterologous DNA" refers to a DNA molecule, or a population of DNA molecules, that does not exist naturally within a given host cell. DNA molecules heterologous to a particular host cell may contain DNA derived from the host cell species (i.e., endogenous DNA) so long as that host DNA is combined with non-host DNA (i.e., exogenous DNA). For example, a DNA molecule containing a non-host DNA segment encoding a polypeptide operably linked to a host DNA segment comprising a transcription promoter is considered to be a heterologous DNA molecule. Conversely, a heterologous DNA molecule can comprise an endogenous gene operably linked with an exogenous promoter. As another illustration, a DNA molecule comprising a gene derived from a wild-type cell is considered to be heterologous DNA if that DNA molecule is introduced into a mutant cell that lacks the wild-type gene.

A "polypeptide" is a polymer of amino acid residues joined by peptide bonds, whether produced naturally or synthetically. Polypeptides of less than about 10 amino acid residues are commonly referred to as "peptides."

A "protein" is a macromolecule comprising one or more polypeptide chains. A protein may also comprise non-peptidic components, such as carbohydrate groups. Carbohydrates and other non-peptidic substituents may be added to a protein by the cell in which the protein is produced, and will vary with the type of cell. Proteins are defined herein in terms of their amino acid backbone structures; substituents such as carbohydrate groups are generally not specified, but may be present nonetheless.

A peptide or polypeptide encoded by a non-host DNA molecule is a "heterologous" peptide or polypeptide.

An "integrated genetic element" is a segment of DNA that has been incorporated into a chromosome of a host cell after that element is introduced into the cell through human manipulation. Within the present invention, integrated genetic elements are most commonly derived from linearized plasmids that are introduced into the cells by electroporation or other techniques. Integrated genetic elements are passed from the original host cell to its progeny.

A "cloning vector" is a nucleic acid molecule, such as a plasmid, cosmid, or bacteriophage, that has the capability of replicating autonomously in a host cell. Cloning vectors typically contain one or a small number of restriction endonuclease recognition sites that allow insertion of a nucleic acid molecule in a determinable fashion without loss of an essential biological function of the vector, as well as nucleotide sequences encoding a marker gene that is suitable for use in the identification and selection of cells transformed with the cloning vector. Marker genes typically include genes that provide tetracycline resistance or ampicillin resistance.

An "expression vector" is a nucleic acid molecule encoding a gene that is expressed in a host cell. Typically, an expression vector comprises a transcription promoter, a gene, and a transcription terminator. Gene expression is usually placed under the control of a promoter, and such a gene is said to be "operably linked to" the promoter. Similarly, a regulatory element and a core promoter are operably linked if the regulatory element modulates the activity of the core promoter.

A "recombinant host" is a cell that contains a heterologous nucleic acid molecule, such as a cloning vector or expression vector. In the present context, an example of a recombinant host is a cell that produces interferon-ε from an expression vector. In contrast, interferon-ε can be produced by a cell that is a "natural source" of interferon-ε, and that lacks an expression vector.

"Integrative transformants" are recombinant host cells, in which heterologous DNA has become integrated into the genomic DNA of the cells.

A "fusion protein" is a hybrid protein expressed by a nucleic acid molecule comprising nucleotide sequences of at least two genes. For example, a fusion protein can comprise at least part of an interferon-ε polypeptide fused with a polypeptide that binds an affinity matrix. Such a fusion protein provides a means to isolate large quantities of interferon-ε using affinity chromatography.

The term "receptor" denotes a cell-associated protein that binds to a bioactive molecule termed a "ligand." This interaction mediates the effect of the ligand on the cell. Receptors can be membrane bound, cytosolic or nuclear; monomeric (e.g., thyroid stimulating hormone receptor, beta-adrenergic receptor) or multimeric (e.g., PDGF receptor, growth hormone receptor, IL-3 receptor, GM-CSF receptor, G-CSF receptor, erythropoietin receptor and IL-6 receptor). Membrane-bound receptors are characterized by a multi-domain structure comprising an extracellular ligand-binding domain and an intracellular effect or domain that is typically involved in signal transduction. In certain membrane-bound receptors, the extracellular ligand-binding domain and the intracellular effector domain are located in separate polypeptides that comprise the complete functional receptor.

In general, the binding of ligand to receptor results in a conformational change in the receptor that causes an interaction between the effector domain and other molecule(s) in the cell, which in turn leads to an alteration in the metabolism of the cell. Metabolic events that are often linked to receptor-ligand interactions include gene transcription, phosphorylation, dephosphorylation, increases in cyclic AMP production, mobilization of cellular calcium, mobilization of membrane lipids, cell adhesion, hydrolysis of inositol lipids and hydrolysis of phospholipids.

The term "secretory signal sequence" denotes a DNA sequence that encodes a peptide (a "secretory peptide") that, as a component of a larger polypeptide, directs the larger polypeptide through a secretory pathway of a cell in which it is synthesized. The larger polypeptide is commonly cleaved to remove the secretory peptide during transit through the secretory pathway.

An "isolated polypeptide" is a polypeptide that is essentially free from contaminating cellular components, such as carbohydrate, lipid, or other proteinaceous impurities associated with the polypeptide in nature. Typically, a preparation of isolated polypeptide contains the polypeptide in a highly purified form, i.e., at least about 80% pure, at least about 90% pure, at least about 95% pure, greater than 95% pure, or greater than 99% pure. One way to show that a particular protein preparation contains an isolated polypeptide is by the appearance of a single band following sodium dodecyl sulfate (SDS)-polyacrylamide gel electrophoresis of the protein preparation and Coomassie Brilliant Blue staining of the gel. However, the term "isolated" does not exclude the presence of the same polypeptide in alternative physical forms, such as dimers or alternatively glycosylated or derivatized forms.

The terms "amino-terminal or N-terminal" and "carboxyl-terminal or C-terminal" are used herein to denote positions within polypeptides. Where the context allows, these terms are used with reference to a particular sequence or portion of a polypeptide to denote proximity or relative position. For example, a certain sequence positioned carboxyl-terminal to a reference sequence within a polypeptide is located proximal to the carboxyl terminus of the reference sequence, but is not necessarily at the carboxyl terminus of the complete polypeptide.

The term "expression" refers to the biosynthesis of a gene product. For example, in the case of a structural gene, expression involves transcription of the structural gene into mRNA and the translation of mRNA into one or more polypeptides.

The term "splice variant" is used herein to denote alternative forms of RNA transcribed from a gene. Splice variation arises naturally through use of alternative splicing sites within a transcribed RNA molecule, or less commonly between separately transcribed RNA molecules, and may result in several mRNAs transcribed from the same gene. Splice variants may encode polypeptides having altered amino acid sequence. The term splice variant is also used herein to denote a polypeptide encoded by a splice variant of an mRNA transcribed from a gene.

As used herein, the term "immunomodulator" includes cytokines, stem cell growth factors, lymphotoxins, co-stimulatory molecules, hematopoietic factors, and synthetic analogs of these molecules.

The term "complement/anti-complement pair" denotes non-identical moieties that form a non-covalently associated, stable pair under appropriate conditions. For instance, biotin and avidin (or streptavidin) are prototypical members of a complement/anti-complement pair. Other exemplary complement/anti-complement pairs include receptor/ligand pairs, antibody/antigen (or hapten or epitope) pairs, sense/antisense polynucleotide pairs, and the like. Where subsequent dissociation of the complement/anti-complement pair is desirable, the complement/anti-complement pair preferably has a binding affinity of less than $10^9$ $M^{-1}$.

An "anti-idiotype antibody" is an antibody that binds with the variable region domain of an immunoglobulin. In the present context, an anti-idiotype antibody binds with the variable region of an anti-interferon-ε antibody, and thus, an anti-idiotype antibody mimics an epitope of interferon-ε.

An "antibody fragment" is a portion of an antibody such as F(ab')$_2$, F(ab)$_2$, Fab', Fab, and the like. Regardless of structure, an antibody fragment binds with the same antigen that is recognized by the intact antibody. For example, an anti-interferon-ε monoclonal antibody fragment binds with an epitope of interferon-ε.

The term "antibody fragment" also includes a synthetic or a genetically engineered polypeptide that binds to a specific antigen, such as polypeptides consisting of the light chain variable region, "Fv" fragments consisting of the variable regions of the heavy and light chains, recombinant single chain polypeptide molecules in which light and heavy variable regions are connected by a peptide linker ("scFv proteins"), and minimal recognition units consisting of the amino acid residues that mimic the hypervariable region.

A "chimeric antibody" is a recombinant protein that contains the variable domains and complementary determining regions derived from a rodent antibody, while the remainder of the antibody molecule is derived from a human antibody.

"Humanized antibodies" are recombinant proteins in which murine complementarity determining regions of a monoclonal antibody have been transferred from heavy and light variable chains of the murine immunoglobulin into a human variable domain.

As used herein, a "therapeutic agent" is a molecule or atom which is conjugated to an antibody moiety to produce a conjugate which is useful for therapy. Examples of therapeutic agents include drugs, toxins, immunomodulators, chelators, boron compounds, photoactive agents or dyes, and radioisotopes.

A "detectable label" is a molecule or atom which can be conjugated to an antibody moiety to produce a molecule useful for diagnosis. Examples of detectable labels include chelators, photoactive agents, radioisotopes, fluorescent agents, paramagnetic ions, or other marker moieties.

The term "affinity tag" is used herein to denote a polypeptide segment that can be attached to a second polypeptide to provide for purification or detection of the second polypeptide or provide sites for attachment of the second polypeptide to a substrate. In principal, any peptide or protein for which an antibody or other specific binding agent is available can be used as an affinity tag. Affinity tags include a poly-histidine tract, protein A (Nilsson et al., *EMBO J.* 4:1075 (1985); Nilsson et al., *Methods Enzymol.* 198:3 (1991)), glutathione S transferase (Smith and Johnson, *Gene* 67:31 (1988)), Glu-Glu affinity tag (Grussenmeyer et al., *Proc. Natl. Acad. Sci. USA* 82:7952 (1985)), substance P, FLAG peptide (Hopp et al., *Biotechnology* 6:1204 (1988)), streptavidin binding peptide, or other antigenic epitope or binding domain. See, in general, Ford et al., *Protein Expression and Purification* 2:95 (1991). DNAs encoding affinity tags are available from commercial suppliers (e.g., Pharmacia Biotech, Piscataway, N.J.).

A "naked antibody" is an entire antibody, as opposed to an antibody fragment, which is not conjugated with a therapeutic agent. Naked antibodies include both polyclonal and monoclonal antibodies, as well as certain recombinant antibodies, such as chimeric and humanized antibodies.

As used herein, the term "antibody component" includes both an entire antibody and an antibody fragment.

An "immunoconjugate" is a conjugate of an antibody component with a therapeutic agent or a detectable label.

As used herein, the term "antibody fusion protein" refers to a recombinant molecule that comprises an antibody component and a therapeutic agent. Examples of therapeutic agents suitable for such fusion proteins include immunomodulators ("antibody-immunomodulator fusion protein") and toxins ("antibody-toxin fusion protein").

A "tumor associated antigen" is a protein normally not expressed, or expressed at lower levels, by a normal counterpart cell. Examples of tumor associated antigens include alpha-fetoprotein, carcinoembryonic antigen, and Her-2/neu. Many other illustrations of tumor associated antigens are known to those of skill in the art. See, for example, Urban et al., *Ann. Rev. Immunol.* 10:617 (1992).

As used herein, an "infectious agent" denotes both microbes and parasites. A "microbe" includes viruses, bacteria, rickettsia, mycoplasma, protozoa, fungi and like microorganisms. A "parasite" denotes infectious, generally microscopic or very small multicellular invertebrates, or ova or juvenile forms thereof, which are susceptible to immune-mediated clearance or lytic or phagocytic destruction, such as malarial parasites, spirochetes, and the like.

An "infectious agent antigen" is an antigen associated with an infectious agent.

A "target polypeptide" or a "target peptide" is an amino acid sequence that comprises at least one epitope, and that is expressed on a target cell, such as a tumor cell, or a cell that carries an infectious agent antigen. T cells recognize peptide epitopes presented by a major histocompatibility complex molecule to a target polypeptide or target peptide and typically lyse the target cell or recruit other immune cells to the site of the target cell, thereby killing the target cell.

An "antigenic peptide" is a peptide which will bind a major histocompatibility complex molecule to form an MHC-peptide complex which is recognized by a T cell, thereby inducing a cytotoxic lymphocyte response upon presentation to the T cell. Thus, antigenic peptides are capable of binding to an appropriate major histocompatibility complex molecule and inducing a cytotoxic T cells response, such as cell lysis or specific cytokine release against the target cell which binds or expresses the antigen. The antigenic peptide can be bound in the context of a class I or class II major histocompatibility complex molecule, on an antigen presenting cell or on a target cell.

In eukaryotes, RNA polymerase II catalyzes the transcription of a structural gene to produce mRNA. A nucleic acid molecule can be designed to contain an RNA polymerase II template in which the RNA transcript has a sequence that is complementary to that of a specific mRNA. The RNA transcript is termed an "anti-sense RNA" and a nucleic acid molecule that encodes the anti-sense RNA is termed an "anti-sense gene." Anti-sense RNA molecules are capable of binding to mRNA molecules, resulting in an inhibition of mRNA translation.

An "anti-sense oligonucleotide specific for interferon-ε" or an "interferon-ε anti-sense oligonucleotide" is an oligonucleotide having a sequence (a) capable of forming a stable triplex with a portion of the interferon-ε gene, or (b) capable of forming a stable duplex with a portion of an mRNA transcript of the interferon-ε, gene.

A "ribozyme" is a nucleic acid molecule that contains a catalytic center. The term includes RNA enzymes, self-splicing RNAs, self-cleaving RNAs, and nucleic acid molecules that perform these catalytic functions. A nucleic acid molecule that encodes a ribozyme is termed a "ribozyme gene."

An "external guide sequence" is a nucleic acid molecule that directs the endogenous ribozyme, RNase P, to a particular species of intracellular mRNA, resulting in the cleavage of the mRNA by RNase P. A nucleic acid molecule that encodes an external guide sequence is termed an "external guide sequence gene."

The term "variant human interferon-ε gene" refers to nucleic acid molecules that encode a polypeptide having an amino acid sequence that is a modification of SEQ ID NO:2. Such variants include naturally-occurring polymorphisms of interferon-ε genes, as well as synthetic genes that contain conservative amino acid substitutions of the amino acid sequence of SEQ ID NO:2. Additional variant forms of interferon-ε genes are nucleic acid molecules that contain insertions or deletions of the nucleotide sequences described herein. A variant interferon-ε gene can be identified by determining whether the gene hybridizes with a nucleic acid molecule having the nucleotide sequence of SEQ ID NO:1, or its complement, under stringent conditions.

Similarly, the term "variant murine interferon-ε gene" refers to nucleic acid molecules that encode a polypeptide having an amino acid sequence that is a modification of SEQ ID NO:24. A variant murine interferon-ε gene can be identified by determining whether the gene hybridizes with a nucleic acid molecule having the nucleotide sequence of SEQ ID NO:23, or its complement, under stringent conditions.

Alternatively, variant interferon-ε genes can be identified by sequence comparison. Two amino acid sequences have "100% amino acid sequence identity" if the amino acid residues of the two amino acid sequences are the same when aligned for maximal correspondence. Similarly, two nucleotide sequences have "100% nucleotide sequence identity" if the nucleotide residues of the two nucleotide sequences are the same when aligned for maximal correspondence. Sequence comparisons can be performed using standard software programs such as those included in the LASERGENE bioinformatics computing suite, which is produced by DNASTAR (Madison, Wis.). Other methods for comparing two nucleotide or amino acid sequences by determining optimal alignment are well-known to those of skill in the art (see, for example, Peruski and Peruski, *The Internet and the New Biology: Tools for Genomic and Molecular Research* (ASM Press, Inc. 1997), Wu et al. (eds.), "Information Superhighway and Computer Databases of Nucleic Acids and Proteins," in *Methods in Gene Biotechnology*, pages 123–151 (CRC Press, Inc. 1997), and Bishop (ed.), *Guide to Human Genome Computing*, 2nd Edition (Academic Press, Inc. 1998)). Particular methods for determining sequence identity are described below.

Regardless of the particular method used to identify a variant interferon-ε gene or variant interferon-ε polypeptide, a variant gene or polypeptide encoded by a variant gene is functionally characterized by either its anti-viral or anti-proliferative activities, or by the ability to bind specifically to an anti-interferon-ε antibody.

The term "allelic variant" is used herein to denote any of two or more alternative forms of a gene occupying the same chromosomal locus. Allelic variation arises naturally through mutation, and may result in phenotypic polymorphism within populations. Gene mutations can be silent (no change in the encoded polypeptide) or may encode polypeptides having altered amino acid sequence. Zifne (SEQ ID NO:2) and Zifne-1 (SEQ ID NO.5) are examples of the latter form of allelic variant. The term allelic variant is also used herein to denote a protein encoded by an allelic variant of a gene.

The term "ortholog" denotes a polypeptide or protein obtained from one species that is the functional counterpart of a polypeptide or protein from a different species. Sequence differences among orthologs are the result of speciation.

"Paralogs" are distinct but structurally related proteins made by an organism. Paralogs are believed to arise through gene duplication. For example, α-globin, β-globin, and myoglobin are paralogs of each other.

The present invention includes functional fragments of interferon-ε genes. Within the context of this invention, a "functional fragment" of an interferon-ε gene refers to a nucleic acid molecule that encodes a portion of an interferon-ε polypeptide which either (1) possesses an anti-viral or anti-proliferative activity, or (2) specifically binds with an anti-interferon-ε antibody. For example, a functional fragment of a human interferon-ε gene described herein comprises a portion of the nucleotide sequence of SEQ ID NO:2 or SEQ ID NO:5, and encodes a polypeptide having either an anti-viral or anti-proliferative activity. Similarly, a functional fragment of a murine interferon-ε gene comprises a portion of the nucleotide sequence of SEQ ID NO:23, and encodes a polypeptide having either an anti-viral or anti-proliferative activity.

Due to the imprecision of standard analytical methods, molecular weights and lengths of polymers are understood to be approximate values. When such a value is expressed as "about" X or "approximately" X, the stated value of X will be understood to be accurate to ±10%.

3. Production of Human and Murine Interferon-ε Genes

Nucleic acid molecules encoding a human interferon-ε gene can be obtained by screening a human cDNA or genomic library using polynucleotide probes based upon SEQ ID NO:1 or SEQ ID NO:4. Similarly, nucleic acid molecules encoding a murine interferon-ε gene can be obtained by screening a murine cDNA or genomic library using polynucleotide probes based upon SEQ ID NO:23. These techniques are standard and well-established.

As an illustration, a nucleic acid molecule that encodes a human interferon-ε gene can be isolated from a human cDNA library. In this case, the first step would be to prepare the cDNA library by isolating RNA from coronary artery smooth muscle tissue, placental tissue, uterine tissue, human umbilical vein endothelial cells, or tracheal tissue, using methods well-known to those of skill in the art. In general, RNA isolation techniques must provide a method for breaking cells, a means of inhibiting RNase-directed degradation of RNA, and a method of separating RNA from DNA, protein, and polysaccharide contaminants. For example, total RNA can be isolated by freezing tissue in liquid nitrogen, grinding the frozen tissue with a mortar and pestle to lyse the cells, extracting the ground tissue with a solution of phenol/chloroform to remove proteins, and separating RNA from the remaining impurities by selective precipitation with lithium chloride (see, for example, Ausubel el al. (eds.), *Short Protocols in Molecular Biology*, 3$^{rd}$ Edition, pages 4-1 to 4-6 (John Wiley & Sons 1995) ["Ausubel (1995)"]; Wu et al., *Methods in Gene Biotechnology, pages 33–41* (CRC Press, Inc. 1997) ["Wu (1997)"]). Alternatively, total RNA can be isolated from coronary artery smooth muscle tissue (or, placental tissue, uterine tissue, or tracheal tissue) by extracting ground tissue with guanidinium isothiocyanate, extracting with organic solvents, and separating RNA from contaminants using differential centrifugation (see, for example, Chirgwin et al., *Biochemistry* 18:52 (1979); Ausubel (1995) at pages 4-1 to 4-6; Wu (1997) at pages 33–41).

In order to construct a cDNA library, poly(A)$^+$ RNA must be isolated from a total RNA preparation. Poly(A)$^+$ RNA can be isolated from total RNA using the standard technique of oligo(dT)-cellulose chromatography (see, for example, Aviv and Leder, *Proc. Nat'l Acad. Sci. USA* 69:1408 (1972); Ausubel (1995) at pages 4-11 to 4-12).

Double-stranded cDNA molecules are synthesized from poly(A)$^+$ RNA using techniques well-known to those in the art. (see, for example, Wu (1997) at pages 41–46). Moreover, commercially available kits can be used to synthesize double-stranded cDNA molecules. For example, such kits are available from Life Technologies, Inc. (Gaithersburg, Md.), CLONTECH Laboratories, Inc. (Palo Alto, Calif.), Promega Corporation (Madison, Wis.) and STRATAGENE (La Jolla, Calif.).

Various cloning vectors are appropriate for the construction of a cDNA library. For example, a cDNA library can be prepared in a vector derived from bacteriophage, such as a λgt10 vector. See, for example, Huynh et al., "Constructing and Screening cDNA Libraries in λgt10 and λgt11," in *DNA Cloning: A Practical Approach Vol. I*, Glover (ed.), page 49 (IRL Press, 1985); Wu (1997) at pages 47–52.

Alternatively, double-stranded cDNA molecules can be inserted into a plasmid vector, such as a PBLUESCRIPT vector (STRATAGENE; La Jolla, Calif.), a LAMDAGEM-4 (Promega Corp.) or other commercially available vectors. Suitable cloning vectors also can be obtained from the American Type Culture Collection (Manassas, Va.).

To amplify the cloned cDNA molecules, the cDNA library is inserted into a prokaryotic host, using standard techniques. For example, a cDNA library can be introduced into competent *E. coli* DH5 cells, which can be obtained, for example, from Life Technologies, Inc. (Gaithersburg, Md.).

A genomic library can be prepared by means well-known in the art (see, for example, Ausubel (1995) at pages 5-1 to 5-6; Wu (1997) at pages 307–327). Genomic DNA can be isolated by lysing tissue with the detergent Sarkosyl, digesting the lysate with proteinase K, clearing insoluble debris from the lysate by centrifugation, precipitating nucleic acid from the lysate using isopropanol, and purifying resuspended DNA on a cesium chloride density gradient.

DNA fragments that are suitable for the production of a genomic library can be obtained by the random shearing of genomic DNA or by the partial digestion of genomic DNA with restriction endonucleases. Genomic DNA fragments can be inserted into a vector, such as a bacteriophage or cosmid vector, in accordance with conventional techniques, such as the use of restriction enzyme digestion to provide appropriate termini, the use of alkaline phosphatase treatment to avoid undesirable joining of DNA molecules, and ligation with appropriate ligases. Techniques for such manipulation are well-known in the art (see, for example, Augubel (1995) at pages 5-1 to 5-6; Wu (1997) at pages 307–327).

Nucleic acid molecules that encode an interferon-ε gene can also be obtained using the polymerase chain reaction (PCR) with oligonucleotide primers having nucleotide sequences that are based upon the nucleotide sequences of the interferon-ε genes, as described herein. General methods for screening libraries with PCR are provided by, for example, Yu et al., "Use of the Polymerase Chain Reaction to Screen Phage Libraries," in *Methods in Molecular Biology, Vol. 15: PCR Protocols: Current Methods and Applications*, White (ed.), pages 211–215 (Humana Press, Inc. 1993). Moreover, techniques for using PCR to isolate related genes are described by, for example, Preston, "Use of Degenerate Oligonucleotide Primers and the Polymerase Chain Reaction to Clone Gene Family Members," in *Methods in Molecular Biology, Vol. 15: PCR Protocols: Current Methods and Applications*, White (ed.), pages 317–337 (Humana Press, Inc. 1993).

Alternatively, genomic libraries can be obtained from commercial sources such as Research Genetics (Huntsville, Ala.) and the American Type Culture Collection (Manassas, Va.).

A library containing cDNA or genomic clones can be screened with one or more polynucleotide probes based upon SEQ ID NO:1 or SEQ ID NO:23, using standard methods (see, for example, Ausubel (1995) at pages 6-1 to 6-11).

Anti-interferon-ε antibodies, produced as described below, can also be used to isolate DNA sequences that encode interferon-ε genes from cDNA libraries. For example, the antibodies can be used to screen λgt11 expression libraries, or the antibodies can be used for immunoscreening following hybrid selection and translation (see, for example, Ausubel (1995) at pages 6-12 to 6-16; Margolis et al., "Screening λexpression libraries with antibody and protein probes," in *DNA Cloning 2: Expression Systems, 2nd Edition*, Glover et al. (eds.), pages 1–14 (Oxford University Press 1995)).

As an alternative, an interferon-ε gene can be obtained by synthesizing nucleic acid molecules using mutually priming long oligonucleotides and the nucleotide sequences described herein (see, for example, Ausubel (1995) at pages 8-8 to 8-9). Established techniques using the polymerase chain reaction provide the ability to synthesize DNA molecules at least two kilobases in length (Adang et al., *Plant Molec. Biol.* 21:1131 (1993), Bambot et al., *PCR Methods and Applications* 2:266 (1993), Dillon et al., "Use of the Polymerase Chain Reaction for the Rapid Construction of Synthetic Genes," in *Methods in Molecular Biology, Vol. 15: PCR Protocols: Current Methods and Applications,* White (ed.), pages 263–268, (Humana Press, Inc. 1993), and Holowachuk et al., PCR Methods Appl. 4:299 (1995)).

The nucleic acid molecules of the present invention can also be synthesized with "gene machines" using protocols such as the phosphoramidite method. If chemically-synthesized double stranded DNA is required for an application such as the synthesis of a gene or a gene fragment, then each complementary strand is made separately. The production of short genes (60 to 80 base pairs) is technically straightforward and can be accomplished by synthesizing the complementary strands and then annealing them. For the production of longer genes (>300 base pairs), however, special strategies may be required, because the coupling efficiency of each cycle during chemical DNA synthesis is seldom 100%. To overcome this problem, synthetic genes (double-stranded) are assembled in modular form from single-stranded fragments that are from 20 to 100 nucleotides in length. For reviews on polynucleotide synthesis, see, for example, Glick and Pasternak, *Molecular Biotechnology, Principles and Applications of Recombinant DNA* (ASM Press 1994), Itakura et al., *Annu. Rev. Biochem.* 53:323 (1984), and Climie et al., *Proc. Nat'l Acad. Sci. USA* 87:633 (1990).

The sequence of an interferon-ε cDNA or interferon-ε genomic fragment can be determined using standard methods. Moreover, the identification of genomic fragments containing an interferon-ε promoter or regulatory element can be achieved using well-established techniques, such as deletion analysis (see, generally, Ausubel (1995)).

As an illustration, SEQ ID NO:23 is a nucleotide sequence of a genomic fragment that includes murine interferon-ε encoding sequences, as well as sequences that flank the 5' and 3' ends of the murine interferon-ε gene. A nucleic acid molecule comprising the nucleotide sequence of nucleotides 1 to 778 of SEQ ID NO:23 contains murine interferon-ε regulatory sequences, including at least one regulatory element and a core promoter. Standard techniques, such as deletion analysis, can be used to flier define these regulatory sequences.

Cloning of 5' flanking sequences also facilitates production of interferon-ε proteins by "gene activation," following the methods disclosed in U.S. Pat. No. 5,641,670. Briefly, expression of an endogenous interferon-ε gene in a cell is altered by introducing into the interferon-ε locus a DNA construct comprising at least a targeting sequence, a regulatory sequence, an exon, and an unpaired splice donor site. The targeting sequence is an interferon-ε 5' non-coding sequence that permits homologous recombination of the construct with the endogenous interferon-ε locus, whereby the sequences within the construct become operably linked with the endogenous interferon-ε coding sequence. In this way, an endogenous interferon-ε promoter can be replaced or supplemented with other regulatory sequences to provide enhanced, tissue-specific, or otherwise regulated expression.

4. Production of Interferon-ε Gene Variants

The present invention provides a variety of nucleic acid molecules, including DNA and RNA molecules, that encode the interferon-ε polypeptides disclosed herein. Those skilled in the art will readily recognize that, in view of the degeneracy of the genetic code, considerable sequence variation is possible among these polynucleotide molecules. SEQ ID NO:3 and SEQ ID NO:6 are degenerate nucleotide sequences that encompass all nucleic acid molecules that encode the interferon-ε polypeptides of SEQ ID NO:2, and SEQ ID NO:5, respectively. Those skilled in the art will recognize that the degenerate sequences of SEQ ID NO:3 and SEQ ID NO:6 also provide all RNA sequences encoding SEQ ID NO:2 and SEQ ID NO:5, respectively, by substituting U for T. Thus, the present invention contemplates interferon-ε polypeptide-encoding nucleic acid molecules comprising nucleotide 454 to nucleotide 1077 of SEQ ID NOs: 1 and 4, and their RNA equivalents.

Similarly, SEQ ID NO:25 is a degenerate nucleotide sequence that encodes the murine interferon-ε polypeptide (SEQ ID NO:24). The present invention includes murine interferon-ε polypeptide-encoding nucleic acid molecules comprising nucleotide 779 to nucleotide 1354 of SEQ ID NO:23, and their RNA equivalents.

Table 1 sets forth the one-letter codes used within SEQ ID NOs:3, 6, and 25 to denote degenerate nucleotide positions. "Resolutions" are the nucleotides denoted by a code letter. "Complement" indicates the code for the complementary nucleotide(s). For example, the code Y denotes either C or T, and its complement R denotes A or G, A being complementary to T, and G being complementary to C.

TABLE 1

| Nucleotide | Resolution | Complement | Resolution |
|---|---|---|---|
| A | A | T | T |
| C | C | G | G |
| G | G | C | C |
| T | T | A | A |
| R | A\|G | Y | C\|T |
| Y | C\|T | R | A\|G |
| M | A\|C | K | G\|T |
| K | G\|T | M | A\|C |
| S | C\|G | S | C\|G |
| W | A\|T | W | A\|T |
| H | A\|C\|T | D | A\|G\|T |
| B | C\|G\|T | V | A\|C\|G |
| V | A\|C\|G | B | C\|G\|T |
| D | A\|G\|T | H | A\|C\|T |
| N | A\|C\|G\|T | N | A\|C\|G\|T |

The degenerate codons used in SEQ ID NOs:3, 6, and 25, encompassing all possible codons for a given amino acid, are set forth in Table 2.

TABLE 2

| Amino Acid | One Letter Code | Codons | Degenerate Codon |
|---|---|---|---|
| Cys | C | TGC TGT | TGY |
| Ser | S | AGC AGT TCA TCC TCG TCT | WSN |
| Thr | T | ACA ACC ACG ACT | ACN |
| Pro | P | CCA CCC CCG CCT | CCN |

TABLE 2-continued

| Amino Acid | One Letter Code | Codons | Degenerate Codon |
|---|---|---|---|
| Ala | A | GCA GCC GCG GCT | GCN |
| Gly | G | GGA GGC GGG GGT | GGN |
| Asn | N | AAC AAT | AAY |
| Asp | D | GAC GAT | GAY |
| Glu | E | GAA GAG | GAR |
| Gln | Q | CAA CAG | CAR |
| His | H | CAC CAT | CAY |
| Arg | R | AGA AGG CGA CGC CGG CGT | MGN |
| Lys | K | AAA AAG | AAR |
| Met | M | ATG | ATG |
| Ile | I | ATA ATC ATT | ATH |
| Leu | L | CTA CTC CTG CTT TTA TTG | YTN |
| Val | V | GTA GTC GTG GTT | GTN |
| Phe | F | TTC TTT | TTY |
| Tyr | Y | TAC TAT | TAY |
| Trp | W | TGG | TGG |
| Ter | . | TAA TAG TGA | TRR |
| Asn\|Asp | B | | RAY |
| Glu\|Gln | Z | | SAR |
| Any | X | | NNN |

One of ordinary skill in the art will appreciate that some ambiguity is introduced in determining a degenerate codon, representative of all possible codons encoding an amino acid. For example, the degenerate codon for serine (WSN) can, in some circumstances, encode arginine (AGR), and the degenerate codon for arginine (MGN) can, in some circumstances, encode serine (AGY). A similar relationship exists between codons encoding phenylalanine and leucine. Thus, some polynucleotides encompassed by the degenerate sequence may encode variant amino acid sequences, but one of ordinary skill in the art can easily identify such variant sequences by reference to the amino acid sequence of SEQ ID NO:2, SEQ ID NO:5, or SEQ ID NO:24. Variant sequences can be readily tested for functionality as described herein.

Different species can exhibit "preferential codon usage." In general, see, Grantham et al., *Nuc. Acids Res.* 8:1893 (1980), Haas et al. *Curr. Biol.* 6:315 (1996), Wain-Hobson et al, *Gene* 13:355 (1981), Grosjean and Fiers, *Gene* 18:199 (1982), Holm, *Nuc. Acids Res.* 14:3075 (1986), Ikemura, *J. Mol. Biol.* 158:573 (1982), Sharp and Matassi, *Curr. Opin. Genet. Dev.* 4:851 (1994), Kane, *Curr. Opin. Biotechnol.* 6:494 (1995), and Makrides, *Microbiol. Rev.* 60:512 (1996). As used herein, the term "preferential codon usage" or "preferential codons" is a term of art referring to protein translation codons that are most frequently used in cells of a certain species, thus favoring one or a few representatives of the possible codons encoding each amino acid (See Table 2). For example, the amino acid Threonine (Thr) may be encoded by ACA, ACC, ACG, or ACT, but in mammalian cells ACC is the most commonly used codon; in other species, for example, insect cells, yeast, viruses or bacteria, different Thr codons may be preferential. Preferential codons for a particular species can be introduced into the polynucleotides of the present invention by a variety of methods known in the art. Introduction of preferential codon sequences into recombinant DNA can, for example, enhance production of the protein by making protein translation more efficient within a particular cell type or species. Therefore, the degenerate codon sequences disclosed in SEQ ID NOs:3, 6, and 25 serve as templates for optimizing expression of polynucleotides in various cell types and species commonly used in the art and disclosed herein. Sequences containing preferential codons can be tested and optimized for expression in various species, and tested for functionality as disclosed herein.

The present invention further provides variant polypeptides and nucleic acid molecules that represent counterparts from other species (orthologs). These species include, but are not limited to mammalian, avian, amphibian, reptile, fish, insect and other vertebrate and invertebrate species. Of particular interest are interferon-ε polypeptides from other mammalian species, including murine, porcine, ovine, bovine, canine, feline, equine, and other primate polypeptides. Orthologs of human interferon-ε can be cloned using information and compositions provided by the present invention in combination with conventional cloning techniques. For example, a cDNA can be cloned using mRNA obtained from a tissue or cell type that expresses interferon-ε as disclosed herein. Suitable sources of mRNA can be identified by probing northern blots with probes designed from the sequences disclosed herein, and a library can be prepared from mRNA of a positive tissue or cell line. An interferon-ε-encoding cDNA can then be isolated by a variety of methods, such as by probing with a complete or partial interferon-ε cDNA or with one or more sets of degenerate probes based on the disclosed sequences. A cDNA can also be cloned using the polymerase chain reaction with primers designed from the representative interferon-ε sequences disclosed herein.

Example 6 illustrates a method used to obtain the murine ortholog of human interferon-ε. As described in Example 4, Southern analysis with a human interferon-ε probe revealed hybridizing fragments in human, murine, monkey, canine, and bovine genomic DNA. Accordingly, the present invention includes monkey, canine, and bovine interferon-ε genes, which can be isolated as described for the isolation of the murine ortholog.

Those skilled in the art will recognize that the sequence disclosed in SEQ ID NO:1 represents a single allele of human interferon-ε, and that allelic variation and alternative splicing are expected to occur. Allelic variants of this sequence can be cloned by probing cDNA or genomic libraries from different individuals according to standard procedures. Allelic variants of the nucleotide sequence shown in SEQ ID NO:1 or SEQ ID NO:4, including those containing silent mutations and those in which mutations result in amino acid sequence changes, are within the scope of the present invention, as are proteins which are allelic variants of SEQ ID NOs:2 and 5. cDNA molecules generated from alternatively spliced mRNAs, which retain the properties of the interferon-ε polypeptide are included within the scope of the present invention, as are polypeptides encoded by such cDNAs and mRNAs. Allelic variants and splice variants of these sequences can be cloned by probing cDNA or genomic libraries from different individuals or tissues according to standard procedures known in the art.

Within preferred embodiments of the invention, isolated nucleic acid molecules that encode human interferon-ε can hybridize to nucleic acid molecules having the nucleotide sequence of SEQ ID NO:1, or a sequence complementary thereto, under "stringent conditions." In general, stringent conditions are selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe.

As an illustration, a nucleic acid molecule encoding a variant interferon-ε polypeptide can be hybridized with a nucleic acid molecule having the nucleotide sequence of SEQ ID NO:1 (or its complement) at 42° C. overnight in a solution comprising 50% formanide, 5×SSC (1×SSC: 0.15 M sodium chloride and 15 mM sodium citrate), 50 mM sodium phosphate (pH 7.6), 5×Denhardt's solution (100× Denhardt's solution: 2% (w/v) Ficoll 400, 2% (w/v) polyvinylpyrrolidone, and 2% (w/v) bovine serum albumin), 10% dextran sulfate, and 20 μg/ml denatured, sheared salmon sperm DNA. One of skill in the art can devise variations of these hybridization conditions. For example, the hybridization mixture can be incubated at a higher temperature, such as about 65° C., in a solution that does not contain formamide. Moreover, premixed hybridization solutions are available (e.g., EXPRESSHYB Hybridization Solution from CLONTECH Laboratories, Inc.), and hybridization can be performed according to the manufacturer's instructions.

Following hybridization, the nucleic acid molecules can be washed to remove non-hybridized nucleic acid molecules under stringent conditions, or under highly stringent conditions. Typical stringent washing conditions include washing in a solution of 0.5×–2×SSC with 0.1% sodium dodecyl sulfate (SDS) at 55–65° C. That is, nucleic acid molecules encoding a variant interferon-ε polypeptide hybridize with a nucleic acid molecule having the nucleotide sequence of SEQ ID NO:1 (or its complement) under stringent washing conditions, in which the wash stringency is equivalent to 0.5×–2×SSC with 0.1% SDS at 55–65° C., including 0.5× SSC with 0.1% SDS at 55° C., or 2×SSC with 0.1% SDS at 65° C. One of skill in the art can readily devise equivalent conditions, for example, by substituting SSPE for SSC in the wash solution.

Typical highly stringent washing conditions include washing in a solution of 0.1×–0.2×SSC with 0.1% sodium dodecyl sulfate (SDS) at 50–65° C. In other words, nucleic acid molecules encoding a variant interferon-ε polypeptide hybridize with a nucleic acid molecule having the nucleotide sequence of SEQ ID NO:1 (or its complement) under highly stringent washing conditions, in which the wash stringency is equivalent to 0.1×–0.2×SSC with 0.1% SDS at 50–65° C., including 0.1×SSC with 0.1% SDS at 50° C., or 0.2×SSC with 0.1% SDS at 65° C.

The present invention also provides isolated interferon-ε polypeptides that have a substantially similar sequence identity to the polypeptides of SEQ ID NO:2, SEQ ID NO:5, or their orthologs. The term "substantially similar sequence identity" is used herein to denote polypeptides having at least 70%, at least 80%, at least 90%, at least 95% or greater than 95% sequence identity to the sequences shown in SEQ ID NO:2, SEQ ID NO:5, or their orthologs.

The present invention also contemplates interferon-ε variant nucleic acid molecules that can be identified using two criteria: a determination of the similarity between the encoded polypeptide with the amino acid sequence of SEQ ID NO:2, and a hybridization assay, as described above. Such interferon-ε variants include nucleic acid molecules (1) that hybridize with a nucleic acid molecule having the nucleotide sequence of SEQ ID NO:1 (or its complement) under stringent washing conditions, in which the wash stringency is equivalent to 0.5×–2×SSC with 0.1% SDS at 55–65° C., and (2) that encode a polypeptide having at least 70%, at least 80%, at least 90%, at least 95% or greater than 95% sequence identity to the amino acid sequence of SEQ ID NO:2. Alternatively, interferon-ε variants can be characterized as nucleic acid molecules (1) that hybridize with a nucleic acid molecule having the nucleotide sequence of SEQ ID NO:1 (or its complement) under highly stringent washing conditions, in which the wash stringency is equivalent to 0.1×–0.2×SSC with 0.1% SDS at 50–65° C., and (2) that encode a polypeptide having at least 70%, at least 80%, at least 90%, at least 95% or greater than 95% sequence identity to the amino acid sequence of SEQ ID NO:2.

The present invention also contemplates human interferon-ε variant nucleic acid molecules identified by at least one of hybridization analysis and sequence identity determination, with reference to SEQ ID NOs:4 and 5. The present invention further includes murine interferon-ε variant nucleic acid molecules identified by at least one of hybridization analysis and sequence identity determination, with reference to SEQ ID NOs:23 and 24. For example, using the approach discussed above, murine interferon-ε variant nucleic acid molecules can be identified using at least one of three criteria: (1) hybridization with a nucleic acid molecule having the nucleotide sequence of SEQ ID NO:23 (or its complement) under stringent washing conditions, in which the wash stringency is equivalent to 0.5×–2×SSC with 0.1% SDS at 55–65° C., (2) hybridization with a nucleic acid molecule having the nucleotide sequence of SEQ ID NO:23 (or its complement) under highly stringent washing conditions, in which the wash stringency is equivalent to 0.1×–0.2×SSC with 0.1% SDS at 50–65° C., and (3) an amino acid percent identity that is at least 70%, at least 80%, at least 90%, at least 95% or greater than 95% sequence identity to the amino acid sequence of SEQ ID NO:24.

Percent sequence identity is determined by conventional methods. See, for example, Altschul et al., *Bull. Math. Bio.* 48:603 (1986), and Henikoff and Henikoff, *Proc. Natl. Acad. Sci. USA* 89:10915 (1992). Briefly, two amino acid sequences are aligned to optimize the alignment scores using a gap opening penalty of 10, a gap extension penalty of 1, and the "BLOSUM 62" scoring matrix of Henikoff and Henikoff (ibid.) as shown in Table 3 (amino acids are indicated by the standard one-letter codes). The percent identity is then calculated as: ([Total number of identical matches]/[length of the longer sequence plus the number of gaps introduced into the longer sequence in order to align the two sequences])(100).

TABLE 3

|   | A | R | N | D | C | Q | E | G | H | I | L | K | M | F | P | S | T | W | Y | V |
|---|---|---|---|---|---|---|---|---|---|---|---|---|---|---|---|---|---|---|---|---|
| A | 4 | | | | | | | | | | | | | | | | | | | |
| R | -1 | 5 | | | | | | | | | | | | | | | | | | |
| N | -2 | 0 | 6 | | | | | | | | | | | | | | | | | |
| D | -2 | -2 | 1 | 6 | | | | | | | | | | | | | | | | |
| C | 0 | -3 | -3 | -3 | 9 | | | | | | | | | | | | | | | |
| Q | -1 | 1 | 0 | 0 | .3 | 5 | | | | | | | | | | | | | | |
| E | -1 | 0 | 0 | 2 | -4 | 2 | 5 | | | | | | | | | | | | | |
| G | 0 | -2 | 0 | -1 | -3 | -2 | -2 | 6 | | | | | | | | | | | | |
| H | -2 | 0 | 1 | -1 | -3 | 0 | 0 | -2 | 8 | | | | | | | | | | | |
| I | -1 | -3 | -3 | -3 | -1 | -3 | -3 | -4 | -3 | 4 | | | | | | | | | | |
| L | -1 | -2 | -3 | -4 | -1 | -2 | -3 | -4 | -3 | 2 | 4 | | | | | | | | | |
| K | -1 | 2 | 0 | -1 | -3 | 1 | 1 | -2 | -1 | -3 | -2 | 5 | | | | | | | | |
| M | -1 | -1 | -2 | -3 | -1 | 0 | -2 | -3 | -2 | 1 | 2 | -1 | 5 | | | | | | | |
| F | -2 | -3 | -3 | -3 | -2 | -3 | -3 | -3 | -1 | 0 | 0 | -3 | 0 | 6 | | | | | | |
| P | -1 | -2 | -2 | -1 | -3 | -1 | -1 | -2 | -2 | -3 | -3 | -1 | -2 | -4 | 7 | | | | | |
| S | 1 | -1 | 1 | 0 | -1 | 0 | 0 | 0 | -1 | -2 | -2 | 0 | -1 | -2 | -1 | 4 | | | | |
| T | 0 | -1 | 0 | -1 | -1 | -1 | -1 | -2 | -2 | -1 | -1 | -1 | -1 | -2 | -1 | 1 | 5 | | | |
| W | -3 | -3 | -4 | -4 | -2 | -2 | -3 | -2 | -2 | -3 | -2 | -3 | -1 | 1 | -4 | -3 | -2 | 11 | | |
| Y | -2 | -2 | -2 | -3 | -2 | -1 | -2 | -3 | 2 | -1 | -1 | -2 | -1 | 3 | -3 | -2 | -2 | 2 | 7 | |
| V | 0 | -3 | -3 | -3 | -1 | -2 | -2 | -3 | -3 | 3 | 1 | -2 | 1 | -1 | -2 | -2 | 0 | -3 | -1 | 4 |

Those skilled in the art appreciate that there are many established algorithms available to align two amino acid sequences. The "FASTA" similarity search algorithm of Pearson and Lipman is a suitable protein alignment method for examining the level of identity shared by an amino acid sequence disclosed herein and the amino acid sequence of a putative interferon-ε variant. The FASTA algorithm is described by Pearson and Lipman, Proc. Nat'l Acad. Sci. USA 85:2444 (1988), and by Pearson, Meth. Enzymol. 183:63 (1990). Briefly, FASTA first characterizes sequence similarity by identifying regions shared by the query sequence (e.g., SEQ ID NO:2) and a test sequence that have either the highest density of identities (if the ktup variable is 1) or pairs of identities (if ktup=2), without considering conservative amino acid substitutions, insertions, or deletions. The ten regions with the highest density of identities are then rescored by comparing the similarity of all paired amino acids using an amino acid substitution matrix, and the ends of the regions are "trimmed" to include only those residues that contribute to the highest score. If there are several regions with scores greater than the "cutoff" value (calculated by a predetermined formula based upon the length of the sequence and the ktup value), then the trimmed initial regions are examined to determine whether the regions can be joined to form an approximate alignment with gaps. Finally, the highest scoring regions of the two amino acid sequences are aligned using a modification of the Needleman-Wunsch- Sellers algorithm (Needleman and Wunsch, J. Mol. Biol. 48:444 (1970); Sellers, SIAM J. Appl. Math. 26:787 (1974)), which allows for amino acid insertions and deletions. Illustrative parameters for FASTA analysis are: ktup=1, gap opening penalty=10, gap extension penalty=1, and substitution matrix=BLOSUM62. These parameters can be introduced into a FASTA program by modifying the scoring matrix file ("SMATRIX"), as explained in Appendix 2 of Pearson, Meth. Enzymol. 183:63 (1990).

FASTA can also be used to determine the sequence identity of nucleic acid molecules using a ratio as disclosed above. For nucleatide sequence comparisons, the ktup value can range between one to six, preferably from three to six, most preferably three, with other parameters set as described above.

The present invention includes nucleic acid molecules that encode a polypeptide having a conservative amino acid change, compared with the amino acid sequence of SEQ ID NO:2, SEQ ID NO:5, or SEQ ID NO:24. That is, variants can be obtained that contain one or more amino acid substitutions of SEQ ID NO:2, SEQ ID NO:5, or SEQ ID NO:24, in which an alkyl amino acid is substituted for an alkyl amino acid in an interferon-ε amino acid sequence, an aromatic amino acid is substituted for an aromatic amino acid in an interferon-ε amino acid sequence, a sulfur-containing amino acid is substituted for a sulfur-containing amino acid in an interferon-ε amino acid sequence, a hydroxy-containing amino acid is substituted for a hydroxy-containing amino acid in an interferon-ε amino acid sequence, an acidic amino acid is substituted for an acidic amino acid in an interferon-ε amino acid sequence, a basic amino acid is substituted for a basic amino acid in an interferon-ε amino acid sequence, or a dibasic monocarboxylic amino acid is substituted for a dibasic monocarboxylic amino acid in an interferon-ε amino acid sequence.

Among the common amino acids, for example, a "conservative amino acid substitution" is illustrated by a substitution among amino acids within each of the following groups: (1) glycine, alanine, valine, leucine, and isoleucine, (2) phenylalanine, tyrosine, and tryptophan, (3) serine and threonine, (4) aspartate and glutamate, (5) glutamine and asparagine, and (6) lysine, arginine and histidine. For example, variant interferon-ε polypeptides that have an amino acid sequence that differs from either SEQ ID NO:2 or SEQ ID NO:5 can be obtained by substituting a threonine residue for $Ser^{38}$, by substituting a valine residue for $Ile^{80}$, by substituting an aspartate residue for $Glu^{107}$, or by substituting a valine residue for $Ile^{167}$. Additional variants can be obtained by producing polypeptides having two or more of these amino acid substitutions. Variants of the murine interferon-ε polypeptide can also be obtained by introducing conservative amino acid substitutions into the amino acid sequence of SEQ ID NO;24.

The BLOSUM62 table is an amino acid substitution matrix derived from about 2,000 local multiple alignments of protein sequence segments, representing highly conserved regions of more than 500 groups of related proteins (Henikoff and Henikoff, Proc. Nat'l Acad. Sci. USA 89:10915 (1992)). Accordingly, the BLOSUM62 substitution frequencies can be used to define conservative amino acid substitutions that may be introduced into the amino acid sequences of the present invention. Although it is possible to design amino acid substitutions based solely upon chemical properties (as discussed above), the language "conservative amino acid substitution" preferably refers to a substitution represented by a BLOSUM62 value of greater than −1. For example, an amino acid substitution is conservative if the substitution is characterized by a BLOSUM62 value of 0, 1, 2, or 3. According to this system, preferred conservative amino acid substitutions are characterized by a BLOSUM62 value of at least 1 (e.g., 1, 2 or 3), while more preferred conservative amino acid substitutions are characterized by a BLOSUM62 value of at least 2 (e.g., 2 or 3).

Particular variants of human or murine interferon-ε are characterized by having at least 70%, at least 80%, at least 90%, at least 95% or greater than 95% sequence identity to the corresponding human (i.e., SEQ ID NOs; 2 or 5) or murine (i.e., SEQ ID NO:24) amino acid sequences, wherein the variation in amino acid sequence is due to one or more conservative amino acid substitutions.

Conservative amino acid changes in an interferon-ε gene can be introduced by substituting nucleotides for the nucleotides recited in any one of SEQ ID NOs:1, 4, or 23. Such "conservative amino acid" variants can be obtained, for example, by oligonucleotide-directed mutagenesis, linker-scanning mutagenesis, mutagenesis using the polymerase chain reaction, and the like (see Ausubel (1995) at pages 8–10 to 8–22; and McPherson (ed.), *Directed Mutagenesis: A Practical Approach* (IRL Press 1991)). The ability of such variants to promote anti-viral or anti-proliferative activity can be determined using a standard method, such as the assay described herein. Alternatively, a variant interferon-ε polypeptide can be identified by the ability to specifically bind anti-interferon-ε antibodies.

The proteins of the present invention can also comprise non-naturally occurring amino acid residues. Non-naturally occurring amino acids include, without limitation, trans-3-methylproline, 2,4-methanoproline, cis-4-hydroxyproline, trans-4-hydroxyproline, N-methylglycine, allo-threonine, methyltireonine, hydroxyethylcysteine, hydroxyethylhomocysteine, nitroglutamine, homoglutamine, pipecolic acid, thiazolidine carboxylic acid, dehydroproline, 3- and 4-methylproline, 3,3-dimethylproline, tert-leucine, norvaline, 2-azaphenylalanine, 3-azaphenylalanine, 4-azaphenylalanine, and 4-fluorophenylalanine. Several methods are known in the art for incorporating non-naturally occurring amino acid residues into proteins. For example, an in vitro system can be employed wherein nonsense mutations are suppressed using chemically aminoacylated suppressor tRNAs. Methods for synthesizing amino acids and aminoacylating tRNA are known in the art. Transcription and translation of plasmids containing nonsense mutations is typically caried out in a cell-free system comprising an *E. coli* S30 extract and commercially available enzymes and other reagents. Proteins are purified by chromatography. See, for example, Robertson et al., *J. Am. Chem. Soc.* 113:2722 (1991), Ellman et al., *Methods Enzymol.* 202:301 (1991), Chung et al., *Science* 259:806 (1993), and Chung et al., *Proc. Nat'l Acad. Sci. USA* 90:10145 (1993).

In a second method, translation is carried out in *Xenopus* oocytes by microinjection of mutated mRNA and chemically aminoacylated suppressor tRNAs (Turcatti et al., *J. Biol. Chem.* 271:19991 (1996)). Within a third method, *E. coli* cells are cultured in the absence of a natural amino acid that is to be replaced (e.g., phenylalanine) and in the presence of the desired non-naturally occurring amino acid(s) (e.g., 2-azaphenylalanine, 3-azaphenylalanine, 4-azaphenylalanine, or 4-fluorophenylalanine). The non-naturally occurring amino acid is incorporated into the protein in place of its natural counterpart. See, Koide et al., *Biochem.* 33:7470 (1994). Naturally occurring amino acid residues can be converted to non-naturally occurring species by in vitro chemical modification. Chemical modification can be combined with site-directed mutagenesis to further expand the range of substitutions (Wynn and Richards, *Protein Sci.* 2:395 (1993)).

A limited number of non-conservative amino acids, amino acids that are not encoded by the genetic code, non-naturally occurring amino acids, and unnatural amino acids may be substituted for interferon-ε amino acid residues.

Variants of either the human or the murine interferon-ε can be devised by aligning the amino acid sequences of interferon-ε polypeptides, and noting any differences in corresponding amino acid residues. As an illustration, the amino acid sequences of SEQ ID NO:2 and SEQ ID NO:24 can be aligned to identify any differences in corresponding amino acid residues 1 to 192. For example, the twenty-third amino acid residue of the human sequence is aspartic acid, while the twenty-third amino acid residue of the murine sequence is glutamic acid. Therefore, a variant human interferon-ε can be devised by substituting a glutamic acid residue for $Asp^{23}$.

As an additional example of this approach, the amino acid sequences of SEQ ID NOs:2 and 24 were aligned after introducing a single amino acid gap following amino acid residue 31 of SEQ ID NO:24. Table 4 presents differences between these aligned sequences through amino acid residue 191. Using the illustrative table, variants of the human interferon-ε sequence can be devised by introducing one or more amino acid substitutions from the corresponding murine sequence. Alternatively, variant murine interferon-ε sequences can be designed by introducing one or more amino acid substitutions from the corresponding human sequence. In this way, it is possible to obtain a "humanized" variant of the murine interferon-ε sequence. Although interferon-ε variants can be designed with any number of amino acid substitutions, certain variants will include at least about X amino acid substitutions, wherein X is selected from the group consisting of 2, 5, 10, 15, 20, 25, 30, 35, 40, 45, 50, 55, 60, 65, 70, and 75. Other variants may include all 78 amino acid substitutions shown in the table.

TABLE 4

| Human Interferon-ε (SEQ ID NO: 2) | | Murine Interferon-ε (SEQ ID NO: 24) | |
|---|---|---|---|
| Position | Amino Acid | Position | Amino Acid |
| 2 | Ile | 2 | Val |
| 3 | Ile | 3 | His |
| 4 | Lys | 4 | Arg |
| 5 | His | 5 | Gln |
| 6 | Phe | 6 | Leu |
| 7 | Phe | 7 | Pro |
| 8 | Gly | 8 | Glu |
| 12 | Val | 12 | Leu |
| 15 | Ala | 15 | Val |
| 17 | Thr | 17 | Ser |
| 23 | Asp | 23 | Glu |
| 24 | Leu | 24 | Pro |
| 26 | Leu | 26 | Arg |
| 28 | Ile | 28 | Pro |
| 31 | Gln | 31 | Leu |
| 32 | Arg | | (Gap) |
| 33 | Gln | 32 | Trp |
| 34 | Val | 33 | Met |
| 36 | Gln | 35 | Arg |
| 40 | Lys | 39 | Gln |

TABLE 4-continued

| Human Interferon-ε (SEQ ID NO: 2) | | Murine Interferon-ε (SEQ ID NO: 24) | |
|---|---|---|---|
| Position | Amino Acid | Position | Amino Acid |
| 43 | Asn | 42 | Lys |
| 44 | Lys | 43 | Pro |
| 46 | Gln | 45 | Pro |
| 47 | Thr | 46 | Ser |
| 48 | Leu | 47 | Ser |
| 50 | Ile | 49 | Val |
| 55 | Pro | 54 | Ala |
| 65 | Lys | 64 | Gln |
| 66 | Ser | 65 | Pro |
| 67 | Leu | 66 | Val |
| 70 | Gln | 69 | His |
| 74 | Lys | 73 | Glu |
| 76 | His | 75 | Gln |
| 77 | Thr | 76 | Val |
| 80 | Ile | 79 | Val |
| 81 | Leu | 80 | Val |
| 84 | Met | 83 | Ile |
| 90 | Ser | 89 | Thr |
| 92 | Phe | 91 | Leu |
| 93 | Arg | 92 | Gln |
| 94 | Ala | 93 | Thr |
| 95 | Asn | 94 | His |
| 96 | Ile | 95 | Gly |
| 97 | Ser | 96 | Thr |
| 98 | Leu | 97 | Met |
| 99 | Asp | 98 | Gly |
| 100 | Gly | 99 | Ile |
| 106 | Thr | 105 | Ile |
| 109 | Phe | 108 | Val |
| 111 | Ile | 110 | Ala |
| 112 | Gln | 111 | Ala |
| 115 | Gln | 114 | Arg |
| 120 | Leu | 119 | Val |
| 122 | Ala | 121 | Ser |
| 124 | Met | 123 | Gly |
| 127 | Glu | 126 | Asn |
| 129 | Glu | 128 | Ala |
| 130 | Lys | 129 | Gln |
| 131 | Leu | 130 | Lys |
| 134 | Thr | 133 | Gly |
| 135 | Leu | 134 | Ser |
| 136 | Gly | 135 | Ser |
| 137 | Ser | 136 | Ala |
| 138 | Asp | 137 | Gln |
| 144 | Val | 143 | Ile |
| 146 | Met | 145 | Ala |
| 159 | Asp | 158 | Arg |
| 162 | Thr | 161 | Ser |
| 166 | Ala | 165 | Ile |
| 170 | Val | 171 | Ile |
| 173 | Ser | 172 | His |
| 176 | Leu | 175 | Met |
| 181 | Ser | 180 | Arg |
| 182 | Leu | 181 | Phe |
| 184 | Glu | 183 | Thr |
| 185 | Lys | 184 | Trp |
| 188 | Lys | 187 | Arg |
| 191 | Arg | 190 | Pro |

Essential amino acids in the polypeptides of the present invention can be identified according to procedures known in the art, such as site-directed mutagenesis or alanine-scanning mutagenesis (Cunningham and Wells, *Science* 244:1081 (1989), Bass et al., *Proc. Nat'l Acad. Sci. USA* 88:4498 (1991), Coombs and Corey, "Site-Directed Mutagenesis and Protein Engineering," in *Proteins: Analysis and Design,* Angeletti (ed.), pages 259–311 (Academic Press, Inc. 1998)). In the latter technique, single alanine mutations are introduced at every residue in the molecule, and the resultant mutant molecules are tested for biological activity as disclosed below to identify amino acid residues that are critical to the activity of the molecule. See also, Hilton et al., *J. Biol. Chem.* 271:4699 (1996). The identities of essential amino acids can also be inferred from analysis of homologies with interferon-α, interferon-β, interferon-γ, interferon-δ, interferon-ω, and interferon-τ, as discussed in the "Overview" section of this specification.

Sequence analysis can also identify motifs that reside within human interferon polypeptides. As an illustration, the following human interferon sequences were analyzed for common sequence motifs: members of the interferon-α multigene family, interferon-β, interferon-δ, interferon-ω, and interferon-ε. The results of this analyses revealed two motifs in the interferon sequences. One motif occurs at amino acid residues 81 to 93 of interferon-ε, and has the following sequence: [LFI][HY]E[VML][IML]Q[QN][TISV]F[NSA][LI]F[STHRK], wherein acceptable amino acids for a given position are indicated within square brackets. Interferon-ε can be distinguished from human α, β, and ω interferons when the motif is further defined by the following conditions: (1) the last residue of the sequence is R, and (2) the first residue is L, or the second residue is H, or the seven residue is Q, or the tenth residue is S, or the eleventh residue is L. Accordingly, the present invention includes polypeptides that comprise an amino acid motif having the sequence [LFI][HY]E[VML][IML]Q[QN][TISV]F[NSA][LI]FR, wherein the sequence is further defined by at least one of the following conditions: the first residue is L, the second residue is H, the seventh residue is Q, the tenth residue is S, and the eleventh residue is L.

A second motif occurs at amino acid residues 160 to 172 of interferon-ε, and has the following sequence: YS[PSDTH]CAW[EAT][VTI]V[RQ][AMLV]EI, wherein acceptable amino acids for a given position are indicated within square brackets. Interferon-ε can be distinguished from human α, β, and ω interferons when the motif is further defined by one of the following conditions: (1) the third residue is T, or (2) the seventh residue is A, or (3) the tenth residue is Q. Thus, the present invention includes polypeptides that comprise an amino acid motif having the sequence YS[PSDTH]CAW[EAT][VTI]V[RQ][AMLV]EI, wherein the sequence is further defined by at least one of the following conditions: the third residue is T, the seventh residue is A, and the tenth residue is Q.

Sequence analysis also revealed a unique C-terminal peptide in the forms of human interferon-ε having the amino acid sequences of SEQ ID NOs:2 or 5. The present invention includes human interferons comprising this peptide, which is represented by amino acid residues 185 to 208 of either SEQ ID NO:2 or SEQ ID NO:5. Preferably, such a human interferon polypeptide comprises the sequence at the C-terminus of the polypeptide.

Although sequence analysis can be used to identify interferon-ε receptor binding sites, the location of interferon-ε receptor binding domains can also be determined by physical analysis of structure, as determined by such techniques as nuclear magnetic resonance, crystallography, electron diffraction or photoaffinity labeling, in conjunction with mutation of putative contact site amino acids. See, for examples de Vos et al., *Science* 255:306 (1992), Smith et al., *J. Mol. Biol.* 224:899 (1992), and Wlodaver et al., *FEBS Lett.* 309:59 (1992). Moreover, interferon-ε labeled with biotin or FITC can be used for expression cloning of interferon-ε receptors.

To date, studies have identified two main receptor binding sites in Type I interferons: one at a high affinity responsible for the binding to the receptor, and another site at lower affinity involved in mediating signal transduction (see, for example, Viscomi, *Biotherapy* 10:59 (1997)). The first site engages Helices A and B, and Loop AB, while the second site engages Helices A and C and Loop DE. Accordingly, mutations can be introduced into Helix C or Loop DE to interfere with interferon-ε receptor signaling. Such a mutant would be expected to bind an interferon-ε receptor without producing a biological effect, and therefore, would have the properties of an interferon-ε antagonist. As shown in Table 5, Helix C and Loop DE are represented by amino acids 103–123 and 159–162, respectively, of SEQ ID Nos. 2 or 5. Another form of interferon-ε antagonist could consist of Helices A and B, and Loop AB of the interferon-ε forms described herein (i.e., amino acids 27 to 94 of SEQ ID Nos. 2 or 5).

TABLE 5

| Structural Feature of Human Interferon-ε | Amino Acid Residues of SEQ ID NOs: 2 or 5 | Nucleotides of SEQ ID NOs: 1 or 4 |
| --- | --- | --- |
| Signal sequence | 1–21 | 454–516 |
| Helix A | 27–48 | 532–597 |
| AB Loop | 49–75 | 598–678 |
| Helix B | 76–94 | 679–735 |
| BC Loop | 95–102 | 736–759 |
| Helix C | 103–123 | 760–822 |
| CD Loop | 124–138 | 823–867 |
| Helix D | 139–158 | 868–927 |
| DE Loop | 159–162 | 928–936 |
| Helix E | 163–184 | 937–1005 |
| C-terminus | 185–208 | 1006–1077 |

As described below, fusion proteins can be produced that comprise structural features of two or more interferons. Examples of such chimeric interferons include proteins comprising helices and loops of human and murine interferons. Illustrative human-murine chimeric interferons have the structure: [hA or mA]-[hAB or mAB]-[hB or mB]-[hBC or mBC]-[hC or mC]-[hCD or mCD]-[hD or mD]-[hDE or mDE]-[hE or mE], wherein the designations "A" through "E" indicate a helix region, designations "AB" through "DE" indicate a loop region, and "h" and "m" refer to human interferon-ε and murine interferon-ε, respectively. Such chimeric proteins can also include a signal sequence at the N-terminus, a human interferon-ε or murine interferon-ε C-terminal amino acid sequence, or both such N-terminal and C-terminal amino acid sequences.

Particular human-murine embodiments can be devised using the above formula and the amino acid sequence information provided in Tables 5 and 6. As an illustration, a human-chimeric form of interferon-ε can have the formula: [mA]-[hAB]-[hB]-[hBC]-[hC]-[mCD]-[mD]-[hDE]-[mE]. Using Tables 5 and 6, a particular form of this chimeric protein can be designed as comprising: (amino acid residues 27 to 47 of SEQ ID NO:24)-(amino acid residues 49 to 123 of SEQ ID NO:2)-(amino acid residues 123 to 157 of SEQ ID NO:24)-(amino acid residues 159 to 162 of SEQ ID NO:2)-(amino acid residues 162 to 183 of SEQ ID NO:24). Variations on this particular chimeric protein include the addition of a signal sequence (e.g., an interferon-ε signal sequence). Moreover, a particular chimeric protein can include a human interferon-ε C-terminal sequence (e.g., amino acid residues 185 to 208 of SEQ ID NO:2) or a murine interferon-ε C-terminal sequence (e.g., amino acid residues 184 to 192 of SEQ ID NO:24). Other chimeric interferon-ε proteins can be devised by those of skill in the using the sequence information disclosed herein.

TABLE 6

| Structural Feature of Murine Interferon-ε | Amino Acid Residues of SEQ ID NO: 24 | Nucleotides of SEQ ID NO: 23 |
| --- | --- | --- |
| Signal sequence | 1–21 | 779–841 |
| Helix A | 27–47 | 857–919 |
| AB Loop | 48–74 | 920–1000 |
| Helix B | 75–93 | 1001–1057 |
| BC Loop | 94–101 | 1058–1081 |
| Helix C | 102–122 | 1082–1144 |
| CD Loop | 123–137 | 1145–1189 |
| Helix D | 138–157 | 1190–1249 |
| DE Loop | 158–161 | 1250–1261 |
| Helix E | 162–183 | 1262–1327 |
| C-terminus | 184–192 | 1328–1354 |

In addition, truncated variants are suggested by a comparison of human and murine interferon-ε sequences. For example, the amino acid sequence of SEQ ID NO:26 can be produced by inserting an adenosine-cytidine pair after nucleotide 1021 of SEQ ID NO:1. On the other hand, the deletion of nucleotide 1021 of SEQ ID NO:1 will result in the truncated interferon-ε that has the amino acid sequence of SEQ ID NO:27. In one study, a truncated mutant was produced by mutating a human interferon-ε sequence represented by nucleotides 1021 to 1035 of SEQ ID NO:1 to the following nucleotide sequence: GACCCAGACCCTTAG (SEQ ID NO:28). The resultant truncated human interferon-ε has the amino acid sequence of SEQ ID NO:29. The gene encoding this truncated form wag inserted into an expression vector for production of the polypeptide in mammalian cells.

Multiple amino acid substitutions can be made and tested using known methods of mutagenesis and screening, such as those disclosed by Reidhaar-Olson and Sauer (*Science* 241:53 (1988)) or Bowie and Sauer (*Proc. Nat'l Acad. Sci. USA* 86:2152 (1989)). Briefly, these authors disclose methods for simultaneously randomizing two or more positions in a polypeptide, selecting for functional polypeptide, and then sequencing the mutagenized polypeptides to determine the spectrum of allowable substitutions at each position. Other methods that can be used include phage display (e.g., Lowman et al., *Biochem.* 30:10832 (1991), Ladner et al., U.S. Pat. No. 5,223,409, Huse, international publication No. WO 92/06204, and region-directed mutagenesis (Derbyshire et al., *Gene* 46:145 (1986), and Ner et al., *DNA* 7:127, (1988)).

Variants of the disclosed interferon-ε nucleotide and polypeptide sequences can also be generated through DNA shuffling as disclosed by Stemmer, *Nature* 370:389 (1994), Stemmer, *Proc. Nat'l Acad. Sci. USA* 91:10747 (1994), and international publication No. WO 97/20078. Briefly, variant DNAs are generated by in vitro homologous recombination by random fragmentation of a parent DNA followed by reassembly using PCR, resulting in randomly introduced point mutations. This technique can be modified by using a family of parent DNAs, such as allelic variants or DNAs from different species, to introduce additional variability into the process. Selection or screening for the desired activity, followed by additional iterations of mutagenesis and assay provides for rapid "evolution" of sequences by selecting for desirable mutations while simultaneously selecting against detrimental changes.

Mutagenesis methods as disclosed herein can be combined with high-throughput, automated screening methods to detect activity of cloned, mutagenized polypeptides in host cells. Mutagenized DNA molecules that encode biologically active polypeptides, or polypeptides that bind with anti-interferon-ε antibodies, can be recovered from the host cells and rapidly sequenced using modern equipment. These methods allow the rapid determination of the importance of individual amino acid residues in a polypeptide of interest, and can be applied to polypeptides of unknown structure.

The present invention also includes "functional fragments" of interferon-ε polypeptides and nucleic acid molecules encoding such functional fragments. Routine deletion analyses of nucleic acid molecules can be performed to obtain functional fragments of a nucleic acid molecule that encodes an interferon-ε polypeptide. As an illustration, DNA molecules having the nucleotide sequence of SEQ ID NO. 1 can be digested with Bal31 nuclease to obtain a series of nested deletions. The fragments are then inserted into expression vectors in proper reading frame, and the expressed polypeptides are isolated and tested for anti-viral or anti-proliferative activity, or for the ability to bind anti-interferon-ε antibodies. One alternative to exonuclease digestion is to use oligonucleotide-directed mutagenesis to introduce deletions or stop codons to specify production of a desired fragment. Alternatively, particular fragments of an interferon-ε gene can be synthesized using the polymerase chain reaction.

Studies on the truncation at eider or both termini of interferons have been summarized by Horisberger and Di Marco, *Pharmac. Ther.* 66:507 (1995). Moreover, standard techniques for functional analysis of proteins are described by, for example, Treuter et al., *Molec. Gen. Genet.* 240:113 (1993), Content et al., "Expression and preliminary deletion analysis of the 42 kDa 2-5A synthetase induced by human interferon," in *Biological Interferon Systems, Proceedings of ISIR-TNO Meeting on Interferon Systems,* Cantell (ed.), pages 65–72 (Nijhoff 1987), Herschman, "The EGF Receptor," in *Control of Animal Cell Proliferation, Vol* 1, Boynton et al., (eds.) pages 169–199 (Academic Press 1985), Coumailleau et al., *J. Biol. Chem.* 270:29270 (1995); Fukunaga et al., *J. Biol. Chem.* 270:25291 (1995); Yamaguchi et al., *Biochem. Pharmacol.* 50:1295 (1995), and Meisel et al., *Plant Molec. Biol.* 30:1 (1996).

The present invention also contemplates functional fragments of an interferon-ε gene that has amino acid changes, compared with the amino acid sequence of SEQ ID NO:2, SEQ ID NO:5, or SEQ ID NO:24. A variant interferon-ε gene can be identified on the basis of structure by determining the level of identity with nucleotide and amino acid sequences of SEQ ID NOs:1, 2, 4, 5, 23, and 24 as discussed above. An alternative approach to identifing a variant gene on the basis of structure is to determine whether a nucleic acid molecule encoding a potential variant interferon-ε gene can hybridize to a nucleic acid molecule having the nucleotide sequence of SEQ ID NO:1, SEQ ID NO:4, or SEQ ID NO:23, as discussed above.

The present invention also provides polypeptide fragments or peptides comprising an epitope-bearing portion of an interferon-ε polypeptide described herein. Such fragments or peptides may comprise an "immunogenic epitope," which is a part of a protein that elicits an antibody response when the entire protein is used as an immunogen. Immunogenic epitope-bearing peptides can be identified using standard methods (see, for example, Geysen et al., *Proc. Nat'l Acad. Sci. USA* 81:3998 (1983)).

In contrast, polypeptide fragments or peptides may comprise an "antigenic epitope," which is a region of a protein molecule to which an antibody can specifically bind. Certain epitopes consist of a linear or contiguous stretch of amino acids, and the antigenicity of such an epitope is not disrupted by denaturing agents. It is known in the art that relatively short synthetic peptides that can mimic epitopes of a protein can be used to stimulate the production of antibodies against the protein (see, for example, Sutcliffe et al., *Science* 219:660 (1983)). Accordingly, antigenic epitope-bearing peptides and polypeptides of the present invention are useful to raise antibodies that bind with the polypeptides described herein.

Antigenic epitope-bearing peptides and polypeptides preferably contain at least four to ten amino acids, at least ten to fifteen amino acids, or about 15 to about 30 amino acids of SEQ ID NO:2 (or SEQ ID NO:5 or SEQ ID NO:24). Such epitope-bearing peptides and polypeptides can be produced by fragmenting an interferon-ε polypeptide, or by chemical peptide synthesis, as described herein. Moreover, epitopes can be selected by phage display of random peptide libraries (see, for example, Lane and Stephen, *Curr. Opin. Immunol.* 5:268 (1993), and Cortese et al., *Curr. Opin. Biotechnol.* 7:616 (1996)). Standard methods for identifying epitopes and producing antibodies from small peptides that comprise an epitope are described, for example, by Mole, "Epitope Mapping," in *Methods in Molecular Biology, Vol.* 10, Manson (ed.), pages 105–116 (The Humana Press, Inc. 1992), Price, "Production and Characterization of Synthetic Peptide-Derived Antibodies," in *Monoclonal Antibodies: Production, Engineering, and Clinical Application,* Ritter and Ladyman (eds.), pages 60–84 (Cambridge University Press 1995), and Coligan et al. (eds.), *Current Protocols in Immunology,* pages 9.3.1–9.3.5 and pages 9.4.1–9.4.11 (John Wiley & Sons 1997).

Regardless of the particular nucleotide sequence of a variant interferon-ε gene, the gene encodes a polypeptide that is characterized by its anti-viral or anti-proliferative activity, or by the ability to bind specifically to an anti-interferon-ε antibody. More specifically, variant human interferon-ε genes encode polypeptides which exhibit at least 50%, and preferably, greater than 70, 80, or 90%, of the activity of polypeptide encoded by the human interferon-ε gene described herein. Similarly, variant murine interferon-ε genes encode polypeptides which exhibit at least 50%, and preferably, greater than 70, 80, or 90%, of the activity of polypeptide encoded by the murine interferon-ε gene described herein.

For any interferon-ε polypeptide, including variant and fusion proteins, one of ordinary skill in the art can readily generate a fully degenerate polynucleotide sequence encoding that variant using the information set forth in Tables 1 and 2 above. Moreover, those of skill in the art can use standard software to devise interferon-ε variants based upon the nucleotide and amino acid sequences described herein. Accordingly, the present invention includes a computer-readable medium encoded with a data structure that provides at least one of the following sequences; SEQ ID NO:1, SEQ ID:2, SEQ ID NO:3, SEQ ID NO:4, SEQ ID NO:5, SEQ ID NO:6, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:21, SEQ ID NO:22, SEQ ID NO:23, SEQ ID NO:24, SEQ ID NO:25, SEQ ID NO:26, and SEQ ID NO:27. For example, a computer-readable medium can be encoded with a data structure that provides at least one of the following sequences: SEQ ID NO:1, SEQ ID NO:2, SEQ ID NO:3, SEQ ID NO:4, SEQ ID NO:5, SEQ ID NO:6, SEQ ID NO:23, SEQ ID NO:24, SEQ ID NO:25, SEQ ID NO:26, and SEQ ID NO:27. Suitable forms of computer-readable media include magnetic media and optically-readable media. Examples of magnetic media include a hard or fixed drive, a random access memory (RAM) chip, a floppy disk, digital linear tape (DLT), a disk cache, and a ZIP disk. Optically readable media are exemplified by compact discs (e.g, CD-read only memory (ROM), CD-rewritable (RW), and CD-recordable), and digital versatile/video discs (DVD) (e.g, DVD-ROM, DVD-RAM, and DVD+RW).

5. Production of Interferon-ε Fusion Proteins and Conjugates

Fusion proteins of interferon-ε can be used to express interferon-ε in a recombinant host, and to isolate expressed interferon-ε. As described below, particular interferon-ε fusion proteins also have uses in diagnosis and therapy.

One type of fusion protein comprises a peptide that guides an interferon-ε polypeptide from a recombinant host cell. To direct an interferon-ε polypeptide into the secretory pathway of a eukaryotic host cell, a secretory signal sequence (also known as a signal peptide, a leader sequence, prepro sequence or pre sequence) is provided in the interferon-ε expression vector. While the secretory signal sequence may be derived from interferon-ε, a suitable signal sequence may also be derived from another secreted protein or synthesized de novo. The secretory signal sequence is operably linked to an interferon-ε-encoding sequence such that the two sequences are joined in the correct reading frame and positioned to direct the newly synthesized polypeptide into the secretory pathway of the host cell. Secretory signal sequences are commonly positioned 5' to the nucleotide sequence encoding the polypeptide of interest, although certain secretory signal sequences may be positioned elsewhere in the nucleotide sequence of interest (see, e.g., Welch et al., U.S. Pat. No. 5,037,743; Holland et al., U.S. Pat. No. 5,143,830).

Although the secretory signal sequence of interferon-ε or another protein produced by mammalian cells (e.g., tissue-type plasminogen activator signal sequence, as described, for example, in U.S. Pat. No. 5,641,655) is useful for expression of interferon-ε in recombinant mammalian hosts, a yeast signal sequence is preferred for expression in yeast cells. Examples of suitable yeast signal sequences are those derived from yeast mating phermone ε-factor (encoded by the MFε1 gene), invertase (encoded by the SUC2 gene), or acid phosphatase (encoded by the PHO5 gene). See, for example, Romanos et al., "Expression of Cloned Genes in Yeast," in *DNA Cloning 2: A Practical Approach*, 2$^{nd}$ Edition, Glover and Hames (eds.), pages 123–167 (Oxford University Press 1995).

In bacterial cells, it is often desirable to express a heterologous protein as a fusion protein to decrease toxicity, increase stability, and to enhance recovery of the expressed protein. For example, interferon-ε can be expressed as a fusion protein comprising a glutathione S-transferase polypeptide. Glutathione S-transferease fusion proteins are typically soluble, and easily purifiable from *E. coli* lysates on immobilized glutathione columns. In similar approaches, an interferon-ε fusion protein comprising a maltose binding protein polypeptide can be isolated with an amylose resin column, while a fusion protein comprising the C-terminal end of a truncated Protein A gene can be purified using IgG-Sepharose. Established techniques for expressing a heterologous polypeptide as a fusion protein in a bacterial cell are described, for example, by Williams et al., "Expression of Foreign Proteins in *E. coli* Using Plasmid Vectors and Purification of Specific Polyclonal Antibodies," in *DNA Cloning 2: A Practical Approach*, 2$^{nd}$ Edition, Glover and Hames (Eds.), pages 15–58 (Oxford University Press 1995).

In addition, commercially available expression systems are available. For example, the PINPOINT Xa protein purification system (Promega Corporation; Madison, Wis.) provides a method for isolating a fusion protein comprising a polypeptide that becomes biotinylated during expression with a resin that comprises avidin.

Peptide tags that are useful for isolating heterologous polypeptides expressed by either prokaryotic or eukaryotic cells include polyhistidine tags (which have an affinity for nickel-chelating resin), c-myc tags, calmodulin binding protein (isolated with calmodulin affinity chromatography), substance P, the RYIRS tag (which binds with anti-RYIRS antibodies), the Glu-Glu tag, and the FLAG tag (which binds with anti-FLAG antibodies). See, for example, Luo et al., *Arch. Biochem. Biophys.* 329:215 (1996), Morganti et al., *Biotechnol. Appl. Biochem.* 23:67 (1996), and Zheng et al., *Gene* 186:55 (1997). Nucleic acid molecules encoding such peptide tags are available, for example, from Sigma-Aldrich Corporation (St. Louis, Mo.).

The present invention also contemplates that the use of the secretory signal sequence contained in the interferon-ε polypeptides of the present invention to direct other polypeptides into the secretory pathway. A signal fusion polypeptide can be made wherein a secretory signal sequence derived from amino acid residues 1 to 21 of SEQ ID NO:2 (or amino acid residues 1 to 21 of SEQ ID NO:24) is operably linked to another polypeptide using methods known in the art and disclosed herein. The secretory signal sequence contained in the fusion polypeptides of the present invention is preferably fused amino-terminally to an additional peptide to direct the additional peptide into the secretory pathway. Such constructs have numerous applications known in the art. For example, these novel secretory signal sequence fusion constructs can direct the secretion of an active component of a normally non-secreted protein, such as a receptor. Such fusions may be used in a transgenic animal or in a cultured recombinant host to direct peptides through the secretory pathway. With regard to the latter, exemplary polypeptides include pharmaceutically active molecules such as Factor VIIa, proinsulin, insulin, follicle stimulating hormone, tissue type plasminogen activator, tumor necrosis factor, interleukins (e.g., interleukin-1 (IL-1), IL-2, IL-3, IL-4, IL-5, IL-6, IL-7, IL-8, IL-9, IL-10, IL-11, IL-12, IL-13, IL-14, and IL-15), colony stimulating factors (e.g., granulocyte-colony stimulating factor (G-CSF) and granulocyte macrophage-colony stimulating factor (GM-CSF)), interferons (e.g., interferons-α, -β, -γ, -ω, -δ, and -τ), the stem cell growth factor designated "S1 factor," erythropoietin, and thrombopoietin. The interferon-ε secretory signal sequence contained in the fusion polypeptides of the present invention is preferably fused amino-terminally to an additional peptide to direct the additional peptide into the secretory pathway. Fusion proteins comprising an interferon-ε secretory signal sequence can be constructed using standard techniques.

Another form of fusion protein comprises an interferon-ε polypeptide and an immunoglobulin heavy chain constant region, typically an $F_c$ fragment, which contains two or three constant region domains and a hinge region but lacks the variable region. As an illustration, Chang et al., U.S. Pat. No. 5,723,125, describe a fusion protein comprising a human interferon and a human immunoglobulin Fc fragment. The C-terminal of the interferon is linked to the N-terminal of the Fc fragment by a peptide linker moiety. An example of a peptide linker is a peptide comprising primarily a T cell inert sequence, which is immunologically inert. An exemplary peptide linker has the amino acid sequence: GGSGG SGGGG SGGGG S (SEQ ID NO:20). In this fusion protein, a preferred Fc moiety is a human γ4 chain, which is stable in solution and has little or no complement activating activity. Accordingly, the present invention contemplates an interferon-ε fusion protein that comprises all interferon-ε moiety and a human Fc fragment, wherein the C-terminus of the interferon-ε moiety is attached to the N-terminus of the Fc fragment via a peptide linker, such as a peptide consisting of the amino acid sequence of SEQ ID NO:20. The interferon-ε moiety can be an interferon-ε molecule or a fragment thereof.

In another variation, an interferon-ε fusion protein comprises an IgG sequence, an interferon-ε moiety covalently joined to the aminoterminal end of the IgG sequence, and a signal peptide that is covalently joined to the aminoterminal of the interferon-ε moiety, wherein the IgG sequence consists of the following elements in the following order: a hinge region, a $CH_2$ domain, and a $CH_3$ domain. Accordingly, the IgG sequence lacks a $CH_1$ domain. The interferon-ε moiety displays an interferon-ε activity, as described herein, such as the ability to bind with an interferon-ε receptor. This general approach to producing fusion proteins that comprise both antibody and nonantibody portions has been described by LaRochelle et al., EP 742830 (WO 95/21258).

Fusion proteins comprising an interferon-ε moiety and an Fc moiety can be used, for example, as an in vitro assay tool. For example, the presence of an interferon-ε receptor in a biological sample can be detected using an interferon-ε immunoglobulin fusion protein, in which the interferon-ε moiety is used to target the cognate receptor, and a macromolecule, such as Protein A or anti-Fc antibody, is used to detect the bound fusion protein-receptor complex. Moreover, such fusion proteins can be used to identify agonists and antagonists that interfere with the binding of interferon-ε to its receptor.

Similarly, fusion proteins can be constructed that comprise a murine interferon-ε polypeptide and an immunoglobulin heavy chain constant region In addition, antibody-interferon-ε fusion proteins, comprising antibody variable domains, are useful as therapeutic proteins, in which the antibody moiety binds with a target antigen, such as a tumor associated antigen. Methods of making antibody-cytokine fusion proteins are known to those of skill in the art. For example, antibody fusion proteins comprising an interleukin-2 moiety are described by Boleti et al., *Ann. Oncol.* 6:945 (1995), Nicolet et al., *Cancer Gene Ther.* 2:161 (1995), Becker et al., *Proc. Nat'l Acad. Sci. USA* 93:7826 (1996), Hank et al., *Clin. Cancer Res.* 2:1951 (1996), and Hu et al., *Cancer Res.* 56:4998 (1996). Moreover, Yang et al., *Hum. Antibodies Hybridomas* 6:129 (1995), and Xiang et al., *J. Biotechnol.* 53:3 (1997), describe fusion proteins that include an F(ab')$_2$ fragment and a tumor necrosis factor alpha moiety. Additional cytokine-antibody fusion proteins include IL-8, IL-12, or interferon-τ as the cytokine moiety (Holzer et al., *Cytokine* 8:214 (1996); Gillies et al., *J. Immunol.* 160:6195 (1998); Xiang et al., *Hum. Antibodies Hybridomas* 7:2 (1996)). Also see, Gillies, U.S. Pat. No. 5,650,150.

Moreover, using methods described in the art, hybrid interferon-ε proteins can be constructed using regions or domains of the inventive interferon-ε in combination with those of other interferon family proteins (i.e., interferon-α, interferon-β, interferon-γ, interferon-δ, interferon-ω, and interferon-τ), or heterologous proteins (see, for example, Picard, *Cur. Opin. Biology* 5:511 (1994)). These methods allow the determination of the biological importance of larger domains or regions in a polypeptide of interest. Such hybrids may alter reaction kinetics, binding, constrict or expand the substrate specificity, or alter tissue and cellular localization of a polypeptide, and can be applied to polypeptides of unknown structure. For example Horisberger and DiMarco, *Pharmac. Ther.* 66:507 (1995), describe the construction of fusion protein hybrids comprising different interferon-α subtypes, as well as hybrids comprising interferon-α domains from different species.

Fusion proteins can be prepared by methods known to those skilled in the art by preparing each component of the fusion protein and chemically conjugating them. Alternatively, a polynucleotide encoding both components of the fusion protein in the proper reading frame can be generated using known techniques and expressed by the methods described herein. For example, part or all of a domain(s) conferring a biological function may be swapped between interferon-ε of the present invention with the functionally equivalent domain(s) from another family member, such as interferon-α, interferon-β, interferon-δ, interferon-γ, interferon-ω, or interferon-τ. Such domains include, but are not limited to, the secretory signal sequence, helices A, B, C, D, and E, and loops AB, BC, CD, and DE. Such fusion proteins would be expected to have a biological functional profile that is the same or similar to polypeptides of the present invention or other known interferon family proteins, depending on the fusion constructed. Moreover, such fusion proteins may exhibit other properties as disclosed herein. General methods for enzymatic and chemical cleavage of fusion proteins are described, for example, by Ausubel (1995) at pages 16–19 to 16–25.

The present invention also contemplates chemically modified interferon-ε compositions, in which an interferon-ε polypeptide is linked with a polymer. Typically, the polymer is water soluble so that the interferon-ε conjugate does not precipitate in an aqueous environment, such as a physiological environment. An example of a suitable polymer is one that has been modified to have a single reactive group, such as an active ester for acylation, or an aldehyde for alkylation. In this way, the degree of polymerization can be controlled. An example of a reactive aldehyde is polyethylene glycol propionaldehyde, or mono-(C1–C10) alkoxy, or aryloxy derivatives thereof (see, for example, Harris, et al., U.S. Pat. No. 5,252,714). The polymer may be branched or unbranched. Moreover, a mixture of polymers can be used to produce interferon-ε conjugates.

Interferon-ε conjugates used for therapy should preferably comprise pharmaceutically acceptable water-soluble polymer moieties. Conjugation of interferons with water-soluble polymers has been shown to enhance the circulating half-life of the interferon, and to reduce the immunogenicity of the polypeptide (see, for example, Nieforth et al., *Clin. Pharmacol. Ther.* 59:636 (1996), and Monkarsh et al., *Anal. Biochem.* 247:434 (1997)).

Suitable water-soluble polymers include polyethylene glycol (PEG), monomethoxy-PEG, mono-(C1–C10)alkoxy-PEG, aryloxy-PEG, poly-(N-vinyl pyrrolidone)PEG, tresyl monomethoxy PEG, PEG propionaldehyde, bis-succinimidyl carbonate PEG, propylene glycol homopolymers, a polypropylene oxide/ethylene oxide co-polymer, polyoxyethylated polyols (e.g., glycerol), polyvinyl alcohol, dextran, cellulose, or other carbohydrate-based polymers. Suitable PEG may have a molecular weight from about 600 to about 60,000, including, for example, 5,000, 12,000, 20,000 and 25,000. An interferon-ε conjugate can also comprise a mixture of such water-soluble polymers.

One example of an interferon-ε conjugate comprises an interferon-ε moiety and a polyalkyl oxide moiety attached to the N-terminus of the interferon-ε moiety. PEG is one suitable polyalkyl oxide. As an illustration, interferon-ε can be modified with PEG, a process known as "PEGylation." PEGylation of interferon-ε can be carried out by any of the PEGylation reactions known in the art (see, for example, EP 0 154 316, Delgado et al., *Critical Reviews in Therapeutic Drug Carrier Systems* 9:249 (1992), Duncan and Spreafico, *Clin. Pharmacokinet.* 27:290 (1994), and Francis et al., *Int J Hematol* 68:1 (1998)). For example, PEGylation can be performed by an acylation reaction or by an alkylation reaction with a reactive polyethylene glycol molecule. In an alternative approach, interferon-ε conjugates are formed by condensing activated PEG, in which a terminal hydroxy or amino group of PEG has been replaced by an activated linker (see, for example, Karasiewicz et al, U.S. Pat. No. 5,382,657).

PEGylation by acylation typically requires reacting an active ester derivative of PEG with an interferon-ε polypeptide. An example of an activated PEG ester is PEG esterifed to N-hydroxysuccinimide. As used herein, the term "acylation" includes the following types of linkages between interferon-ε and a water soluble polymer: amide, carbamate, urethane, and the like. Methods for preparing PEGylated interferon-ε by acylation will typically comprise the steps of (a) reacting an interferon-ε polypeptide with PEG (such as a reactive ester of an aldehyde derivative of PEG) under conditions whereby one or more PEG groups attach to interferon-ε, and (b) obtaining the reaction product(s). Generally, the optimal reaction conditions for acylation reactions will be determined based upon known parameters and desired results. For example, the larger the ratio of PEG:interferon-ε, the greater the percentage of polyPEGylated interferon-ε product.

The product of PEGylation by acylation is typically a polyPEGylated interferon-ε product, wherein the lysine ε-amino groups are PEGylated via an acyl linking group. An example of a connecting linkage is an amide. Typically, the resulting interferon-ε will be at least 95% mono-, di-, or tri-pegylated, although some species with higher degrees of PEGylation may be formed depending upon the reaction conditions. PEGylated species can be separated from unconjugated interferon-ε polypeptides using standard purification methods, such as dialysis, ultrafiltration, ion exchange chromatography, affinity chromatography, and the like.

PEGylation by alkylation generally involves reacting a terminal aldehyde derivative of PEG with interferon-ε in the presence of a reducing agent. PEG groups are preferably attached to the polypeptide via a —CH$_2$—NH group.

Derivatization via reductive alkylation to produce a monoPEGylated product takes advantage of the differential reactivity of different types of primary amino groups available for derivatization. Typically, the reaction is performed at a pH that allows one to take advantage of the pKa differences between the ε-amino groups of the lysine residues and the α-amino group of the N-terminal residue of the protein. By such selective derivatization, attachment of a water-soluble polymer that contains a reactive group such as an aldehyde, to a protein is controlled. The conjugation with the polymer occurs predominantly at the N-terminus of the protein without significant modification of other reactive groups such as the lysine side chain amino groups. The present invention provides a substantially homogenous preparation of interferon-ε monopolymer conjugates.

Reductive alkylation to produce a substantially homogenous population of monopolymer interferon-ε conjugate molecule can comprise the steps of: (a) reacting an interferon-ε polypeptide with a reactive PEG under reductive alkylation conditions at a pH suitable to permit selective modification of the α-amino group at the amino terminus of the interferon-ε, and (b) obtaining the reaction product(s). The reducing agent used for reductive alkylation should be stable in aqueous solution and preferably be able to reduce only the Schiff base formed in the initial process of reductive alkylation. Preferred reducing agents include sodium borohydride, sodium cyanoborohydride, dimethylamine borane, trimethylamine borane, and pyridine borane.

For a substantially homogenous population of monopolymer interferon-ε conjugates, the reductive alkylation reaction conditions are those which permit the selective attachment of the water soluble polymer moiety to the N-terminus of interferon-ε. Such reaction conditions generally provide for pKa differences between the lysine amino groups and the α-amino group at the N-terminus. The pH also affects the ratio of polymer to protein to be used. In general, if the pH is lower, a larger excess of polymer to protein will be desired because the less reactive the N-terminal α-group, the more polymer is needed to achieve optimal conditions. If the pH is higher, the polymer:interferon-ε need not be as large because more reactive groups are available. Typically, the pH will fall within the range of 3–9, or 3–6.

Another factor to consider is the molecular weight of the water-soluble polymer. Generally, the higher the molecular weight of the polymer, the fewer number of polymer molecules which may be attached to the protein. For PEGylation reactions, the typical molecular weight is about 2 kDa to about 100 kDa, about 5 kDa to about 50 kDa, or about 12 kDa to about 25 kDa. The molar ratio of water-soluble polymer to interferon-ε will generally be in the range of 1:1 to 100:1. Typically, the molar ratio of water-soluble polymer to interferon-ε will be 1:1 to 20:1 for polyPEGylation, and 1:1 to 5:1 for monoPEGylation.

General methods for producing conjugates comprising interferon and water-soluble polymer moieties are known in the art. See, for example, Karasiewicz et al., U.S. Pat. No. 5,382,657, Greenwald et al., U.S. Pat. No. 5,738, 846, Nieforth et al., *Clin. Pharmacol. Ther.* 59:636 (1996), Monkarsh et al., *Anal. Biochem.* 247:434 (1997)).

6. Production of Interferon-ε Polypeptides

The polypeptides of the present invention, including full-length polypeptides, functional fragments, and fusion proteins, can be produced in recombinant host cells following conventional techniques. To express an interferon-ε gene, a nucleic acid molecule encoding the polypeptide must be operably linked to regulatory sequences that control transcriptional expression in an expression vector and then, itroduced into a host cell. In addition to transcriptional regulatory sequences, such as promoters and enhancers, expression vectors can include translational regulatory sequences and a marker gene which is suitable for selection of cells that carry the expression vector.

Expression vectors that are suitable for production of a foreign protein in eukaryotic cells typically contain (1) prokaryotic DNA elements coding for a bacterial replication origin and an antibiotic resistance marker to provide for the growth and selection of the expression vector in a bacterial host; (2) eukaryotic DNA elements that control initiation of transcription, such as a promoter; and (3) DNA elements that control the processing of transcripts, such as a transcription termination/polyadenylation sequence. As discussed above, expression vectors can also include nucleotide sequences encoding a secretory sequence that directs the heterologous polypeptide into the secretory pathway of a host cell. For example, an interferon-ε expression vector may comprise an interferon-ε gene and a secretory sequence derived from an interferon-ε gene or another secreted gene.

Interferon-ε proteins of the present invention may be expressed in mammalian cells. Examples of suitable mammalian host cells include African green monkey kidney cells (Vero; ATCC CRL 1587), human embryonic kidney cells (293-HEK; ATCC CRL 1573), baby hamster kidney cells (BHK-21, BHK-570; ATCC CRL 8544, ATCC CRL 10314), canine kidney cells (MDCK; ATCC CCL 34), Chinese hamster ovary cells (CHO-K1; ATCC CCL61; CHO DG44 [Chasin et al., *Som. Cell. Molec. Genet.* 12:555 (1986)]), rat pituitary cells (GH1; ATCC CCL82), HeLa S3 cells (ATCC CCL2.2), rat hepatoma cells (H-4-II-E; ATCC CRL 1548) SV40-transformed monkey kidney cells (COS-1; ATCC CRL 1650) and murine embryonic cells (NIH-3T3; ATCC CRL 1658).

For a mammalian host, the transcriptional and translational regulatory signals may be derived from viral sources, such as adenovirus, bovine papilloma virus, simian virus, or the like, in which the regulatory signals are associated with a particular gene which has a high level of expression. Suitable transcriptional and translational regulatory sequences also can be obtained from mammalian genes, such as actin, collagen, myosin, and metallothionein genes.

Transcriptional regulatory sequences include a promoter region sufficient to direct the initiation of RNA synthesis. Suitable eukaryotic promoters include the promoter of the mouse metallothionein I gene (Hamer et al., *J. Molec. Appl. Genet.* 1:273 (1982)), the TK promoter of Herpes virus (McKnight, *Cell* 31:355 (1982)), the SV40 early promoter (Benoist et al., *Nature* 290:304 (1981)), the Rous sarcoma virus promoter (Gorman et al., *Proc. Nat'l Acad. Sci. USA* 79:6777 (1982)), the cytomegalovirus promoter (Foecking et al., *Gene* 45:101 (1980)), and the mouse mammary tumor virus promoter (see, generally, Etcheverry, "Expression of Engineered Proteins in Mammalian Cell Culture," in *Protein Engineering: Principles and Practice,* Cleland et al. (eds.), pages 163–181 (John Wiley & Sons, Inc. 1996)).

Alternatively, a prokaryotic promoter, such as the bacteriophage T3 RNA polymerase promoter, can be used to control interferon-ε gene expression in mammalian cells if the prokaryotic promoter is regulated by a eukaryotic promoter (Zhou et al., *Mol. Cell. Biol.* 10:4529 (1990), and Kaufman et al., *Nucl. Acids Res.* 19:4485 (1991)).

An expression vector can be introduced into host cells using a variety of standard techniques including calcium phosphate transfection, liposome-mediated transfection, microprojectile-mediated delivery, electroporation, and the like. Preferably, the transfected cells are selected and propagated to provide recombinant host cells that comprise the expression vector stably integrated in the host cell genome. Techniques for introducing vectors into eukaryotic cells and techniques for selecting such stable transformants using a dominant selectable marker are described, for example, by Ausubel (1995) and by Murray (ed.), *Gene Transfer and Expression Protocols* (Humana Press 1991).

For example, one suitable selectable marker is a gene that provides resistance to the antibiotic neomycin. In this case, selection is carried out in the presence of a neomycin-type drug, such as G-418 or the like. Selection systems can also be used to increase the expression level of the gene of interest, a process referred to as "amplification." Amplification is carried out by culturing transfectants in the presence of a low level of the selective agent and then increasing the amount of selective agent to select for cells that produce high levels of the products of the introduced genes. A preferred amplifiable selectable marker is dihydrofolate reductase, which confers resistance to methotrexate. Other drug resistance genes (e.g., hygromycin resistance, multidrug resistance, puromycin acetyltransferase) can also be used. Alternatively, markers that introduce an altered phenotype, such as green fluorescent protein, or cell surface proteins such as CD4, CD8, Class I MHC, placental alkaline phosphatase may be used to sort transfected cells from untransfected cells by such means as FACS sorting or magnetic bead separation technology.

Interferon-ε polypeptides can also be produced by cultured mammalian cells using a viral delivery system. Exemplary viruses for this purpose include adenovirus, herpesvirus, vaceinia virus and adeno-associated virus (AAV). Adenovirus, a double-stranded DNA virus, is currently the best studied gene transfer vector for delivery of heterologous nucleic acid (for a review, see Becker et al., *Meth. Cell Biol.* 43:161 (1994), and Douglas and Curiel, *Science & Medicine* 4:44 (1997)). Advantages of the adenovirus system include the accommodation of relatively large DNA inserts, the ability to grow to high-titer, the ability to infect a broad range of mammalian cell types, and flexibility that allows use with a large number of available vectors containing different promoters.

By deleting portions of the adenovirus genome, larger inserts (up to 7 kb) of heterologous DNA can be accommodated. These inserts can be incorporated into the viral DNA by direct ligation or by homologous recombination with a co-transfected plasmid. An option is to delete the essential E1 gene from the viral vector, which results in the inability to replicate unless the E1 gene is provided by the host cell. Adenovirus vector-infected human 293 cells (ATCC Nos. CRL-1573, 45504, 45505), for example, can be grown as adherent cells or in suspension culture at relatively high cell density to produce significant amounts of protein (see Garnier et al., *Cytotechnol.* 15:145 (1994)).

Interferon-ε genes may also be expressed in other higher eukryotic cells, such as avian, fungal, insect, yeast, or plant cells. The baculovirus system provides an efficient means to introduce cloned interferon-ε genes into insect cells. Suitable expression vectors are based upon the *Autographa californica* multiple nuclear polyhedrosis virus (AcMNPV), and contain well-known promoters such as Drosophila heat shock protein (hsp) 70 promoter, *Autographa californica* nuclear polyhedrosis virus immediate-early gene promoter (ie-1) and the delayed early 39K promoter, baculovirus p10 promoter, and the *Drosophila metallothionein* promoter. A second method of making recombinant baculovirus utilizes a transposon-based system described by Luckow (Luckow, et al., *J. Virol.* 67:4566 (1993)). This system, which utilizes transfer vectors, is sold in the BAC-to-BAC kit (Life Technologies, Rockville, Md.). This system utilizes a transfer vector, PFASTBAC (Life Technologies) containing a Tn7 transposon to move the DNA encoding the interferon-ε polypeptide into a baculovirus genome maintained in *E. coli* as a large plasmid called a "bacmid." See, Hill-Perkins and Possee, *J. Gen. Virol.* 71:971 (1990), Bonning, et al., *J. Gen. Virol.* 75:1551 (1994), and Chazenbalk, and Rapoport, *J. Biol. Chem.* 270:1543 (1995). In addition, transfer vectors can include an in-frame fusion with DNA encoding an epitope tag at the C- or N-terminus of the expressed interferon-ε polypeptide, for example, a Glu-Glu epitope tag (Grussenmeyer et al., *Proc. Nat'l Acad. Sci.* 82:7952 (1985)). Using a technique known in the art, a transfer vector containing an interferon-ε gene is transformed into *E. coli,* and screened for bacmids which contain an interrupted lacZ gene indicative of recombinant baculovirus. The bacmid DNA containing the recombinant baculovirus genome is then isolated using common techniques.

The illustrative PFASTBAC vector can be modified to a considerable degree. For example, the polyhedrin promoter can be removed and substituted with the baculovirus basic protein promoter (also known as Pcor, p6.9 or MP promoter) which is expressed earlier in the baculovirus infection, and has been shown to be advantageous for expressing secreted proteins (see, for example, Hill-Perkins and Possee, *J. Gen. Virol* 71:971 (1990), Bonning, et al., *J. Gen. Virol.* 75:1551 (1994), and Chazenbalk and Rapoport, *J. Biol. Chem.* 270:1543 (1995). In such transfer vector constructs, a short or long version of the basic protein promoter can be used. Moreover, transfer vectors can be constructed which replace the native interferon-ε secretory signal sequences with secretory signal sequences derived from insect proteins. For example, a secretory signal sequence from Ecdysteroid Glucosyltransferase (EGT), honey bee Melittin (Invitrogen Corporation; Carlsbad, Calif.), or baculovirus gp67 (PharMingen: San Diego, Calif.) can be used in constructs to replace the native interferon-ε secretory signal sequence.

The recombinant virus or bacmid is used to transfect host cells. Suitable insect host cells include cell lines derived from IPLB-Sf-21, a *Spodoptera frugiperda* pupal ovarian cell line, such as Sf9 (ATCC CRL 1711), Sf21AE, and Sf21 (Invitrogen Corporation; San Diego, Calif.), as well as Drosophila Schneider-2 cells, and the HIGH FIVEO cell line (Invitrogen) derived from *Trichoplusia ni* (U.S. Pat. No. 5,300,435). Commercially available serum-free media can be used to grow and to maintain the cells. Suitable media are Sf900 II™ (Life Technologies) or ESF 921™ (Expression Systems) for the Sf9 cells; and Ex-cell0405™ (JRH Biosciences, Lenexa, Kans.) or Express FiveO™ (Life Technologies) for the *T. ni* cells. When recombinant virus is used, the cells are typically grown up from an inoculation density of approximately $2-5\times10^5$ cells to a density of $1-2\times10^6$ cells at which time a recombinant viral stock is added at a multiplicity of infection (MOI) of 0.1 to 10, more typically near 3.

Established techniques for producing recombinant proteins in baculovirus systems are provided by Bailey et al., "Manipulation of Baculovirus Vectors," in *Methods in Molecular Biology, Volume 7: Gene Transfer and Expression Protocols,* Murray (ed.), pages 147–168 (The Humana Press, Inc. 1991), by Patel et al., "The baculovirus expression system," in *DNA Cloning 2: Expression Systems, 2nd Edition,* Glover et al. (eds.), pages 205–244 (Oxford University Press 1995), by Ausubel (1995) at pages 16–37 to 16–57, by Richardson (ed.), *Baculovirus Expression Protocols* (The Humana Press, Inc. 1995), and by Lucknow, "Insect Cell Expression Technology," in *Protein Engineering: Principles and Practice,* Cleland et al. (eds.), pages 183–218 (John Wiley & Sons, Inc. 1996).

Fungal cells, including yeast cells, can also be used to express the genes described herein. Yeast species of particular interest in this regard include *Saccharomyces cerevisiae, Pichia pastoris,* and *Pichia methanolica.* Suitable promoters for expression in yeast include promoters from GAL1 (galactose), PGK (phosphoglycerate kinase), ADH (alcohol dehydrogenase), AOX1 (alcohol oxidase), HIS4 (histidinol dehydrogenase), and the like. Many yeast cloning vectors have been designed and are readily available. These vectors include YIp-based vectors, such as YIp5, YRp vectors, such as YRp17, YEp vectors such as YEp13 and YCp vectors, such as YCp19. Methods for transforming *S. cerevisiae* cells with exogenous DNA and producing recombinant polypeptides therefrom are disclosed by, for example, Kawasaki, U.S. Pat. No. 4,599,311, Kawasaki et al., U.S. Pat. No. 4,931,373, Brake, U.S. Pat. No. 4,870,008, Welch et al., U.S. Pat. No. 5,037,743, and Murray et al., U.S. Pat. No. 4,845,075. Transformed cells are selected by phenotype determined by the selectable marker, commonly drug resistance or the ability to grow in the absence of a particular nutrient (e.g., leucine). A preferred vector system for use in *Saccharomyces cerevisiae* is the POT1 vector system disclosed by Kawasaki et al. (U.S. Pat. No. 4,931,373), which allows transformed cells to be selected by growth in glucose-containing media. Additional suitable promoters and terminators for use in yeast include those from glycolytic enzyme genes (see, e.g., Kawasaki, U.S. Pat. No. 4,599,311, Kingsman et al., U.S. Pat. No. 4,615,974, and Bitter, U.S. Pat. No. 4,977,092) and alcohol dehydrogenase genes. See also U.S. Pat. Nos. 4,990,446, 5,063,154, 5,139,936, and 4,661,454.

Transformation systems for other yeasts, including *Hansenula polymorpha, Schizosaccharomyces pombe, Kluyveromyces lactis, Kluyveromyces fragilis, Ustilago maydis, Pichia pastoris, Pichia methanolica, Pichia guillermondii* and *Candida maltosa* are known in the art. See, for example, Gleeson et al., *J. Gen. Microbiol.* 132:3459 (1986), and Cregg, U.S. Pat. No. 4,882,279. Aspergillus cells may be utilized according to the methods of McKnight et al., U.S. Pat. No. 4,935,349. Methods for transforming *Acremonium chrysogenum* are disclosed by Sumino et al., U.S. Pat. No. 5,162,228. Methods for transforming Neurospora are disclosed by Lambowitz, U.S. Pat. No. 4,486,533.

For example, the use of *Pichia methanolica* as host for the production of recombinant proteins is disclosed by Raymond, U.S. Pat. No. 5,716,808, Raymond, U.S. Pat. No. 5,736,383, Raymond et al., *Yeast* 14:11–23 (1998), and in international publication Nos. WO 97/17450, WO 97/17451, WO 98/02536, and WO 98/02565. DNA molecule; for use in transforming *P. methanolica* will commonly be prepared as double-stranded, circular plasmids, which are preferably linearized prior to transformation. For polypeptide production in *P. methanolica,* it is preferred that the promoter and terminator in the plasmid be that of a *P. methanolica* gene, such as a *P. methanolica* alcohol utilization gene (AUG1 or AUG2). Other useful promoters include those of the dihydroxyacetone synthase (DHAS), formate dehydrogenase (FMD), and catalase (CAT) genes. To facilitate integration of the DNA into the host chromosome, it is preferred to have the entire expression segment of the plasmid flanked at both ends by host DNA sequences. A preferred selectable marker for use in *Pichia methanolica* is a *P. methanolica* ADE2 gene, which encodes phosphoribosyl-5-aminoimidazole carboxylase (AIRC; EC 4.1.1.21), and which allows ade2 host cells to grow in the absence of adenine. For large-scale, industrial processes where it is desirable to minimize the use of methanol, it is preferred to use host cells in which both methanol utilization genes (AUG1 and AUG2) are deleted. For production of secreted proteins, host cells deficient in vacuolar protease genes (PEP4 and PRB1) are preferred. Electroporation is used to facilitate the introduction of a plasmid containing DNA encoding a polypeptide of interest into *P. methanolica* cells. *P. methanolica* cells can be transformed by electroporation using an exponentially decaying, pulsed electric field having a field strength of from 2.5 to 4.5 kV/cm, preferably about 3.75 kV/cm, and a time constant (t) of from 1 to 40 milliseconds, most preferably about 20 milliseconds.

Expression vectors can also be introduced into plant protoplasts, intact plant tissues, or isolated plant cells. Methods for introducing expression vectors into plant tissue include the direct infection or co-cultivation of plant tissue with *Agrobacterium tumefaciens,* microprojectile-mediated delivery, DNA injection, electroporation, and the like. See, for example, Horsch et al., *Science* 227:1229 (1985), Klein et al., *Biotechnology* 10:268 (1992), and Miki et al., "Procedures for Introducing Foreign DNA into Plants," in *Methods in Plant Molecular Biology and Biotechnology*, Glick et al. (eds.), pages 67–88 (CRC Press, 1993).

Alternatively, interferon-ε genes can be expressed in prokaryotic host cells. Suitable promoters that can be used to express interferon-ε polypeptides in a prokaryotic host are well-known to those of skill in the art and include promoters capable of recognizing the T4, T3, Sp6 and T7 polymerases, the $P_R$ and $P_L$ promoters of bacteriophage lambda, the trp, recA, heat shock, lacUV5, tac, lpp-lacSpr, phoA, and lacZ promoters of *E. coli*, promoters of *B. subtilis*, the promoters of the bacteriophages of Bacillus, Streptomyces promoters, the int promoter of bacteriophage lambda, the bla promoter of pBR322, and the CAT promoter of the chloramphenicol acetyl transferase gene. Prokaryotic promoters have been reviewed by Glick, *J. Ind. Microbiol.* 1:277 (1987), Watson et al., *Molecular Biology of the Gene*, 4th Ed (Benjamin Cuinnins 1987), and by Ausubel et al. (1995).

Preferred prokaryotic hosts include *E. coli* and *Bacillus subtilus*. Suitable strains of *E. coli* include BL21(DE3), BL21(DE3)pLysS, BL21(DE3)pLysE, DH1, DH4I, DH5, DH5I, DH5IF', DH5IMCR, DH10B, DH10B/p3, DH11S, C600, HB101, JM101, JM105, JM109, JM110, K38, RR1, Y1088, Y1089, CSH18, ER1451, and ER1647 (see, for example, Brown (ed.), *Molecular Biology Labfax* (Academic Press 1991)). Suitable strains of *Bacillus subtilus* include BR151, YB886, MI119, MI120, and B170 (see, for example, Hardy, "Bacillus Cloning Methods," in *DNA Cloning: A Practical Approach*, Glover (ed.) (IRL Press 1985)).

When expressing an interferon-ε polypeptide in bacteria such as *E. coli*, the polypeptide may be retained in the cytoplasm, typically as insoluble granules, or may be directed to the periplasmic space by a bacterial secretion sequence. In the former case, the cells are lysed, and the granules are recovered and denatured using, for example, guanidine isothiocyanate or urea. The denatured polypeptide can then be refolded and dimerized by diluting the denaturant, such as by dialysis against a solution of urea and a combination of reduced and oxidized glutathione, followed by dialysis against a buffered saline solution. In the latter case, the polypeptide can be recovered from the periplasmic space in a soluble and functional form by disrupting the cells (by, for example, sonication or osmotic shock) to release the contents of the periplasmic space and recovering the protein, thereby obviating the need for denaturation and refolding.

Methods for expressing proteins in prokaryotic hosts are well-known to those of skill in the art (see, for example, Williams et al., "Expression of foreign proteins in *E. coli* using plasmid vectors and purification of specific polyclonal antibodies," in *DNA Cloning 2: Expression Systems*, 2nd Edition, Glover et al. (eds.), page 15 (Oxford University Press 1995), Ward et al., "Genetic Manipulation and Expression of Antibodies," in *Monoclonal Antibodies: Principles and Applications*, page 137 (Wiley-Liss, Inc. 1995), and Georgiou, "Expression of Proteins in Bacteria," in *Protein Engineering: Principles and Practice*, Cleland et al. (eds.), page 101 (John Wiley & Sons, Inc. 1996)).

Standard methods for introducing expression vectors into bacterial, yeast, insect, and plant cells are provided, for example, by Ausubel (1995).

General methods for expressing and recovering foreign protein produced by a mammalian cell system are provided by, for example, Etcheverry, "Expression of Engineered Proteins in Mammalian Cell Culture," in *Protein Engineering: Principles and Practice*, Cleland et al. (eds.), pages 163 (Wiley-Liss, Inc. 1996). Standard techniques for recovering protein produced by a bacterial system is provided by, for example, Grisshammer et al., "Purification of over-produced proteins from *E. coli* cells," in *DNA Cloning 2: Expression Systems*, 2nd Edition, Glover et al. (eds.), pages 59–92 (Oxford University Press 1995). Established methods for isolating recombinant proteins from a baculovirus system are described by Richardson (ed.), *Baculovirus Expression Protocols* (The Humana Press, Inc. 1995).

In particular, the art of producing interferon polypeptides from cultured cells is well-established due to the great interest in interferon pharmaceuticals. For example, recombinant interferons have been produced by bacteria, yeasts, plant cells, insect cells, vertebrate cells, as well as in cell-free systems (Horisberger and Di Marco, *Pharmac. Ther.* 66:507 (1995)). Reviews of methods for producing recombinant interferon are provided, for example, by Edge and Camble, *Biotechnol. Genet. Eng. Rev.* 2:215 (1984), Langer and Pestka, *J. Invest. Dermatol* 83:128s (1984), Pestka, *Semin. Hematol.* 23:27 (1986), Baron and Narula, *Crit. Rev. Biotechnol.* 10:179 (1990), and Croughan et al., *Bioprocess Technol* 21:377 (1995). The production of human interferon in Chinese hamster ovary (CHO) cells has been described by McCormick et al., U.S. Pat. No. 5,795,779, while Dorin et al., U.S. Pat. No. 5,814,485, teach methods for producing interferon in *E. coli*.

As an alternative, polypeptides of the present invention can be synthesized by exclusive solid phase synthesis, partial solid phase methods, fragment condensation or classical solution synthesis. These synthesis methods are well-known to those of skill in the art (see, for example, Merrifield, *J. Am. Chem. Soc.* 85:2149 (1963), Stewart et al., "Solid Phase Peptide Synthesis" (2nd Edition), (Pierce Chemical Co. 1984), Bayer and Rapp, *Chem. Pept. Prot.* 3:3 (1986), Atherton et al., *Solid Phase Peptide Synthesis: A Practical Approach* (IRL Press 1989), Fields and Colowick, "Solid-Phase Peptide Synthesis," *Methods in Enzymology Volume* 289 (Academic Press 1997), and Lloyd-Williams et al., *Chemical Approaches to the Synthesis of Peptides and Proteins* (CRC Press, Inc. 1997)). Variations in total chemical synthesis strategies, such as "native chemical ligation" and "expressed protein ligation" are also standard (see, for example, Dawson et al., *Science* 266:776 (1994), Hackeng et al., *Proc. Nat'l Acad. Sci. USA* 94:7845 (1997), Dawson, *Methods Enzymol.* 287: 34 (1997), Muir et al, *Proc. Nat'l Acad. Sci. USA* 95:6705 (1998), and Severinov and Muir, *J. Biol. Chem.* 273:16205 (1998)).

7. Isolation of Interferon-ε Polypeptides

It is preferred to purify the polypeptides of the present invention to at least about 80% purity, more preferably to at least about 90% purity, even more preferably to at least about 95% purity, or even greater than 95% purity with respect to contaminating macromolecules, particularly other proteins and nucleic acids, and free of infectious and pyrogenic agents. The polypeptides of the present invention may also be purified to a pharmaceutically pure state, which is greater than 99.9% pure. Preferably, a purified polypeptide is substantially free of other polypeptides, particularly other polypeptides of animal origin.

Fractionation and/or conventional purification methods can be used to obtain preparations of interferon-ε purified from natural sources (e.g., coronary artery smooth muscle tissue, placental tissue, uterine tissue, or tracheal tissue), and recombinant interferon-ε polypeptides and fusion interferon-ε polypeptides purified from recombinant host cells. In general, ammonium sulfate precipitation and acid or chaotrope extraction may be used for fractionation of samples. Exemplary purification steps may include hydroxyapatite, size exclusion, FPLC and reverse-phase high performance liquid chromatography. Suitable chromatographic media include derivatized dextrans, agarose, cellulose, polyacrylamide, specialty silicas, and the like. PEI, DEAE, QAE and Q derivatives are preferred. Exemplary chromatographic media include those media derivatized with phenyl, butyl, or octyl groups, such as Phenyl-Sepharose FF (Pharmacia), Toyopearl butyl 650 (Toso Haas, Montgomeryville, Pa.), Octyl-Sepharose (Pharmacia) and the like; or polyacrylic resins, such as Amberchrom CG 71 (Toso Haas) and the like. Suitable solid supports include glass beads, silica-based resins, cellulosic resins, agarose beads, cross-linked agarose beads, polystyrene beads, cross-linked polyacrylamide resins and the like that are insoluble under the conditions in which they are to be used. These supports may be modified with reactive groups that allow attachment of proteins by amino groups, carboxyl groups, sulfhydryl groups, hydroxyl groups and/or carbohydrate moieties.

Examples of coupling chemistries include cyanogen bromide activation, N-hydroxysuccinimide activation, epoxide activation, sulfhydryl activation, hydrazide activation, and carboxyl and amino derivatives for carbodiimide coupling chemistries. These and other solid media are well known and widely used in the art, and are available from commercial suppliers. Selection of a particular method for polypeptide isolation and purification is a matter of routine design and is determined in part by the properties of the chosen support. See, for example, *Affinity Chromatography: Principles & Methods* (Pharmacia LKB Biotechnology 1988), and Doonan, *Protein Purification Protocols* (The Humana Press 1996).

Additional variations in interferon-ε isolation and purification can be devised by those of skill in the art. For example, anti-interferon-ε antibodies, obtained as described below, can be used to isolate large quantities of protein by immunoaffinity purification. The use of monoclonal antibody columns to purify interferons from recombinant cells and from natural sources has been described, for example, by Staehelin et al., *J. Biol. Chem.* 256:9750 (1981), and by Adolf et al., *J. Biol. Chem.* 265:9290 (1990). Moreover, methods for binding ligands, such as interferon-ε, to receptor polypeptides bound to support media are well known in the art.

The polypeptides of the present invention can also be isolated by exploitation of particular properties. For example, immobilized metal ion adsorption (IMAC) chromatography can be used to purify histidine-rich proteins, including those comprising polyhistidine tags. Briefly, a gel is first charged with divalent metal ions to form a chelate (Sulkowski, *Trends in Biochem.* 3:1 (1985)). Histidine-rich proteins will be adsorbed to this matrix with differing affinities, depending upon the metal ion used, and will be eluted by competitive elution, lowering the pH, or use of strong chelating agents. Other methods of purification include purification of glycosylated proteins by lectin affinity chromatography and ion exchange chromatography (M. Deutscher, (ed.), *Meth. Enzymol.* 182:529 (1990)). For example, the interferon-γ isolation method of Rinderknecht et al., *J. Biol. Chem.* 259:6790 (1984), requires the binding of the interferon with concanavalin A-sepharose in one step. Within additional embodiments of the invention, a fusion of the polypeptide of interest and an affinity tag (e.g., maltose-binding protein, an immunoglobulin domain) may be constructed to facilitate purification.

Interferon-ε polypeptides or fragments thereof may also be prepared through chemical synthesis, as described below.

Interferon-ε polypeptides may be monomers or multimers; glycosylated or non-glycosylated; PEGylated or non-PEGylated; and may or may not include an initial methionine amino acid residue.

Peptides and polypeptides of the present invention comprise at least six, preferably at least nine, and more preferably at least 15 contiguous amino acid residues of SEQ ID NO:2, SEQ ID NO:5, or SEQ ID NO:24. Within certain embodiments of the invention, the polypeptides comprise 20, 30, 40, 50, 100, or more contiguous residues of these amino acid sequences. Nucleic acid molecules encoding such peptides and polypeptides are useful as polymerase chain reaction primers and probes.

8. Assays for Interferon-ε, Its Analogs, and the Interferon-ε Receptor

As described above, the disclosed polypeptides can be used to construct interferon-ε variants. An interferon-ε variant will possess an interferon-ε biological activity, as determined by the in vitro assays described below. A polypeptide produced by an interferon-ε variant gene is considered to be an interferon-ε agonist if the polypeptide exhibits a biological activity (e.g., anti-viral or anti-proliferative activity).

On the other hand, an interferon-ε variant gene product that lacks biological activity may be an interferon-ε antagonist. These biologically-inactive interferon-ε variants can be initially identified on the basis of hybridization analysis, sequence identity determination, or by the ability to specifically bind anti-interferon-ε antibody. An interferon-ε antagonist can be further characterized by its ability to inhibit the biological response induced by interferon-ε or by an interferon-ε agonist. This inhibitory effect may result, for example, from the competitive or non-competitive binding of the antagonist to the interferon-ε receptor.

Interferon-ε, its agonists and antagonists are valuable in both in vivo and in vitro uses. As an illustration, cytokines can be used as components of defined cell culture media, alone or in combination with other cytokines and hormones, to replace serum that is commonly used in cell culture. In particular, interferons have been shown to stimulate the production of other biologically active polypeptides, such as interleukin-1, by cultured cells, which can be isolated from the culture (see, for example, Danis et al., *Clin. Exp. Immunol.* 80:435 (1990)). Interferons have also been shown to induce the expression of antigens by cultured cells (see, for example, Auth et al., *Hepatology* 18:546 (1993), Guadagni et al., *Int. J. Biol. Markers* 9:53 (1994), Girolomoni et al., *Eur. J. Immunol.* 25:2163 (1995), and Maciejewski et al., *Blood* 85:3183 (1995). This activity enhances the ability to identify new tumor associated antigens in vitro. Moreover, the ability of interferons to augment the level of expression of human tumor antigens indicates that interferons can be useful in an adjuvant setting for immunotherapy or immunoscintigraphy using anti-tumor antigen antibodies (Guadagni et al., *Cancer Immunol. Immunother.* 26:222 (1988); Guadagni et al., *Int. J. Biol. Markers* 9:53 (1994)).

Antagonists are also useful a research reagents for characterizing sites of interaction between interferon-ε and its receptor. In a therapeutic setting, pharmaceutical compositions comprising interferon-ε antagonists can be used to inhibit interferon-ε activity.

One general class of interferon-ε analogs are agonists or antagonists having an amino acid sequence that is a mutation of the amino acid sequences disclosed herein. Another general class of interferon-ε analogs is provided by anti-idiotype antibodies, and fragments thereof, as described below. Moreover, recombinant antibodies comprising anti-idiotype variable domains can be used as analogs (see, for example, Monfardini et al., *Proc. Assoc. Am. Physicians* 108:420 (1996)). Since the variable domains of anti-idiotype interferon-ε antibodies mimic interferon-ε, these domains can provide either interferon-ε agonist or antagonist activity. As an illustration, Lim and Langer, *J. Interferon Res.* 13:295 (1993), describe anti-idiotypic interferon-α antibodies that have the properties of either interferon-α agonists or antagonists.

A third approach to identifying interferon-ε analogs is provided by the use of combinatorial libraries. Methods for constructing and screening phage display and other combinatorial libraries are provided, for example, by Kay et al., *Phage Display of Peptides and Proteins* (Academic Press 1996), Verdine, U.S. Pat. No. 5,783,384, Kay, et. al., U.S. Pat. No. 5,747,334, and Kaufman et al., U.S. Pat. No. 5,723,323.

One assay that can be used to measure interferon-ε biological activity is an interferon in vitro virus inhibition assay (see, for example, Familletti et al., *Methods in Enzymol.* 78:83 (1981)). As an illustration, a test sample is diluted in culture medium in the first well of a row of a microtiter plate to a final volume of 0.2 ml. Two-fold dilutions of the test sample are made by transferring 0.1 ml serially to the end of the row. Several wells on the plate contain 0.1 ml of culture medium without interferon-ε; these provide the virus and cell controls. Each well is seeded with about $3 \times 10^4$ cells/well of a cell line that forms a monolayer in culture and that is susceptible to the virus used in the assay. For example, the "WISH" human amnion cell line (ATCC No. CCL-25) would be suitable. The plate is incubated at 37° C. for one hour. With the exception of the cell control wells, each well is challenged with 3000 plaque-forming units of vesicular stomatic virus. The plate is then incubated at 37° C. for an additional 16 hours, or until a full cytopathic effect is noted in the virus control well that lacks interferon-ε. The medium is aspirated from the wells, and the cells are immediately fixed and stained with 0.1 ml of 0.5% crystal violet in 70% methanol. The amount of interferon-ε is calculated as the reciprocal of the dilution represented in the well in which 50% of the cell monolayer is protected by the interferon-ε. One unit of interferon-ε may be defined as the concentration of interferon-ε required to inhibit virus plaque formation by 50%.

Those of skill in the art can devise variations of this viral assay. For example, the WISH cells can be substituted with Madin Darby bovine kidney (MDBK; ATCC No. CCL-22). Alternatively, an assay can be performed with A549 human lung carcinoma cells (ATCC No. CCL-185), or a human glioblastoma cell line 86HG39, and encephalomyocarditis virus. See, for example, Roberts and Liu, "Interferon-ω," in *Human Cytokines, Volume II*, Aggarwal and Gutterman (eds.), pages 168–177 (Blackwell Science 1996), and Daubener et al., *J. Immunol. Methods* 168:39 (1994). In addition, Example 8 illustrates a viral assay with encephalomyocarditis virus and either mouse fibroblast cells (L929) and human cervical carcinoma cells (HeLa).

An alternative to the cytopathic effect assay is an assay that measures an inhibition of virus plaque formation in cultured cells infected with a virus, such as vesicular stomatitis virus (see, for example, Horisberger and de Startitzky, *J. Gen. Virol.* 68:945 (1987)). A third approach is to determine the reduction in virus yield by measuring the amount of virus released by infected cells, typically during a single growth cycle (see, for example, Stitz and Schellekens, *J. Gen. Virol.* 46:205 (1980)).

Another approach to evaluating interferon-ε activity is to use an assay that measures the inhibition of the proliferation of cultured human cells. An anti-proliferation assay is particularly useful to indicate the biological activity of an interferon in anti-tumor and immunomodulatory therapies. As an illustration, Mire-Sluis et al., *J. Immunol. Methods* 195:55 (1996), have described an anti-cytokine bioassay based on the ability of interferons to inhibit granulocyte-macrophage-colony-stimulating factor (GM-CSF)-induced proliferation of the erythroleukemic cell line TF-1 (ATCC No. CRL-2003). The assay can be performed within 24 hours, and the assay is sensitive to as little as 100–200 fg interferon. The assay may be varied, for example, by using erytliropoietin-induced proliferation of TF-1 cells, or erythropoietin-induced proliferation of UT-7-EPO cells.

Example 7 illustrates the use of a cell proliferation assay to characterize the effect of murine interferon-ε on a human B cell lymphoma cell line. In this test, samples containing the interferon were incubated with Daudi cells, a human B lymphoblast cell line derived from Burkitt's lymphoma (ATCC No. CCL-213). The inhibition of cell proliferation was determined by measuring incorporation of $^3$H-thymidine by the Daudi cells.

Yet another general approach to measuring interferon-ε activity is based upon the interferon-mediated inhibition of the expression of *Eschericia coli* β-galactosidase in cells of genetically modified human glioblastoma cell line, as described by Hammerling et al., *J. Interferon Cytokine Res.* 18:451 (1998). These cells were stably transfected with a glial fibrillary acidic protein promoter sequence operatively linked with a lacZ promoter gene, and consequently, the recombinant cells produced β-galactosidase constitutively. However, human interferons selectively reduced β-galactosidase formation in a dose-dependent manner. This β-gal interferon assay is sensitive to picomolar concentrations of human interferon, and the assay can be used with both Type I and Type II interferons.

Additional methods for measuring interferon activity are known to those of skill in the art. For example, Uno et al., U.S. Pat. No. 5,766,864, describe a method of determining interferon activity by measuring the induction of 2'→5' oligoadenylate synthetase.

Alternatively, interferon activity can be detected by the induction of the expression of interferon-responsive genes using standard methods for mRNA detection, such as RT-PCR or an RNase protection assay. Various interferon-inducible proteins are described, for example, on pages 498 to 499 of De Maeyer and De Maeyer-Guignard, "Interferons," in *The Cytokine Handbook, 3$^{rd}$ Edition*, Thompson (ed.), pages 491–516 (Academic Press Ltd. 1998). Example 9 illustrates this general approach to identifying interferon-ε activity.

As a receptor ligand, the activity of interferon-ε can be measured by a silicon-based biosensor microphysiometer which measures the extracellular acidification rate or proton excretion associated with receptor binding and subsequent cellular responses. An exemplary device is the CYTOSEN-SOR Microphysiometer manufactured by Molecular Devices Corp. (Sunnyvale, Calif.). A variety of cellular responses, such as cell proliferation, ion transport, energy production, inflammatory response, regulatory and receptor activation, and the like, can be measured by this method (see, for example, McConnell et al., *Science* 257:1906 (1992), Pitchford et al., *Meth. Enzymol.* 228:84 (1997), Arimilli et al., *J. Immunol. Meth.* 212:49 (1998), and Van Liefde et al., *Eur. J. Pharmacol.* 346:87 (1998)). Moreover, the microphysiometer can be used for assaying adherent or non-adherent eukaryotic or prokaryotic cells.

Since energy metabolism is coupled with the use of cellular ATP, any event which alters cellular ATP levels, such as receptor activation and the initiation of signal transduction, will cause a change in cellular acid section. An early event in interferon signal transduction is protein phosphorylation, which requires ATP. By measuring extracellular acidification changes in cell media over time, therefore, the microphysiometer directly measures cellular responses to various stimuli, including interferon-ε, its agonists, or antagonists. Preferably, the microphysiometer is used to measure responses of an interferon-ε responsive eukaryotic cell, compared to a control eukaryotic cell that does not respond to interferon-ε polypeptide. Interferon-ε responsive eukaryotic cells comprise cells into which a receptor for interferon-ε has been transfected to create a cell that is responsive to interferon-ε, or cells that are naturally responsive to interferon-ε. Suitable interferon-ε responsive cells include HeLa cells, Daudi cells, L929 cells (ATCC No. CCL-1), human lung carcinoma cells (e.g., A549 cells; ATCC No. CCL-185) cells, and normal human diploid fibroblasts cells (e.g., FS-4 cells; Vilcek et al., *J. Exp. Med.* 163:632 (1986)). Interferon-ε modulated cellular responses are measured by a change (e.g., an increase or decrease in extracellular acidification) in the response of cells exposed to interferon-ε, compared with control cells that have not been exposed to interferon-ε.

Accordingly, a microphysiometer can be used to identify cells, tissues, or cell lines which respond to an interferon-ε stimulated pathway, and which express a functional interferon-ε receptor. As an illustration, cells that express a functional interferon-ε receptor can be identified by (a) providing test cells, (b) incubating a first portion of the test cells in the absence of interferon-ε, (c) incubating a second portion of the test cells in the presence of interferon-ε, and (d) detecting a change (e.g., an increase or decrease in extracellular acidification rate, as measured by a microphysiometer) in a cellular response of the second portion of the test cells, as compared to the first portion of the test cells, wherein such a change in cellular response indicates that the test cells express a functional interferon-ε receptor. An additional negative control may be included in which a portion of the test cells is incubated with interferon-ε and an anti-interferon-ε antibody to inhibit the binding of interferon-ε with its cognate receptor.

The microphysiometer also provides one means to identify interferon-ε agonists. For example, agonists of interferon-ε can be identified by a method, comprising the steps of (a) providing cells responsive to interferon-ε, (b) incubating a first portion of the cells in the absence of a test compound, (c) incubating a second portion of the cells in the presence of a test compound, and (d) detecting a change, for example, an increase or diminution, in a cellular response of the second portion of the cells as compared to the first portion of the cells, wherein such a change in cellular response indicates that the test compound is an interferon-ε agonist. An illustrative change in cellular response is a measurable change in extracellular acidification rate, as measured by a microphysiometer. Moreover, incubating a third portion of the cells in the presence of interferon-ε and in the absence of a test compound can be used as a positive control for the interferon-ε responsive cells, and as a control to compare the agonist activity of a test compound with that of interferon-ε. An additional control may be included in which a portion of the cells is incubated with a test compound (or interferon-ε) and an anti-interferon-ε antibody to inhibit the binding of the test compound (or interferon-ε) with the interferon-ε receptor.

The microphysiometer also provides a means to identify interferon-ε antagonists. For example, interferon-ε antagonists can be identified by a method, comprising the steps of (a) providing cells responsive to interferon-ε, (b) incubating a first portion of the cells in the presence of interferon-ε and in the absence of a test compound, (c) incubating a second portion of the cells in the presence of both interferon-ε and the test compound, and (d) comparing the cellular responses of the first and second cell portions, wherein a decreased response by the second portion, compared with the response of the first portion, indicates that the test compound is an interferon-ε antagonist. An illustrative change in cellular response is a measurable change extracellular acidification rate, as measured by a microphysiometer.

Interferon-ε, its analogs, and anti-iodiotype interferon-ε antibodies can be used to identify and to isolate interferon-ε receptors. For example, proteins and peptides of the present invention can be immobilized on a column and used to bind receptor proteins from membrane preparations that are run over the column (Hermanson et al. (eds.), *Immobilized Affinity Ligand Techniques,* pages 195–202 (Academic Press 1992)). Radiolabeled or affinity labeled interferon-ε polypeptides can also be used to identify or to localize interferon-ε receptors in a biological sample (see, for example, Deutscher (ed.), *Methods in Enzymol.,* vol. 182, pages 721–37 (Academic Press 1990); Brunner et al., *Ann. Rev. Biochem.* 62:483 (1993); Fedan et al., *Biochem. Pharmacol.* 33:1167 (1984)). Also see, Varthakavi and Minocha, *J. Gen. Virol.* 77:1875 (1996), who describe the use of anti-idiotype antibodies for receptor identification.

In addition, a solid phase system can be used to identify an interferon-ε receptor, or an agonist or antagonist of an interferon-ε receptor. For example, an interferon-ε polypeptide or interferon-ε fusion protein can be immobilized onto the surface of a receptor chip of a commercially available biosensor instrument (BIACORE, Biacore AB; Uppsala, Sweden). The use of this instrument is disclosed, for example, by Karlsson, *Immunol. Methods* 145:229 (1991), and Cunningham and Wells, *J. Mol. Biol.* 234:554 (1993).

As an illustration, an interferon-ε polypeptide or fusion protein is covalently attached, using amine or sulfhydryl chemistry, to dextran fibers that are attached to gold film within a flow cell. A test sample is then passed through the cell. If a receptor is present in the sample, it will bind to the immobilized polypeptide or fusion protein, causing a change in the refractive index of the medium, which is detected as a change in surface plasmon resonance of the gold film. This system allows the determination of on- and off-rates, from which binding affinity can be calculated, and assessment of stoichiometry of binding. This system can also be used to examine antibody-antigen interactions, and the interactions of other complement/anti-complement pairs.

9. Production of Antibodies to Interferon-ε Proteins

Antibodies to interferon-ε can be obtained, for example, using the product of an interferon-ε expression vector or interferon-ε isolated from a natural source as an antigen. Particularly useful anti-interferon-ε antibodies "bind specifically" with interferon-ε. Antibodies are considered to be specifically binding if the antibodies exhibit at least one of the following two properties; (1) antibodies bind to interferon-ε with a threshold level of binding activity, and (2) antibodies do not significantly cross-react with polypeptides related to interferon-ε.

With regard to the first characteristic, antibodies specifically bind if they bind to an interferon-ε polypeptide, peptide or epitope with a binding affinity ($K_a$) of $10^6$ $M^{-1}$ or greater, preferably $10^7$ $M^{-1}$ or greater, more preferably $10^8$ $M^{-1}$ or greater, and most preferably $10^9$ $M^{-1}$ or greater. The binding affinity of an antibody can be readily determined by one of ordinary skill in the art, for example, by Scatchard analysis (Scatchard, *Ann. NY Acad. Sci.* 51:660 (1949)). With regard to the second characteristic, antibodies do not significantly cross-react with related polypeptide molecules, for example, if they detect interferon-ε, but not known related polypeptides using a standard Western blot analysis. Examples of known related polypeptides are orthologs and proteins from the same species that are members of a protein family. For example, specifically-binding anti-human interferon-ε antibodies bind with human interferon-ε, but not with polypeptides such as interferon-α, interferon-β, interferon-γ, interferon-δ, interferon-ω, or interferon-Y. Suitable antibodies include antibodies that bind with interferon-ε in regions having a low sequence similarity with other interferons. As illustrated in FIG. 1, suitable regions of human interferon-ε include amino acids 104 to 149 of SEQ ID NO:2, and amino acids 173 to 208 of SEQ ID NOs:2 or 5. Similarly, specifically-binding anti-murine interferon-ε antibodies bind with murine interferon-ε, but not with polypeptides such as interferon-α, interferon-β, interferon-γ, interferon-δ, interferon-ω, or interferon-τ. Highly specifically binding anti-human interferon-ε antibodies bind with human interferon-ε, but not murine interferon-ε, while highly specific anti-murine interferon-ε antibodies bind with murine interferon-ε, but not with human interferon-ε.

Anti-interferon-ε antibodies can be produced using antigenic interferon-ε epitope-bearing peptides and polypeptides. Antigenic epitope-bearing peptides and polypeptides of the present invention contain a sequence of at least nine, preferably between 15 to about 30 amino acids contained within SEQ ID NO:2, SEQ ID NO:5, or SEQ ID NO:24. However, peptides or polypeptides comprising a larger portion of an amino acid sequence of the invention, containing from 30 to 50 amino acids, or any length up to and including the entire amino acid sequence of a polypeptide of the invention, also are useful for inducing antibodies that bind with interferon-ε. It is desirable that the amino acid sequence of the epitope-bearing peptide is selected to provide substantial solubility in aqueous solvents (i.e., the sequence includes relatively hydrophilic residues, while hydrophobic residues are preferably avoided). Moreover, amino acid sequences containing proline residues may be also be desirable for antibody production.

As an illustration, potential antigenic sites in human interferon-ε were identified using the Jameson-Wolf method, Jameson and Wolf, *CABIOS* 4:181, (1988), as implemented by the PROTEAN program (version 3.14) of LASERGENE (DNASTAR; Madison, Wis.). Default parameters were used in this analysis.

The Jameson-Wolf method predicts potential antigenic determinants by combining six major subroutines for protein structural prediction. Briefly, the Hopp-Woods method, Hopp et al., *Proc. Nat'l Acad. Sci. USA* 78:3824 (1981), was first used to identify amino acid sequences representing areas of greatest local hydrophilicity (parameter: seven residues averaged). In the second step, Emini's method, Emini et al., *J. Virology* 55:836 (1985), was used to calculate surface probabilities (parameter: surface decision threshold (0.6)=1). Third, the Karplus-Schultz method, Karplus and Schultz, *Naturwissenschaften* 72:212 (1985), was used to predict backbone chain flexibility (parameter: flexibility threshold (0.2)=1). In the fourth and fifth steps of the analysis, secondary structure predictions were applied to the data using the methods of Chou-Pasman, Chou, "Prediction of Protein Structural Classes from Amino Acid Composition," in *Prediction of Protein Structure and the Principles of Protein Conformation*, Fasman (ed.), pages 549–586 (Plenum Press 1990), and Garnier-Robson, Garnier et al., *J. Mol. Biol.* 120:97 (1978) (Chou-Fasman parameters: conformation table=64 proteins; α region threshold=103; β region threshold=105; Garnier-Robson parameters: α and β decision constants=0). In the sixth subroutine, flexibility parameters and hydropathy/solvent accessibility factors were combined to determine a surface contour value, designated as the "antigenic index." Finally, a peak broadening function was applied to the antigenic index, which broadens major surface peaks by adding 20, 40, 60, or 80% of the respective peak value to account for additional free energy derived from the mobility of surface regions relative to interior regions. This calculation was not applied, however, to any major peak that resides in a helical region, since helical regions tend to be less flexible.

The results of this analysis indicated that the following amino acid sequences of SEQ ID NO:2 would provide suitable antigenic peptides: amino acids 33 to 39 of SEQ ID NO:2 ("antigenic peptide 1"), amino acids 33 to 38 ("antigenic peptide 2"), 34 to 39 ("antigenic peptide 3"), amino acids 54 to 61 ("antigenic peptide 4"), amino acids 54 to 59 ("antigenic peptide 5"), amino acids 55 to 60 ("antigenic peptide 6"), amino acids 56 to 61 ("antigenic peptide 7"), amino acids 64 to 76 ("antigenic peptide 8"), amino acids 64 to 69 ("antigenic peptide 9"), amino acids 65 to 70 ("antigenic peptide 10"), amino acids 66 to 71 ("antigenic peptide 11"), amino acids 67 to 72 ("antigenic peptide 12"), amino acids 68 to 73 ("antigenic peptide 13"), amino acids 69 to 74 ("antigenic peptide 14"), amino acids 70 to 75 ("antigenic peptide 15"), amino acids 71 to 76 ("antigenic peptide 16"), amino acids 135 to 141 ("antigenic peptide 17"), amino acids 135 to 140 ("antigenic peptide 18"), amino acids 136 to 141 ("antigenic peptide 19"), amino acids 156 to 162 ("antigenic peptide 20"), amino acids 156 to 161 ("antigenic peptide 21"), amino acids 157 to 162 ("antigenic peptide 22"), amino acids 185 to 193 ("antigenic peptide 23"), amino acids 185 to 190 ("antigenic peptide 24"), amino acids 186 to 191 ("antigenic peptide 25"), amino acids 187 to 192 ("antigenic peptide 26"), amino acids 188 to 193 ("antigenic peptide 27"), and amino acids 203 to 208 ("antigenic peptide 28"). The present invention contemplates the use of any one of antigenic peptides 1 to 28 to generate antibodies to interferon-ε. The present invention also contemplates polypeptides comprising at least one of antigenic peptides 1 to 28.

Similarly, Jameson-Wolf analysis of a murine interferon-ε indicated that the following amino acid sequences of SEQ ID NO:24 would provide suitable antigenic peptides: amino acids 22 to 28 ("antigenic peptide 29"), amino acids 34 to 40 ("antigenic peptide 30"), 43 to 49 ("antigenic peptide 31"), amino acids 54 to 60 ("antigenic peptide 32"), amino acids 70 to 75 ("antigenic peptide 33"), amino acids 130 to 136 ("antigenic peptide 34"), amino acids 155 to 161 ("antigenic peptide 35"), and amino acids 186 to 192 ("antigenic peptide 36"). The present invention contemplates the use of any one of antigenic peptides 29 to 36 to generate antibodies to murine interferon-ε. The present invention also contemplates polypeptides comprising at least one of antigenic peptides 29 to 36.

Polyclonal antibodies to recombinant interferon-ε protein or to interferon-ε isolated from natural sources can be prepared using methods well-known to those of skill in the art. See, for example, Green et al., "Production of Polyclonal Antisera," in *Immunochemical Protocols* (Manson, ed.), pages 1–5 (Humana Press 1992), and Williams et al., "Expression of foreign proteins in *E. coli* using plasmid vectors and purification of specific polyclonal antibodies,"

in *DNA Cloning 2: Expression Systems, 2nd Edition,* Glover et al. (eds.), page 15 (Oxford University Press 1995). The immunogenicity of a interferon-ε polypeptide can be increased through the use of an adjuvant, such as alum (aluminum hydroxide) or Freund's complete or incomplete adjuvant. Polypeptides useful for immunization also include fusion polypeptides, such as fusions of interferon-ε or a portion thereof with an immunoglobulin polypeptide or with maltose binding protein. The polypeptide immunogen may be a full-length molecule or a portion thereof. If the polypeptide portion is "hapten-like," such portion may be advantageously joined or linked to a macromolecular carrier (such as keyhole limpet hemocyanin (KLH), bovine serum albumin (BSA) or tetanus toxoid) for immunization.

Although polyclonal antibodies are typically raised in animals such as horses, cows, dogs, chicken, rats, mice, rabbits, guinea pigs, goats, or sheep, an anti-interferon-ε antibody of the present invention may also be derived from a subhuman primate antibody. General techniques for raising diagnostically and therapeutically useful antibodies in baboons may be found, for example, in Goldenberg et al., international patent publication No. WO 91/11465, and in Losman et al., Int. *J. Cancer* 46:310 (1990).

Alternatively, monoclonal anti-interferon-ϵ antibodies can be generated. Rodent monoclonal antibodies to specific antigens may be obtained by methods known to those skilled in the art (see, for example, Kohler et al., *Nature* 256:495 (1975), Coligan et al. (eds.), *Current Protocols in Immunology, Vol.* 1, pages 2.5.1–2.6.7 (John Wiley & Sons 1991) ["Coligan"], Picksley et al., "Production of monoclonal antibodies against proteins expressed in *E. coli,* " in *DNA Cloning 2: Expression Systems, 2nd Edition,* Glover et al. (eds.), page 93 (Oxford University Press 1995)).

Briefly, monoclonal antibodies can be obtained by injecting mice with a composition comprising an interferon-ϵ gene product, verifying the presence of antibody production by removing a serum sample, removing the spleen to obtain B-lymphocytes, fusing the B-lymphocytes with myeloma cells to produce hybridomas, cloning the hybridomas, selecting positive clones which produce antibodies to the antigen, culturing the clones that produce antibodies to the antigen, and isolating the antibodies from the hybridoma cultures.

In addition, an anti-interferon-ϵ antibody of the present invention may be derived from a human monoclonal antibody. Human monoclonal antibodies are obtained from transgenic mice that have been engineered to produce specific human antibodies in response to antigenic challenge. In this technique, elements of the human heavy and light chain locus are introduced into strains of mice derived from embryonic stem cell lines that contain targeted disruptions of the endogenous heavy chain and light chain loci. The transgenic mice can synthesize human antibodies specific for human antigens, and the mice can be used to produce human antibody-secreting hybridomas. Methods for obtaining human antibodies from transgenic mice are described, for example, by Green et al., *Nature Genet.* 7:13 (1994), Lonberg et al., *Nature* 368:856 (1994), and Taylor et al., *Int. Immun.* 6:579 (1994).

Monoclonal antibodies can be isolated and purified from hybridoma cultures by a variety of well-established techniques. Such isolation techniques include affinity chromatography with Protein-A Sepharose, size-exclusion chromatography, and ion-exchange chromatography (see, for example, Coligan at pages 2.7.1–2.7.12 and pages 2.9.1–2.9.3; Baines et al., "Purification of Immunoglobulin G (IgG)," in *Methods in Molecular Biology,* Vol. 10, pages 79–104 (The Humana Press, Inc. 1992)).

For particular uses, it may be desirable to prepare fragments of anti-interferon-ϵ antibodies. Such antibody fragments can be obtained, for example, by proteolytic hydrolysis of the antibody. Antibody fragments can be obtained by pepsin or papain digestion of whole antibodies by conventional methods. As an illustration, antibody fragments can be produced by enzymatic cleavage of antibodies with pepsin to provide a 5S fragment denoted $F(ab')_2$. This fragment can be further cleaved using a thiol reducing agent to produce 3.5S Fab' monovalent fragments. Optionally, the cleavage reaction can be performed using a blocking group for the sulfhydryl groups that result from cleavage of disulfide linkages. As an alternative, an enzymatic cleavage using pepsin produces two monovalent Fab fragments and an Fc fragment directly. These methods are described, for example, by Goldenberg, U.S. Pat. No. 4,331,647, Nisonoff et al., *Arch Biochem. Biophys.* 89:230 (1960), Porter, *Biochem. J.* 73:119 (1959), Edelman et al., in *Methods in Enzymology* Vol. 1, page 422 (Academic Press 1967), and by Coligan at pages 2.8.1–2.8.10 and 2.10.–2.10.4.

Other methods of cleaving antibodies, such as separation of heavy chains to form monovalent light-heavy chain fragments, further cleavage of fragments, or other enzymatic, chemical or genetic techniques may also be used, so long as the fragments bind to the antigen that is recognized by the intact antibody.

For example, Fv fragments comprise an association of $V_H$ and $V_L$ chains. This association can be noncovalent, as described by Inbar et al., *Proc. Nat'l Acad. Sci. USA* 69:2659 (1972). Alternatively, the variable chains can be linked by an intermolecular disulfide bond or cross-linked by chemicals such as glutaraldehyde (see, for example, Sandhu, *Crit. Rev. Biotech.* 12:437 (1992)).

The Fv fragments may comprise $V_H$ and $V_L$ chains which are connected by a peptide linker. These single-chain antigen binding proteins (scFv) are prepared by constructing a structural gene comprising DNA sequences encoding the $V_H$ and $V_L$ domains which are connected by an oligonucleotide. The structural gene is inserted into an expression vector which is subsequently introduced into a host cell, such as *E. coli.* The recombinant host cells synthesize a single polypeptide chain with a linker peptide bridging the two V domains. Methods for producing scFvs are described, for example, by Whitlow et al., *Methods: A Companion to Methods in Enzymology* 2:97 (1991) (also see, Bird et al., *Science* 242:423 (1988), Ladner et al., U.S. Pat. No. 4,946,778, Pack et al., *Bio/Technology* 11:1271 (1993), and Sandhu, supra).

As an illustration, a scFV can be obtained by exposing lymphocytes to interferon-ϵ polypeptide in vitro, and selecting antibody display libraries in phage or similar vectors (for instance, through use of immobilized or labeled interferon-ϵ protein or peptide). Genes encoding polypeptides having potential interferon-ϵ polypeptide binding domains can be obtained by screening random peptide libraries displayed on phage (phage display) or on bacteria, such as *E. coli.* Nucleotide sequences encoding the polypeptides can be obtained in a number of ways, such as through random mutagenesis and random polynucleotide synthesis. These random peptide display libraries can be used to screen for peptides which interact with a known target which can be a protein or polypeptide, such as a ligand or receptor, a biological or synthetic macromolecule, or organic or inorganic substances. Techniques for creating and screening such random peptide display libraries are known in the art (Ladner et al., U.S. Pat. No. 5,221,409, Ladner et al., U.S. Pat. No. 4,946,778, Ladner et al., U.S. Pat. No. 5,403,484, Ladner et al., U.S. Pat. No. 5,571,698, and Kay et al., *Phage*

*Display of Peptides and Proteins* (Academic Press, Inc. 1996)) and random peptide display libraries and kits for screening such libraries are available commercially, for instance from CLONTECH Laboratories, Inc. (Palo Alto, Calif.), Invitrogen Inc. (San Diego, Calif.), New England Biolabs, Inc. (Beverly, Mass.), and Pharmacia LKB Biotechnology Inc. (Piscataway, N.J.). Random peptide display libraries can be screened using the interferon-ε sequences disclosed herein to identify proteins which bind to interferon-ε.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells (see, for example, Larrick et al., *Methods: A Companion to Methods in Enzymology* 2:106 (1991), Courtenay-Luck, "Genetic Manipulation of Monoclonal Antibodies," in *Monoclonal Antibodies: Production, Engineering and Clinical Application*, Ritter et al. (eds.), page 166 (Cambridge University Press 1995), and Ward et al., "Genetic Manipulation and Expression of Antibodies," in *Monoclonal Antibodies: Principles and Applications*, Birch et al., (eds.), page 137 (Wiley-Liss, Inc. 1995)).

Alternatively, an anti-interferon-ε antibody may be derived from a "humanized" monoclonal antibody. Humanized monoclonal antibodies are produced by transferring mouse complementary determining regions from heavy and light variable chains of the mouse immunoglobulin into a human variable domain. Typical residues of human antibodies are then substituted in the framework regions of the murine counterparts. The use of antibody components derived from humanized monoclonal antibodies obviates potential problems associated with the immunogenicity of murine constant regions. General techniques for cloning murine immunoglobulin variable domains are described, for example, by Orlandi et al., *Proc. Nat'l Acad. Sci. USA* 86:3833 (1989). Techniques for producing humanized monoclonal antibodies are described, for example, by Jones et al., *Nature* 321:522 (1986), Carter et al., *Proc. Nat'l Acad. Sci. USA* 89:4285 (1992), Sandhu, *Crit. Rev. Biotech.* 12:437 (1992), Singer et al., *J. Immun.* 150:2844 (1993), Sudhir (ed.), *Antibody Engineering Protocols* (Humana Press, Inc. 1995), Kelly, "Engineering Therapeutic Antibodies," in *Protein Engineering: Principles and Practice*, Cleland et al. (eds.), pages 399–434 (John Wiley & Sons, Inc. 1996), and by Queen et al., U.S. Pat. No. 5,693,762 (1997).

Polyclonal anti-idiotype antibodies can be prepared by immunizing animals with anti-interferon-ε antibodies or antibody fragments, using standard techniques. See, for example, Green et al., "Production of Polyclonal Antisera," in *Methods In Molecular Biology: Immunochemical Protocols*, Manson (ed.), pages 1–12 (Humana Press 1992). Also, see Coligan at pages 2.4.1–2.4.7. Alternatively, monoclonal anti-idiotype antibodies can be prepared using anti-interferon-ε antibodies or antibody fragments as immunogens with the techniques, described above. As another alternative, humanized anti-idiotype antibodies or subhuman primate anti-idiotype antibodies can be prepared using the above-described techniques. Methods for producing anti-idiotype antibodies are described, for example, by Irie, U.S. Pat. No. 5,208,146, Greene, et. al., U.S. Pat. No. 5,637,677, and Varthakavi and Minocha, *J. Gen. Virol.* 77:1875 (1996).

10. Diagnostic Application of Interferon-ε Nucleotide Sequences

Nucleic acid molecules can be used to detect the expression of an interferon-ε gene in a biological sample. Such probe molecules can include murine interferon-ε encoding sequences or human interferon-ε encoding sequences. For example, probe molecules include double-stranded nucleic acid molecules comprising the nucleotide sequence of SEQ ID NO:1, SEQ ID NO:4, or SEQ ID NO:23, or a fragment thereof, as well as single-stranded nucleic acid molecules having the complement of the nucleotide sequence of SEQ ID NO:1, SEQ ID NO:4, SEQ ID NO:23, or a fragment thereof. Probe molecules may be DNA, RNA, oligonucleotides, and the like.

Preferred probes bind with regions of the human interferon-ε gene or murine interferon-ε gene that have a low sequence similarity to comparable regions in other interferons. For example, suitable probes for human sequences will bind with at least one of the following portions of the nucleotide sequence of SEQ ID NO:1: nucleotides 763 to 900, and nucleotides 970 to 1077. As used herein, the term "portion" refers to at least eight nucleotides to at least 20 or more nucleotides.

In a basic assay, a single-stranded probe molecule is incubated with RNA, isolated from a biological sample, under conditions of temperature and ionic strength that promote base pairing between the probe and target interferon-ε RNA species. After separating unbound probe from hybridized molecules, the amount of hybrids is detected. Illustrative biological samples include blood, urine, saliva, tissue biopsy, and autopsy material.

Well-established hybridization methods of RNA detection include northern analysis and dot/slot blot hybridization (see, for example, Ausubel (1995) at pages 4-1 to 4-27, and Wu et al. (eds.), "Analysis of Gene Expression at the RNA Level," in *Methods in Gene Biotechnology*, pages 225–239 (CRC Press, Inc. 1997)). Nucleic acid probes can be detectably labeled with radioisotopes such as $^{32}P$ or $^{35}S$. Alternatively, interferon-ε RNA can be detected with a nonradioactive hybridization method (see, for example, Isaac (ed.), *Protocols for Nucleic Acid Analysis by Nonradioactive Probes* (Humana Press, Inc. 1993)). Typically, nonradioactive detection is achieved by enzymatic conversion of chromogenic or chemiluminescent substrates. Illustrative nonradioactive moieties include biotin, fluorescein, and digoxigenin.

Interferon-ε oligonucleotide probes are also useful for in vivo diagnosis. As an illustration, $^{18}F$-labeled oligonucleotides can be administered to a subject and visualized by positron emission tomography (Tavitian et al., *Nature Medicine* 4:467 (1998)).

Numerous diagnostic procedures take advantage of the polymerase chain reaction (PCR) to increase sensitivity of detection methods. Standard techniques for performing PCR are well-known (see, generally, Mathew (ed.), *Protocols in Human Molecular Genetics* (Humana Press, Inc. 1991), White (ed.), *PCR Protocols: Current Methods and Applications* (Humana Press, Inc. 1993), Cotter (ed.), *Molecular Diagnosis of Cancer* (Humana Press, Inc. 1996), Hanausek and Walaszek (eds.), *Tumor Marker Protocols* (Humana Press, Inc. 1998), Lo (ed.), *Clinical Applications of PCR* (Humana Press, Inc. 1998), and Meltzer (ed.), *PCR in Bioanalysis* (Humana Press, Inc. 1998)).

Preferably, PCR primers are designed to amplify a portion of the interferon-ε gene that has a low sequence similarity to a comparable region in other interferons. As an illustration, suitable primers are designed to amplify human interferon-ε regions within nucleotides 763 to 900, or nucleotides 970 to 1077 of SEQ ID NO:1.

One variation of PCR for diagnostic assays is reverse transcriptase-PCR (RT-PCR). In the RT-PCR technique, RNA is isolated from a biological sample, reverse transcribed to cDNA, and the cDNA is incubated with interferon-ε primers (see, for example, Wu et al. (eds.), "Rapid Isolation of Specific cDNAs or Genes by PCR," in *Methods in Gene Biotechnology*, pages 15–28 (CRC Press, Inc. 1997)). PCR is then performed and the products are analyzed using standard techniques.

As an illustration, RNA is isolated from biological sample using, for example, the gunadinium-thiocyanate cell lysis procedure described above. Alternatively, a solid-phase technique can be used to isolate mRNA from a cell lysate. A reverse transcription reaction can be primed with the isolated RNA using random oligonucleotides, short homopolymers of dT, or interferon-ε anti-sense oligomers. Oligo-dT primers offer the advantage that various mRNA nucleotide sequences are amplified that can provide control target sequences. Interferon-ε sequences are amplified by the polymerase chain reaction using two flanking oligonucleotide primers that are typically 20 bases in length.

PCR amplification products can be detected using a variety of approaches. For example, PCR products can be fractionated by gel electrophoresis, and visualized by ethidium bromide staining. Alternatively, fractionated PCR products can be transferred to a membrane, hybridized with a detectably-labeled interferon-ε probe, and examined by autoradiography. Additional alternative approaches include the use of digoxigenin-labeled deoxyribonucleic acid triphosphates to provide chemiluminescence detection, and the C-TRAK calorimetric assay.

Another approach for detection of interferon-ε expression is cycling probe technology (CPT), in which a single-stranded DNA target binds with an excess of DNA-RNA-DNA chimeric probe to form a complex, the RNA portion is cleaved with RNAase H, and the presence of cleaved chimeric probe is detected (see, for example, Beggs et al., *J. Clin. Microbiol.* 34:2985 (1996), Bekkaoui et al., *Biotechniques* 20:240 (1996)). Alternative methods for detection of interferon-ε sequences can utilize approaches such as nucleic acid sequence-based amplification (NASBA), cooperative amplification of templates by cross-hybridization (CATCH), and the ligase chain reaction (LCR) (see, for example, Marshall et al., U.S. Pat. No. 5,686,272 (1997), Dyer et al., *J. Virol. Methods* 60:161 (1996), Ehricht et al., *Eur. J. Biochem.* 243:358 (1997), and Chadwick et al., *J. Virol. Methods* 70:59 (1998)). Other standard methods are known to those of skill in the art.

Interferon-ε probes and primers can also be used to detect and to localize interferon-ε gene expression in tissue samples. Methods for such in situ hybridization are well-known to those of skill in the art (see, for example, Choo (ed.), *In Situ Hybridization Protocols* (Humana Press, Inc. 1994), Wu et al. (eds.), "Analysis of Cellular DNA or Abundance of mRNA by Radioactive In Situ Hybridization (RISH)," in *Methods in Gene Biotechnology*, pages 259–278 (CRC Press, Inc. 1997), and Wu et al. (eds.), "Localization of DNA or Abundance of mRNA by Fluorescence In Situ Hybridization (RISH)," in *Methods in Gene Biotechnology*, pages 279–289 (CRC Press, Inc. 1997)). Various additional diagnostic approaches are well-known to those of skill in the art (see, for example, Mathew (ed.), *Protocols in Human Molecular Genetics* (Humana Press, Inc. 1991), Coleman and Tsongalis, *Molecular Diagnostics* (Humana Press, Inc. 1996), and Elles, *Molecular Diagnosis of Genetic Diseases* (Humana Press, Inc., 1996)).

Nucleic acid molecules comprising interferon-ε nucleotide sequences can also be used to determine whether a subject's chromosomes contain a mutation in the interferon-ε gene. Detectable chromosomal aberrations at the interferon-ε gene locus include, but are not limited to, aneuploidy, gene copy number changes, insertions, deletions, restriction site changes and rearrangements. Of particular interest are genetic alterations that inactivate the interferon-ε gene.

Aberrations associated with the interferon-ε locus can be detected using nucleic acid molecules of the present invention by employing molecular genetic techniques, such as restriction fragment length polymorphism (RFLP) analysis, short tandem repeat (STR) analysis employing PCR techniques, amplification-refractory mutation system analysis (ARMS), single-strand conformation polymorphism (SSCP) detection, RNase cleavage methods, denaturing gradient gel electrophoresis, fluorescence-assisted mismatch analysis (FAMA), and other genetic analysis techniques known in the art (see, for example, Mathew (ed.), *Protocols in Human Molecular Genetics* (Humana Press, Inc. 1991), Marian, *Chest* 108:255 (1995), Coleman and Tsongalis, *Molecular Diagnostics* (Human Press, Inc. 1996), Elles (ed.) *Molecular Diagnosis of Genetic Diseases* (Humana Press, Inc. 1996), Landegren (ed.), *Laboratory Protocols for Mutation Detection* (Oxford University Press 1996), Birren et al. (eds.), *Genome Analysis, Vol. 2: Detecting Genes* (Cold Spring Harbor Laboratory Press 1998), Dracopoli et al. (eds.), *Current Protocols in Human Genetics* (John Wiley & Sons 1998), and Richards and Ward, "Molecular Diagnostic Testing," in *Principles of Molecular Medicine*, pages 83–88 (Humana Press, Inc. 1998)).

The protein truncation test is also useful for detecting the inactivation of a gene in which translation-terminating mutations produce only portions of the encoded protein (see, for example, Stoppa-Lyonnet et al., *Blood* 91:3920 (1998)). According to this approach, RNA is isolated from a biological sample, and used to synthesize cDNA. PCR is then used to amplify the interferon-ε target sequence and to introduce an RNA polymerase promoter, a translation initiation sequence, and an in-frame ATG triplet. PCR products are transcribed using an RNA polymerase, and the transcripts are translated in vitro with a T7-coupled reticulocyte lysate system. The translation products are then fractionated by SDS-PAGE to determine the lengths of the translation products. The protein truncation test is described, for example, by Dracopoli et al. (eds.), *Current Protocols in Human Genetics*, pages 9.11.1–9.11.18 (John Wiley & Sons 1998).

In a related approach, interferon-ε protein is isolated from a subject, the molecular weight of the isolated interferon-ε protein is determined, and then compared with the molecular weight a normal interferon-ε protein, such as a protein having the amino acid sequence of SEQ ID NO:2 or SEQ ID NO:24. A substantially lower molecular weight for the isolated interferon-ε protein is indicative that the protein is truncated. In this context, "substantially lower molecular weight" refers to at least about 10 percent lower, and preferably, at least about 25 percent lower. The interferon-ε protein may be isolated by various procedures known in the art including immunoprecipitation, solid phase radioimmunoassay, enzyme-linked immunosorbent assay, or Western blotting. The molecular weight of the isolated interferon-ε protein can be determined using standard techniques, such as SDS-polyacrylamide gel electrophoresis.

Analysis of chromosomal DNA using a human interferon-ε polynucleotide sequence is useful for correlating disease with abnormalities localized to chromosome 9, in particular to chromosome 9p22.2. In one embodiment, a method is used to detect a chromosome 9 abnormality in a sample from an individual comprising: (a) obtaining interferon-ε RNA from the sample, (b) generating interferon-ε cDNA by polymerase chain reaction, and (c) comparing the nucleotide sequence of the interferon-ε cDNA to the nucleic acid sequence as shown in SEQ ID NOs:1 or 4. In further embodiments, the difference between the sequence of the interferon-ε cDNA or interferon-ε gene in the sample and the interferon-ε sequence, as shown in SEQ ID NOs:1 or 4, is indicative of chromosome 9p22.2 abnormality.

The present invention also contemplates kits for performing a diagnostic assay for interferon-ε gene expression or to detect mutations in the interferon-ε gene. Such kits comprise nucleic acid probes, such as double-stranded nucleic acid molecules comprising the nucleotide sequence of SEQ ID NO:1, SEQ ID NO:4, SEQ ID NO:23, or a fragment thereof, as well as single-stranded nucleic acid molecules having the complement of the nucleotide sequence of SEQ ID NO:1, SEQ ID NO:4, SEQ ID NO:23, or a fragment thereof. Probe molecules may be DNA, RNA, oligonucleotides, and the like. Kits may comprise nucleic acid primers for performing PCR.

Preferably, such a kit contains all the necessary elements to perform a nucleic acid diagnostic assay described above. A kit will comprise at least one container comprising an interferon-ε probe or primer. The kit may also comprise a second container comprising one or more reagents capable of indicating the presence of interferon-ε sequences. Examples of such indicator reagents include detectable labels such as radioactive labels, fluorochromes, chemiluminescent agents, and the like. A kit may also comprise a means for conveying to the user that the interferon-ε probes and primers are used to detect interferon-ε gene expression. For example, written instructions may state that the enclosed nucleic acid molecules can be used to detect either a nucleic acid molecule that encodes interferon-ε, or a nucleic acid molecule having a nucleotide sequence that is complementary to an interferon-ε-encoding nucleotide sequence. The written material can be applied directly to a container, or the written material can be provided in the form of a packaging insert.

11. Diagnostic Application of Anti-interferon-ε Antibodies

The present invention contemplates the use of anti-interferon-ε antibodies to screen biological samples in vitro for the presence of interferon-ε. In one type of in vitro assay, anti-interferon-ε antibodies are used in liquid phase. For example, the presence of interferon-ε in a biological sample can be tested by mixing the biological sample with a trace amount of labeled interferon-ε and an anti-interferon-ε antibody under conditions that promote binding between interferon-ε and its antibody. Complexes of interferon-ε and anti-interferon-ε in the sample can be separated from the reaction mixture by contacting the complex with an immobilized protein which binds with the antibody, such as an Fc antibody or Staphylococcus protein A. The concentration of interferon-ε in the biological sample will be inversely proportional to the amount of labeled interferon-ε bound to the antibody and directly related to the amount of free labeled interferon-ε. Illustrative biological samples include blood, urine, saliva, tissue biopsy, and autopsy material.

Alternatively, in vitro assays can be performed in which anti-interferon-ε antibody is bound to a solid-phase carrier. For example, antibody can be attached to a polymer, such as aminodextran, in order to link the antibody to an insoluble support such as a polymer-coated bead, a plate or a tube. Other suitable in vitro assays will be readily apparent to those of skill in the art.

In another approach, anti-interferon-ε antibodies can be used to detect interferon-ε in tissue sections prepared from a biopsy specimen. Such immunochemical detection can be used to determine the relative abundance of interferon-ε and to determine the distribution of interferon-ε in the examined tissue. General inmmunochemistry techniques are well established (see, for example, Ponder, "Cell Marking Techniques and Their Application," in *Mammalian Development: A Practical Approach,* Monk (ed.), pages 115–38 (IRL Press 1987), Coligan at pages 5.8.1–5.8.8, Ausubel (1995) at pages 14.6.1 to 14.6.13 (Wiley Interscience 1990), and Manson (ed.), *Methods In Molecular Biology, Vol.* 10: *Immunochemical Protocols* (The Humana Press, Inc. 1992)).

Immunochemical detection can be performed by contacting a biological sample with an anti-interferon-ε antibody, and then contacting the biological sample with a detectably labeled molecule which binds to the antibody. For example, the detectably labeled molecule can comprise an antibody moiety that binds to anti-interferon-ε antibody. Alternatively, the anti-interferon-ε antibody can be conjugated with avidin/streptavidin (or biotin) and the detectably labeled molecule can comprise biotin (or avidin/streptavidin). Numerous variations of this basic technique are well-known to those of skill in the art.

Alternatively, an anti-interferon-ε antibody can be conjugated with a detectable label to form an anti-interferon-ε immunoconjugate. Suitable detectable labels include, for example, a radioisotope, a fluorescent label, a chemiluminescent label, an enzyme label, a bioluminescent label or colloidal gold. Methods of making and detecting such detectably-labeled immunoconjugates are well-known to those of ordinary skill in the art, and are described in more detail below.

The detectable label can be a radioisotope that is detected by autoradiography. Isotopes that are particularly useful for the purpose of the present invention are $^3$H, $^{125}$I, $^{113}$I, $^{35}$S and $^{14}$C.

Anti-interferon-ε immunoconjugates can also be labeled with a fluorescent compound. The presence of a fluorescently-labeled antibody is determined by exposing the immunoconjugate to light of the proper wavelength and detecting the resultant fluorescence. Fluorescent labeling compounds include fluorescein isothiocyanate, rhodamine, phycoerytherin, phycocyanin, allophycocyanin, o-phthaldehyde and fluorescamine.

Alternatively, anti-interferon-ε immunoconjugates can be detectably labeled by coupling an antibody component to a chemiluminescent compound. The presence of the chemiluminescent-tagged immunoconjugate is determined by detecting the presence of luminescence that arises during the course of a chemical reaction. Examples of chemiluminescent labeling compounds include luminol, isoluminol, an aromatic acridinium ester, an imidazole, an acridinium salt and an oxalate ester.

Similarly, a bioluminescent compound can be used to label anti-interferon-ε immunoconjugates of the present invention. Biolumninescence is a type of chemiluminescence found in biological systems in which a catalytic protein increases the efficiency of the chemiluminescent reaction. The presence of a bioluminescent protein is determined by detecting the presence of luminescence. Bioluminescent compounds that are useful for labeling include luciferin, luciferase and aequorin.

Alternatively, anti-interferon-ε immunoconjugates can be detectably labeled by linking an anti-interferon-ε antibody component to an enzyme. When the anti-interferon-ε-enzyme conjugate is incubated in the presence of the appropriate substrate, the enzyme moiety reacts with the substrate to produce a chemical moiety which can be detected, for example, by spectrophotometric, fluorometric or visual means. Examples of enzymes that can be used to detectably label polyspecific immunoconjugates include β-galactosidase, glucose oxidase, peroxidase and alkaline phosphatase.

Those of skill in the art will know of other suitable labels which can be employed in accordance with the present invention. The binding of marker moieties to anti-interferon-ε antibodies can be accomplished using standard techniques known to the art. Typical methodology in this regard is described by Kennedy et al., *Clin. Chim. Acta* 70:1 (1976), Schurs et al., *Clin. Chim. Acta* 81:1 (1977), Shih et al., *Int'l J. Cancer* 46:1101 (1990), Stein et al, *Cancer Res.* 50:1330 (1990), and Coligan, supra.

Moreover, the convenience and versatility of immunochemical detection can be enhanced by using anti-interferon-ε antibodies that have been conjugated with avidin, streptavidin, and biotin (see, for example, Wilchek et al. (eds.), "Avidin-Biotin Technology," *Methods In Enzymology, Vol.* 184 (Academic Press 1990), and Bayer et al., "Inmmunochemical Applications of Avidin-Biotin Technology," in *Methods In Molecular Biology, Vol.* 10, Manson (ed.), pages 149–162 (The Humana Press, Inc. 1992).

Methods for performing immunoassays are well-established. See, for example, Cook and Self, "Monoclonal Antibodies in Diagnostic Immunoassays," in *Monoclonal Antibodies: Production, Engineering, and Clinical Application,* Ritter and Ladyman (eds.), pages 180–208, (Cambridge University Press, 1995), Perry, "The Role of Monoclonal Antibodies in the Advancement of Immunoassay Technology," in *Monoclonal Antibodies: Principles and Applications,* Birch and Lennox (eds.), pages 107–120 (Wiley-Liss, Inc. 1995), and Diamandis, *Immunoassay* (Academic Press, Inc. 1996).

In a related approach, biotin- or FITC-labeled interferon-ε can be used to identify cells that bind interferon-ε. Such can binding can be detected, for example, using flow cytometry.

The present invention also contemplates kits for performing an immunological diagnostic assay for interferon-ε gene expression. Such kits comprise at least one container comprising ail anti-interferon-ε antibody, or antibody fragment. A kit may also comprise a second container comprising one or more reagents capable of indicating the presence of interferon-ε antibody or antibody fragments. Examples of such indicator reagents include detectable labels such as a radioactive label, a fluorescent label, a chemiluminescent label, an enzyme label, a bioluminescent label, colloidal gold, and the like. A kit may also comprise a means for conveying to the user that interferon-ε antibodies or antibody fragments are used to detect interferon-ε protein. For example, written instructions may state that the enclosed antibody or antibody fragment can be used to detect interferon-ε. The written material can be applied directly to a container, or the written material can be provided in the form of a packaging insert.

12. Therapeutic Uses of Polypeptides Having Interferon-ε Activity

Interferons are known to be potent cytokines that possess antiviral, immunomodulating, and anti-proliferative activities. Therefore, the present invention includes the use of proteins, polypeptides, and peptides having interferon-ε activity (such as interferon-ε polypeptides, interferon-ε analogs, and interferon-ε fusion proteins) to provide antiviral, immunomodulatory, or anti-proliferative activity.

Both recombinant interferons and interferons isolated from natural sources have been approved in the United States for treatment of autoimmune diseases, condyloma acuminatum, chronic hepatitis C, bladder carcinoma, cervical carcinoma, laryngeal papillomatosis, fungoides mycosis, chronic hepatitis B, Kaposi's sarcoma in patients infected with human immunodeficiency virus, malignant melanoma, hairy cell leukemia, and multiple sclerosis. In addition, interferon-ε may be used to treat forms of arteriosclerosis, such as atherosclerosis, by inhibiting cell proliferation. Accordingly, the present invention contemplates the use of proteins, polypeptides, and peptides having interferon-ε activity to treat such conditions.

As an illustration, Example 7 shows that murine interferon-ε can inhibit the proliferation of the human Burkitt lymphoma B cell line Daudi. Both in vitro and in vivo studies with Daudi cells have been performed to test therapies for lymphomas, acute leukemia, and human B-lineage malignancies (see, for example, Tressler et al.,*Int. J Cancer* 57:568 (1994); Konikova et al., *Neoplasma* 42:227 (1995); Gidlof et al., *Blood* 89:2089 (1997); Yanase et al., *J. Interferon Cytokine Res.* 18:855 (1998). Accordingly, interferon-ε, such as murine interferon-ε, can be used to treat lymphoproliferative disorders, including B-cell lymphomas, chronic lymphatic leukemias, and acute lymphatic leukemias.

Interferons are also known to augment the presentation of human tumor antigens, as discussed above. Thus, the present invention includes the use of proteins, polypeptides and peptides having interferon-ε activity as an adjuvant for immunotherapy or immunoscintigraphy using anti-tumor antigen antibodies.

Members of the type I interferon family have also been shown to influence neural cell activity and growth (see, for example, Dafny et al., *Brain Res.* 734:269 (1996); Pliopsys and Massimini, *Neuroimmunomodulation* 2:31 (1995)). In addition, intraventricular injection of neural growth factors has been shown to influence learning in animal models (see, for example, Fischer, et al., *Nature* 329:65 (1987)). Accordingly, the present invention includes methods for using interferon-ε protein to treat disorders of the central nervous system, including anxiety, depression, schizophrenia, Parkinson's disease, stroke, amyotrophic lateral sclerosis, multiple sclerosis, Alzheimer's disease, and Huntington's disease. Either human or murine interferon-ε protein can be used for such methods.

Human or murine interferon-ε can also be used to treat myocarditis, a disorder that arises when the heart is involved in an inflammatory process. The infiltration of lymphocytes and myocytolysis is thought to result after infection by virus, bacteria, fungi or parasites (see, for example, Brodison et al., *J. Infection* 37:99 (1998)). Human or murine interferon-ε can be injected intravenously to treat infections associated with myocarditis. Human or murine interferon-ε can also be administered intravenously as an immunoregulatory cytokine in the treatment of autoimmune myocarditis. Interferon dosages can be extrapolated using a autoimmune model of myocarditis in the A/J mouse (Donermeyer, et al., *J. Exp. Med.* 182:1291 (1995)).

Exogenous administration of interferon-τ in sheep increases the pregnancy rate (Aggarwal, *Human Cytokines III,* (Blackwell Science 1997)). As described herein, interferon-ε mRNA is expressed in placenta. Accordingly, the present invention includes the use of interferon-ε, such as the disclosed human or murine interferon-ε, to promote and protect growth of the fetus. As an illustration, interferon-ε can be used to protect a developing fetus from viral infection (e.g., human immunodeficiency virus, human papilloma virus, and the like). In addition, human or murine interferon-ε can be used to promote in vitro fertilization.

Generally, the dosage of administered interferon-ε (or interferon-ε analog or fusion protein) will vary depending upon such factors as the patient's age, weight, height, sex, general medical condition and previous medical history. Typically, it is desirable to provide the recipient with a dosage of interferon-ε which is in the range of from about 1 pg/kg to 10 mg/kg (amount of agent/body weight of patient), although a lower or higher dose also may be administered as circumstances dictate.

Administration of a molecule having interferon-ε activity to a subject can be intravenous, intraarterial, intraperitoneal, intramuscular, subcutaneous, intrapleural, intrathecal, by perfusion through a regional catheter, or by direct intralesional injection. When administering therapeutic proteins by injection, the administration may be by continuous infusion or by single or multiple boluses. Alternatively, interferon-ε can be administered as a controlled release formulation. For example, Cleland and Jones, *Pharm. Res.* 13:1464 (1996), describe a method for producing interferon-γ encapsulated in polylactic-coglycolic microspheres.

Additional routes of administration include oral, dermal, mucosal-membrane, pulmonary, and transcutaneous. Oral delivery is suitable for polyester microspheres, zein microspheres, proteinoid microspheres, polycyanoacrylate microspheres, and lipid-based systems (see, for example, DiBase and Morrel, "Oral Delivery of Microencapsulated Proteins," in *Protein Delivery: Physical Systems,* Sanders and Hendren (eds.), pages 255–288 (Plenum Press 1997)). The feasibility of an intranasal delivery is exemplified by such a mode of insulin administration (see, for example, Hinchcliffe and Illum, *Adv. Drug Deliv. Rev.* 35:199 (1999)). Dry or liquid particles comprising interferon-ε can be prepared and inhaled with the aid of dry-powder dispersers, liquid aerosol generators, or nebulizers (e.g., Pettit and Gombotz, *TIBTECH* 16:343 (1998); Patton et al., *Adv. Drug Deliv. Rev.* 35:235 (1999)). This approach is illustrated by the AERX diabetes management system, which is a hand-held electronic inhaler that delivers aerosolized insulin into the lungs. Studies have shown that proteins as large as 48,000 kDa have been delivered across skin at therapeutic concentrations with the aid of low-frequency ultrasound, which illustrates the feasibility of trascutaneous administration (Mitragotri et al., *Science* 269:850 (1995)). Transdermal delivery using electroporation provides another means to administer interferon-ε (Potts et al., *Pharm. Biotechnol.* 10:213 (1997)).

A pharmaceutical composition comprising a protein, polypeptide, or peptide having interferon-ε activity can be formulated according to known methods to prepare pharmaceutically useful compositions, whereby the therapeutic proteins are combined in a mixture with a pharmaceutically acceptable carrier. A composition is said to be a "pharmaceutically acceptable carrier" if its administration can be tolerated by a recipient patient. Sterile phosphate-buffered saline is one example of a pharmaceutically acceptable carrier. Other suitable carriers are well-known to those in the art. See, for example, Gennaro (ed.), *Remington's Pharmaceutical Sciences,* 19th Edition (Mack Publishing Company 1995).

For purposes of therapy, molecules having interferon-ε activity and a pharmaceutically acceptable carrier are administered to a patient in a therapeutically effective amount. A combination of a protein, polypeptide, or peptide having interferon-ε activity and a pharmaceutically acceptable carrier is said to be administered in a "therapeutically effective amount" if the amount administered is physiologically significant. An agent is physiologically significant if its presence results in a detectable change in the physiology of a recipient patient. In the present context, an agent is physiologically significant if its presence results in the inhibition of the growth of tumor cells or in the inhibition of a viral infection. An inhibition of tumor growth may be indicated, for example, by a decrease in the number of tumor cells, decreased metastasis, a decrease in the size of a solid tumor, or increased necrosis of a tumor. Indicators of viral infection inhibition include decreased viral titer, a decrease in detectable viral antigen, or an increase in anti-viral antibody titer.

A pharmaceutical composition comprising molecules having interferon-ε activity can be furnished in liquid form, in an aerosol, or in solid form. Proteins having interferon-ε activity, such as human or murine interferon-ε, can be administered as a conjugate with a pharmaceutically acceptable water-soluble polymer moiety, as described above. As an illustration, an interferon-ε-polyethylene glycol conjugate is useful to increase the circulating half-life of the interferon, and to reduce the immunogenicity of the polypeptide. Liquid forms, including liposome-encapsulated formulations, are illustrated by injectable solutions and oral suspensions. Exemplary solid forms include capsules, tablets, and controlled-release forms, such as a miniosmotic pump or an implant. Other dosage forms can be devised by those skilled in the art, as shown, for example, by Ansel and Popovich, *Pharmaceutical Dosage Forms and Drug Delivery Systems,* 5$^{th}$ Edition (Lea & Febiger 1990), Gennaro (ed.), *Remington's Pharmaceutical Sciences,* 19$^{th}$ Edition (Mack Publishing Company 1995), and by Ranade and Hollinger, *Drug Delivery Systems* (CRC Press 1996).

As an illustration, interferon-ε pharmaceutical compositions may be supplied as a kit comprising a container that comprises interferon-ε, an interferon-ε agonist, or an interferon-ε antagonist (e.g., an anti-interferon-ε antibody or antibody fragment). Interferon-ε can be provided in the form of an injectable solution for single or multiple doses, or as a sterile powder that will be reconstituted before injection. Alternatively, such a kit can include a drypowder disperser, liquid aerosol generator, or nebulizer for administration of a therapeutic polypeptide. Such a kit may further comprise written information on indications and usage of the pharmaceutical composition. Moreover, such information may include a statement that the interferon-ε composition is contraindicated in patients with known hypersensitivity to interferon-ε.

13. Therapeutic Uses of Interferon-ε Nucleotide Sequences

Immunomodulator genes can be introduced into a subject to enhance immunological responses. As an illustration "immunomodulator gene therapy" has been examined in model systems using vectors that express IL-2, IL-3, IL-4, IL-6, IL-10, IL-12, IL-15, interferon-γ, tumor necrosis factor-α, or granulocyte-macrophage colony-stimulating factor (see, for example, Cao et al., *J. Gastroenterol. Hepatol.* 11:1053 (1996), Tahara et al., *Ann. N.Y. Acad. Sci.* 795:275 (1996), Rakhmilevich et al., *Hum. Gene Ther.* 8:1303 (1997), and Cao et al., *Transplantation* 65:325 (1998)). The present invention includes the use of interferon-ε nucleotide sequences to augment an immunological response to a tumor or viral infection in a subject. In addition, a therapeutic expression vector can be provided that inhibits interferon-ε gene expression, such as an antisense molecule, a ribozyme, or an external guide sequence molecule. Although murine interferon-ε nucleotide sequences can be used for these methods, compositions comprising human interferon-ε nucleotide sequences are preferred for treatment of human subjects.

There are numerous approaches to introduce an interferon-ε gene to a subject, including the use of recombinant host cells that express interferon-ε, delivery of naked nucleic acid encoding interferon-ε, use of a cationic lipid carrier with a nucleic acid molecule that encodes interferon-ε, and the use of viruses that express interferon-ε, such as recombinant retroviruses, recombinant adeno-associated viruses, recombinant adenoviruses, and recombinant Herpes simplex viruses [HSV] (see, for example, Mulligan, *Science* 260:926 (1993), Rosenberg et al., *Science* 242:1575 (1988), LaSalle et al., *Science* 259:988 (1993), Wolff et al., *Science* 247:1465 (1990), Breakfield and Deluca, *The New Biologist* 3:203 (1991)). In an ex vivo approach, for example, cells are isolated from a subject, transfected with a vector that expresses an interferon-ε gene, and then transplanted into the subject.

In order to effect expression of an interferon-ε gene, an expression vector is constructed in which a nucleotide sequence encoding an interferon-ε gene is operably linked to a core promoter, and optionally a regulatory element, to control gene transcription. The general requirements of an expression vector are described above.

Alternatively, an interferon-ε gene can be delivered using recombinant viral vectors, including for example, adenoviral vectors (e.g., Kass-Eisler et al., *Proc. Nat'l Acad. Sci. USA* 90:11498 (1993), Kolls et al., *Proc. Nat'l Acad. Sci. USA* 91:215 (1994), Li et al., *Hum. Gene Ther.* 4:403 (1993), Vincent et al., *Nat. Genet.* 5:130 (1993), and Zabner et al., *Cell* 75:207 (1993)), adenovirus-associated viral vectors (Flotte et al., *Proc. Nat'l Acad. Sci. USA* 90:10613 (1993)), alphaviruses such as Semliki Forest Virus and Sindbis Virus (Hertz and Huang, *J. Vir.* 66:857 (1992), Raju and Huang, *J. Vir.* 65:2501 (1991), and Xiong et al., *Science* 243:1188 (1989)), herpes viral vectors (e.g., U.S. Pat. Nos. 4,769,331, 4,859,587, 5,288,641 and 5,328,688), parvovirus vectors (Koering et al., *Hum. Gene Therap.* 5:457 (1994)), pox virus vectors (Ozaki et al., *Biochem. Biophys. Res. Comm.* 193:653 (1993), Panicali and Paoletti, *Proc. Nat'l Acad. Sci. USA* 79:4927 (1982)), pox viruses, such as canary pox virus or vaccinia virus (Fisher-Hoch et al., *Proc. Nat'l Acad. Sci. USA* 86:317 (1989), and Flexner et al., *Ann. N.Y. Acad. Sci.* 569:86 (1989)), and retroviruses (e.g, Baba et al., *J. Neurosurg* 79:729 (1993), Ram et al., *Cancer Res.* 53:83 (1993), Takamiya et al., *J. Neurosci. Res* 33:493 (1992), Vile and Hart, *Cancer Res.* 53:962 (1993), Vile and Hart, *Cancer Res.* 53:3860 (1993), and Anderson et al., U.S. Pat. No. 5,399,346). Within various embodiments, either the viral vector itself, or a viral particle which contains the viral vector may be utilized in the methods and compositions described below.

As an illustration of one system, adenovirus, a double-stranded DNA virus, is a well-characterized gene transfer vector for delivery of a heterologous nucleic acid molecule (for a review, see Becker et al., *Meth. Cell Biol.* 43:161 (1994); Douglas and Curiel, *Science & Medicine* 4:44 (1997)). The adenovirus system offers several advantages including: (i) the ability to accommodate relatively large DNA inserts, (ii) the ability to be grown to high-titer, (iii) the ability to infect a broad range of mammalian cell types, and (iv) the ability to be used with many different promoters including ubiquitous, tissue specific, and regulatable promoters. In addition, adenoviruses can be administered by intravenous injection, because the viruses are stable in the bloodstream.

Using adenovirus vectors where portions of the adenovirus genome are deleted, inserts are incorporated into the viral DNA by direct ligation or by homologous recombination with a co-transfected plasmid. In an exemplary system, the essential E1 gene is deleted from the viral vector, and the virus will not replicate unless the E1 gene is provided by the host cell. When intravenously administered to intact animals, adenovirus primarily targets the liver. Although an adenoviral delivery system with an E1 gene deletion cannot replicate in the host cells, the host's tissue will express and process an encoded heterologous protein. Host cells will also secrete the heterologous protein if the corresponding gene includes a secretory signal sequence. Secreted proteins will enter the circulation from tissue that expresses the heterologous gene (e.g., the highly vascularized liver).

Moreover, adenoviral vectors containing various deletions of viral genes can be used to reduce or eliminate immune responses to the vector. Such adenoviruses are E1l-deleted, and in addition, contain deletions of E2A or E4 (Lusky et al., *J. Virol.* 72:2022 (1998); Raper et al., *Human Gene Therapy* 9:671 (1998)). The deletion of E2b has also been reported to reduce immune responses (Amalfitano et al., *J. Virol.* 72:926 (1998)). By deleting the entire adenovirus genome, very large inserts of heterologous DNA can be accommodated. Generation of so called "gutless" adenoviruses, where all viral genes are deleted, are particularly advantageous for insertion of large inserts of heterologous DNA (for a review, see Yeh. and Perricaudet, *FASEB J.* 11:615 (1997)).

High titer stocks of recombinant viruses capable of expressing a therapeutic gene can be obtained from infected mammalian cells using standard methods. For example, recombinant HSV can be prepared in Vero cells, as described by Brandt et al., *J. Gen. Virol.* 72:2043 (1991), Herold et al., *J. Gen. Virol.* 75:1211 (1994), Visalli and Brandt, *Virology* 185:419 (1991), Grau et al., *Invest. Ophthalmol. Vis. Sci.* 30:2474 (1989), Brandt et al., *J. Virol. Meth.* 36:209 (1992), and by Brown and MacLean (eds.), HSV Virus Protocols (Humana Press 1997).

Alternatively, an expression vector comprising an interferon-ε gene can be introduced into a subject's cells by lipofection in vivo using liposomes. Synthetic cationic lipids can be used to prepare liposomes for in vivo transfection of a gene encoding a marker (Felgner et al., *Proc. Nat'l Acad. Sci. USA* 84:7413 (1987); Mackey et al., *Proc. Nat'l Acad. Sci. USA* 85:8027 (1988)). The use of lipofection to introduce exogenous genes into specific organs in vivo has certain practical advantages. Liposomes can be used to direct transfection to particular cell types, which is particularly advantageous in a tissue with cellular heterogeneity, such as the pancreas, liver, kidney, and brain. Lipids may be chemically coupled to other molecules for the purpose of targeting. Targeted peptides (e.g., hormones or neurotransmitters), proteins such as antibodies, or non-peptide molecules can be coupled to liposomes chemically.

Electroporation is another alternative mode of administration. For example, Aihara and Miyazaki, *Nature Biotechnology* 16:867 (1998), have demonstrated the use of in vivo electroporation for gene transfer into muscle.

In an alternative approach to gene therapy, a therapeutic gene may encode an interferon-ε anti-sense RNA that inhibits the expression of interferon-ε. Suitable sequences for anti-sense molecules can be derived from the nucleotide sequences of interferon-ε disclosed herein.

Alternatively, an expression vector can be constructed in which a regulatory element is operably linked to a nucleotide sequence that encodes a ribozyme. Ribozymes can be designed to express endonuclease activity that is directed to a certain target sequence in a mRNA molecule (see, for example, Draper and Macejak, U.S. Pat. No. 5,496,698, McSwiggen, U.S. Pat. No. 5,525,468, Chowrira and McSwiggen, U.S. Pat. No. 5,631,359, and Robertson and Goldberg, U.S. Pat. No. 5,225,337). In the context of the present invention, ribozymes include nucleotide sequences that bind with interferon-$\epsilon$ mRNA.

In another approach, expression vectors can be constructed in which a regulatory element directs the production of RNA transcripts capable of promoting RNase P-mediated cleavage of mRNA molecules that encode an interferon-$\epsilon$ gene. According to this approach, an external guide sequence can be constructed for directing the endogenous ribozyme, RNase P, to a particular species of intracellular mRNA, which is subsequently cleaved by the cellular ribozyme (see, for example, Altman et al., U.S. Pat. No. 5,168,053, Yuan et al., *Science* 263:1269 (1994), Pace et al., international publication No. WO 96/18733, George et al., international publication No. WO 96/21731, and Werner et al., international publication No. WO 97/33991). Preferably, the external guide sequence comprises a ten to fifteen nucleotide sequence complementary to interferon-ϵ mRNA, and a 3'-NCCA nucleotide sequence, wherein N is preferably a purine. The external guide sequence transcripts bind to the targeted MRNA species by the formation of base pairs between the mRNA and the complementary external guide sequences, thus promoting cleavage of mRNA by RNase P at the nucleotide located at the 5'-side of the base-paired region.

In general, the dosage of a composition comprising a therapeutic vector having an interferon-ϵ nucleotide acid sequence, such as a recombinant virus, will vary depending upon such factors as the subject's age, weight, height, sex, general medical condition and previous medical history. Suitable routes of administration of therapeutic vectors include intravenous injection, intraarterial injection, intraperitoneal injection, intramuscular injection, intratumoral injection, and injection into a cavity that contains a tumor. As an illustration, Horton et al., *Proc. Nat'l Acad. Sci. USA* 96:1553 (1999), demonstrated that intramuscular injection of plasmid DNA encoding interferon-α produces potent antitumor effects on primary and metastatic tumors in a murine model.

A composition comprising viral vectors, non-viral vectors, or a combination of viral and non-viral vectors of the present invention can be formulated according to known methods to prepare pharmaceutically useful compositions, whereby vectors or viruses are combined in a mixture with a pharmaceutically acceptable carrier. As noted above, a composition, such as phosphate-buffered saline is said to be a "pharmaceutically acceptable carrier" if its administration can be tolerated by a recipient subject. Other suitable carriers are well-known to those in the art (see, for example, *Remington's Pharmaceutical Sciences,* 19th Ed. (Mack Publishing Co. 1995), and *Gilman's the Pharmacological Basis of Therapeutics,* 7th Ed. (MacMillan Publishing Co. 1985)).

For purposes of therapy, a therapeutic gene expression vector, or a recombinant virus comprising such a vector, and a pharmaceutically acceptable carrier are administered to a subject in a therapeutically effective amount. A combination of an expression vector (or virus) and a pharmaceutically acceptable carrier is said to be administered in a "therapeutically effective amount" if the amount administered is physiologically significant. An agent is physiologically significant if its presence results in a detectable change in the physiology of a recipient subject. In the present context, an agent is physiologically significant if its presence inhibits the growth of tumor cells or inhibits viral infection. An inhibition of tumor growth may be indicated, for example, by a decrease in the number of tumor cells, decreased metastasis, a decrease in the size of a solid tumor, or increased necrosis of a tumor. Indicators of viral infection inhibition include decreased viral titer, a decrease in detectable viral antigen, or an increase in anti-viral antibody titer.

When the subject treated with a therapeutic gene expression vector or a recombinant virus is a human, then the therapy is preferably somatic cell gene therapy. That is, the preferred treatment of a human with a therapeutic gene expression vector or a recombinant virus does not entail introducing into cells a nucleic acid molecule that can form part of a human germ line and be passed onto successive generations (i.e., human germ line gene therapy).

14. Production of Transgenic Mice

Transgenic mice can be engineered to over-express the human or murine interferon-ϵ gene in all tissues or under the control of a tissue-specific or tissue-preferred regulatory element. These over-producers of interferon-ϵ can be used to characterize the phenotype that results from over-expression, and the transgenic animals can serve as models for human disease caused by excess interferon-ϵ. Transgenic mice that over-express interferon-ϵ also provide model bioreactors for production of interferon-ϵ in the milk or blood of larger animals. Methods for producing transgenic mice are well-known to those of skill in the art (see, for example, Jacob, "Expression and Knockout of Interferons in Transgenic Mice," in *Overexpression and Knockout of Cytokines in Transgenic Mice,* Jacob (ed.), pages 111–124 (Academic Press, Ltd. 1994), Monastersky and Robl (eds.), *Strategies in Transgenic Animal Science* (ASM Press 1995), and Abbud and Nilson, "Recombinant Protein Expression in Transgenic Mice," in *Gene Expression Systems: Using Nature for the Art of Expression,* Fernandez and Hoeffier (eds.), pages 367–397 (Academic Press, Inc. 1999)).

For example, a method for producing a transgenic mouse that expresses an interferon-ϵ gene can begin with adult, fertile males (studs) (B6C3fl, 2–8 months of age (Taconic Farms, Germantown, N.Y.)), vasectomized males (duds) (B6D2fl, 2–8 months, (Taconic Farms)), prepubescent fertile females (donors) (B6C3fl, 4–5 weeks, (Taconic Farms)) and adult fertile females (recipients) (B6D2fl, 2–4 months, (Taconic Farms)). The donors are acclimated for one week and then injected with approximately 8 IU/mouse of Pregnant Mare's Serum gonadotrophin (Sigma Chemical Company; St. Louis, Mo.) I.P., and 46–47 hours later, 8 IU/mouse of human Chorionic Gonadotropin (hCG (Sigma)) I.P. to induce superovulation. Donors are mated with studs subsequent to hormone injections. Ovulation generally occurs within 13 hours of hCG injection. Copulation is confirmed by the presence of a vaginal plug the morning following mating.

Fertilized eggs are collected under a surgical scope. The oviducts are collected and eggs are released into urinanalysis slides containing hyaluronidase (Sigma). Eggs are washed once in hyaluronidase, and twice in Whitten's W640 medium (described, for example, by Menino and O'Clary, *Biol. Reprod.* 77:159 (1986), and Dienhart and Downs, *Zygote* 4:129 (1996)) that has been incubated with 5% $CO_2$, 5% $O_2$, and 90% $N_2$ at 37° C. The eggs are then stored in a 37° C./5% $CO_2$ incubator until microinjection.

Ten to twenty micrograms of plasmid DNA containing an interferon-ϵ encoding sequence is linearized, gel-purified, and resuspended in 10 mM Tris-HCl (pH 7.4), 0.25 mM EDTA (pH 8.0), at a final concentration of 5–10 nanograms per microliter for microinjection. For example, the interferon-ε encoding sequences can encode amino acid residues 22 to 208 of either SEQ ID NO:2 or 5, or amino acid residues 22 to 192 of SEQ ID NO:24.

Plasmid DNA is microinjected into harvested eggs contained in a drop of W640 medium overlaid by warm, $CO_2$-equilibrated mineral oil. The DNA is drawn into an injection needle (pulled from a 0.75 mm ID, 1 mm OD borosilicate glass capillary), and injected into individual eggs. Each egg is penetrated with the injection needle, into one or both of the haploid pronuclei.

Picoliters of DNA are injected into the pronuclei, and the injection needle withdrawn without coming into contact with the nucleoli. The procedure is repeated until all the eggs are injected. Successfully microinjected eggs are transferred into an organ tissue-culture dish with pre-gassed W640 medium for storage overnight in a 37° C./5% $CO_2$ incubator.

The following day, two-cell embryos are transferred into pseudopregnant recipients. The recipients are identified by the presence of copulation plugs, after copulating with vasectomized duds. Recipients are anesthetized and shaved on the dorsal left side and transferred to a surgical microscope. A small incision is made in the skin and through the muscle wall in the middle of the abdominal area outlined by the ribcage, the saddle, and the hind leg, midway between knee and spleen. The reproductive organs are exteriorized onto a small surgical drape. The fat pad is stretched out over the surgical drape, and a baby serrefine (Roboz, Rockville, Md.) is attached to the fat pad and left hanging over the back of the mouse, preventing the organs from sliding back in.

With a fine transfer pipette containing mineral oil followed by alternating W640 and air bubbles, 12–17 healthy two-cell embryos from the previous day's injection are transferred into the recipient. The swollen ampulla is located and holding the oviduct between the ampulla and the bursa, a nick in the oviduct is made with a 28 g needle close to the bursa, making sure not to tear the ampulla or the bursa.

The pipette is transferred into the nick in the oviduct, and the embryos are blown in, allowing the first air bubble to escape the pipette. The fat pad is gently pushed into the peritoneum, and the reproductive organs allowed to slide in. The peritoneal wall is closed with one suture and the skin closed with a wound clip. The mice recuperate on a 37° C. slide warmer for a minimum of four hours.

The recipients are returned to cages in pairs, and allowed 19–21 days gestation. After birth, 19–21 days postpartum is allowed before weaning. The weanlings are sexed and placed into separate sex cages, and a 0.5 cm biopsy (used for genotyping) is snipped off the tail with clean scissors.

Genomic DNA is prepared from the tail snips using, for example, a QIAGEN DNEASY kit following the manufacturer's instructions. Genomic DNA is analyzed by PCR using primers designed to amplify an interferon-ε gene or a selectable marker gene that was introduced in the same plasmid. Illustrative primers suitable for amplifying human interferon-ε are described in the Examples, below. After animals are confirmed to be transgenic, they are backcrossed into an inbred strain by placing a transgenic female with a wild-type male, or a transgenic male with one or two wild-type female(s). As pups are born and weaned, the sexes are separated, and their tails snipped for genotyping.

To check for expression of a transgene in a live animal, a partial hepatectomy is performed. A surgical prep is made of the upper abdomen directly below the zyphoid process. Using sterile technique, a small 1.5–2 cm incision is made below the sternum and the left lateral lobe of the liver exteriorized. Using 4-0 silk, a tie is made around the lower lobe securing it outside the body cavity. An atraumatic clamp is used to hold the tie while a second loop of absorbable Dexon (American Cyanamid; Wayne, N.J.) is placed proximal to the first tie. A distal cut is made from the Dexon tie and approximately 100 mg of the excised liver tissue is placed in a sterile petri dish. The excised liver section is transferred to a 14 ml polypropylene round bottom tube and snap frozen in liquid nitrogen and then stored on dry ice. The surgical site is closed with suture and wound clips, and the animal's cage placed on a 37° C. heating pad for 24 hours post operatively. The animal is checked daily post operatively and the wound clips removed 7–10 days after surgery. The expression level of interferon-ε mRNA is examined for each transgenic mouse using an RNA solution hybridization assay or polymerase chain reaction.

In addition to producing transgenic mice that over-express interferon-ε, it is useful to engineer transgenic mice with either abnormally low or no expression of the gene. Such transgenic mice provide useful models for diseases associated with a lack of interferon-ε. As discussed above, interferon-ε gene expression can be inhibited using antisense genes, ribozyme genes, or external guide sequence genes. To produce transgenic mice that under-express the interferon-ε gene, such inhibitory sequences are targeted to murine interferon-ε mRNA. Methods for producing transgenic mice that have abnormally low expression of a particular gene are known to those in the art (see, for example, Wu et al., "Gene Underexpression in Cultured Cells and Animals by Antisense DNA and RNA Strategies," in *Methods in Gene Biotechnology*, pages 205–224 (CRC Press 1997)).

An alternative approach to producing transgenic mice that have little or no interferon-ε gene expression is to generate mice having at least one normal interferon-ε allele replaced by a nonfunctional interferon-ε gene. One method of designing a nonfunctional interferon-ε gene is to insert another gene, such as a selectable marker gene, within a nucleic acid molecule that encodes murine interferon-ε. Standard methods for producing these so-called "knockout mice" are known to those skilled in the art (see, for example, Jacob, "Expression and Knockout of Interferons in Transgenic Mice," in *Overexpression and Knockout of Cytokines in Transgenic Mice*, Jacob (ed.), pages 111–124 (Academic Press, Ltd. 1994), and Wu et al., "New Strategies for Gene Knockout," in *Methods in Gene Biotechnology*, pages 339–365 (CRC Press 1997)).

The present invention, thus generally described, will be understood more readily by reference to the following examples, which are provided by way of illustration and are not intended to be limiting of the present invention.

EXAMPLE 1

Construction of a Nucleic Acid Molecule Encoding Zifne

An expressed sequence tag was extended using 5' and 3' RACE. The 5' RACE was performed as follows: 2 µl of 1/100 diluted placenta marathon cDNA and 20 pmoles each of oligonucleotide primers ZC19,112 (TCTAG CTGTT GATGA AGTTG AATGA G; SEQ ID NO:12) and ZC9,739 (CCATC CTAAT ACGAC TCACT ATAGG GC; SEQ ID NO:13) were added to a reaction containing Advantage cDNA polymerase Mix (CLONTECH Laboratories, Inc.) following the manufacturer's (CLONTECH) recommended protocol for RACE amplifications. The reactions were run as follows: 94° C. for 30 seconds, 5 cycles of 94° C. for 5 seconds and 72° C. for 4 minutes, 5 cycles of 94° C. for 5 seconds and 70° C. for 4 minutes, and 20 cycles of 94° C. for 5 seconds and 68° C. for 4 minutes, followed by 68° C. for 10 minutes and a hold at 4° C. This first round amplification was diluted 1 to 50, and 5 µl were used in the second round, nested, and amplification was performed as above except using 20 pmoles each of oligonucleotide primers ZC19,112 and ZC9,719 (ACTCA CTATA GGGCT CGAGC GGC; SEQ ID NO:14). A 5' RACE product of 781 base pairs was sequenced.

The 3' RACE was performed as above except that the first round of amplification used oligonucleotides ZC19,111 (AGGGC AAATA TTTCT CTGGA TGG; SEQ ID NO:15) and ZC9,739 while the second round, or nested, amplification used oligonucleotides ZC19,111 and ZC9,719. A 3' RACE product of 451 base pairs was sequenced.

From a consensus sequence generated from the original expressed sequence tag sequence, the 5' RACE sequence and the 3' RACE sequence, oligonucleotide primers were designed to the 5' and 3' untranslated regions. These 5' and 3' untranslated region oligonucleotide primers were ZC19,536 (AGGGA TAAGT AGCAT ATTTG ACCT; SEQ ID NO:16) and ZC19,535 (TGTAC TATAA ATTGT ATTAC CACTC TATGA; SEQ ID NO:17), respectively. Oligonucleotide primers ZC19,536 and ZC19,535 were used to PCR amplify a full length zifnie cDNA coding region. The PCR amplification was performed as follows: 5 µl of 1/100 diluted human uterus marathon cDNA and 10 pmoles each of oligonucleotide primers ZC19,536 and ZC19,535 were added to a reaction containing Advantage cDNA polymerase Mix (CLONTECH) following the manufacturer's recommended protocol. The reaction was run as follows: 94° C. for 1 minute and 30 seconds, 35 cycles of 94° C. for 30 seconds, 50° C. for 1 minute, and 68° C. for 1 minute, followed by 68° C. for 7 minutes and a hold at 4° C. The 722 base pair PCR amplified fragment was gel purified and recovered using a QIAex II extraction kit (QIAGEN Inc.; Valencia, Calif.) following the manufacturer's protocol. The recovered DNA was cloned into Invitrogen's pCR2.1-TOPO cloning vector following the manufacturer's recommended protocol and competent TOP10 *E. coli* (Invitrogen) were transformed with the cloned DNA following the manufacturer's protocol. Analysis of a DNA sequence from one of the colonies containing the ziffie 722 base pair PCR amplified insert demonstrated the presence of a full length zifne cDNA encoding the amino acid sequence of SEQ ID NO:2.

EXAMPLE 2

Expression of the Human Interferon-ε Gene

Northern analyses were performed using Human Multiple Tissue Blots I, II, and III (CLONTECH Laboratories, Inc., Palo Alto, Calif.). Two probes were generated from gel purified PCR products. The first probe was made using ZC16810 (CTCTG CTTCC AGTCC CATGA G; SEQ ID NO:8) and ZC16811 (GGACA CACTC TGGCC ATTCT C; SEQ ID NO:9) as primers and HUVEC (human umbilical vein endothelial cell) marathon cDNA as template. The probe was a radioactively labeled using the Multiprime labeling kit from Amersham (Arlington Heights, Ill.) according to the manufacturer's protocol. The probe was purified using a NUCTRAP push column (STRATAGENE, La Jolla, Calif.). EXPRESSHYB (CLONTECH) solution was used for the prehybridization and hybridization solutions for the northern blots. Hybridization took place overnight at 65° C. Following hybridization, the blots were washed in 2×SSC, 0.1% SDS at room temperature, followed by a wash in 0.1×SSC and 0.1% SDS at 50° C. The results demonstrated expression of an interferon-ε band in trachea mRNA. A second probe was made using ZC18,425 (AAACT TTCTG CTTCC TCAGA; SEQ ID NO:10) and ZC18,424 (CCCAA AGTAC CACTT AGCTT; SEQ ID NO:11) as primers and HUVEC marathon cDNA as template. The northern was performed as described above, and demonstrated expression of an interferon-ε band in placental mRNA.

In another study, PCR of placenta marathon ready cDNA, using the ZC18,425 and ZC18,424 primer set, demonstrated the presence an interferon-ε specific band, which is consistent with the results of northern analysis. The presence of an interferon-ε specific band was also detected as a PCR product from uterus marathon cDNA. In these studies, CLONTECH's Advantage cDNA Polymerase Mix was used in a typical PCR reaction mix under the following conditions: 94° C. for 1 min 30 seconds, 35 cycles of 94° C. for 5 seconds, 56° C. for 30 seconds, 68° C. for 30 seconds, then 68° C. for 4 minutes, and a 4° C. hold.

EXAMPLE 3

Localization of the Human Interferon-ε Gene

The Ziftne gene was mapped to chromosome 9 using the commercially available version of the "Stanford G3 Radiation Hybrid Mapping Panel" (Research Genetics, Inc., Huntsville, Ala.). The "Stanford G3 RH Panel" contains DNA molecules from each of 83 radiation hybrid clones of the whole human genome, plus two control DNAs (the RM donor and the A3 recipient). A WWW server (http:H/shgc-www.stanford.edu) allows chromosomal localization of markers.

For the mapping of Zifne with the "Stanford G3 RH Panel," 20 µl reactions were set up in a 96-well microtiter plate (STRATAGENE, Inc.; La Jolla, Calif.) and used in a "RoboCycler Gradient 96"thermal cycler (STRATAGENE). Each of the 85 PCR reactions consisted of 2 µl 10× KlenTaq PCR reaction buffer (CLONTECH Laboratories, Inc.; Palo Alto, Calif.), 1.6 µl dNTPs mix (2.5 mM each, PERKIN-ELMER; Foster City, Calif.), 1 µl sense primer ZC20,023 (5' AGC CGA TGT CTG TTC TTT 3'; SEQ ID NO:18), 1 µl antisense primer ZC15,841 (5' CCT CGG GCT TCT AAA CTC 3'; SEQ ID NO:19), 2 µl "RediLoad" (Research Genetics, Inc.; Huntsville, Ala.), 0.4 µl 50× Advantage KlenTaq Polymerase Mix (CLONTECH Laboratories, Inc.), 25 ng of DNA from an individual hybrid clone or control and ddH$_2$O for a total volume of 20 µl. The reactions were overlaid with an equal amount of mineral oil and sealed. The PCR cycler conditions were as follows an initial 1 cycle 5 minute denaturation at 94° C., 35 cycles of a 45 second denaturation at 94° C., 45 second annealing at 58° C. and 1 minute extension at 72° C, followed by a final 1 cycle extension of 7 minutes at 72° C. The reactions were separated by electrophoresis on a 2% agarose gel (Life Technologies, Gaithersburg, Md.).

The results showed linkage of Zifne to the framework marker SHGC-10403 with a LOD score of >4 and at a distance of 45.837cR_10000 from the marker. The use of surrounding markers positions Zifne in the 9p22.2 region on the integrated LDB chromosome 9 map (The Genetic Location Database, University of Southhampton, WWW server:http://cedar.genetics.soton.ac.uk/public_html/).

EXAMPLE 4

Southern Analysis of the Human Interferon-ε Gene

Southern analysis was performed using a commercially prepared Interspecies Zoo-Blot from CLONTECH Laboratories, Inc. The Southern blot contained EcoRI-digested DNA. The hybridization probe was generated from a gel purified PCR amplification product. The probe was made using ZC19,536 (AGGGA TAAGT AGCAT ATTTG ACCT; SEQ ID NO:16) and ZC18,424 (CCCAA AGTAC CACTT AGCTT; SEQ ID NO:11) as primers and the cloned Zifnie cDNA as template. The probe was a radioactively labeled using the REDIPRIME II labeling kit (AMERSHAM PHARMACIA BIOTECH, Inc.; Piscataway, N.J.) according to the manufacturer's protocol. The probe was purified using a NUCTRAP push column (STRATAGENE, La Jolla, Calif.). EXPRESSHYB (CLONTECH) solution was used for the prehybridization and hybridization solutions for the Southern blots. Hybridization took place overnight at 65° C. Following hybridization, the blots were washed in 2×SSC, 0.1% SDS at room temperature, followed by a wash in 0.1×SSC and 0.1% SDS at 50° C. The blots were then exposed to Kodak BioMax film. The human and monkey samples showed a hybridizing fragment of approximately 6.6 kilobases. The mouse genomic DNA sample showed faintly hybridizing fragments at approximately 7.5 and 5.5 kilobases, while canine and bovine genomic DNA samples contained hybridizing fragments of about 5 and 3.5 kilobases.

EXAMPLE 5

Expression of the Interferon-ε Gene by Human Cells

Cultures of normal human primary cells (CLONETICS Corporation; Walkersville, Md.) were grown in the presence of IL-1β (10 ng/ml), TNF-α (10 ng/ml), or polyinosinic acid-polycytidylic acid (poly I:C; 100 μg/ml) (SIGMA; St. Louis, Mo.), or in medium alone. After about four hours of incubation, total RNA was isolated from cells, treated with RNase-free DNase, and used as a template for cDNA synthesis with Superscript Reverse Transcriptase (Life Technologies, Inc.; Rockville, Md.). Aliquots of cDNA were tested in separate PCR reactions with the following primer pairs specific for the interferon-ε gene: ZC21,078 (GCC TCT ACC ACT ATC TTC TC; SEQ ID NO:21) and ZC21,079 (GGT CTT CCT TGT TTG CTC AG; SEQ ID NO:22). Aliquots of cDNA were also tested with primer pairs specific for MHC Class I (CLONTECH) as a control.

Interferon-ε rRNA was detected in human umbilical vein endothelial cells (HUTVEC) after stimulation with either IL-β or TNF-α. Neonatal human dermal fibroblasts contained detectable levels of interferon-ε rnRNA after stimulation with poly I:C and IL-1β. Interferon-ε mRNA was also detected in human coronary artery smooth muscle cells, human microvascular endothelial cells, and normal human bronchial epithelial cells under all test conditions, including incubation in medium alone. Thus, the results show that interferon-ε mRNA is present in several distinct cell types: endothelial cells, smooth muscle cells, and epithelial cells. These cell types are derived from umbilical vein, neonatal dermis, coronary artery, and bronchial tubes. The results also indicate that interferon-ε mRNA synthesis is stimulated by interferon inducers such as IL-1β, poly I:C, and TNF-α.

EXAMPLE 6

Construction of a Nucleic Acid Molecule Encoding Murine Interferon-ε

A 417 base pair PCR product was obtained from primers ZC19,536 (SEQ ID NO:16) and ZC 18,424 (SEQ ID NO:11). This DNA probe, which represents the 5'-end of the Zifne gene, was radiolabeled with $^{32}$P using the REDIPRIME II labeling kit (AMERSHAM PHARMACIA BIOTECH, Inc.; Piscataway, N.J.) according to the manufacturer's protocol. The probe was purified using a NUCTRAP push column (STRATAGENE, La Jolla, Calif.).

A mouse genomic phage library (CLONETECH) was screened with the radiolabeled interferon-ε probe, and positive plaques were isolated, replated, and rescreened. DNA from individual phage plaques was then isolated and purified according to standard protocols. Mouse genomic DNA inserts were cleaved from phage DNA with SacI, fractionated by agarose gel electrophoresis and examined by Southern analysis with a human interferon-ε probe. Positive DNA bands were cut from gels and subcloned. Genomic DNA inserts were then isolated from the subdlones and sequenced.

EXAMPLE 7

Inhibition of the Proliferation of a Human Burkitt Lymphoma B Cell Line by Murine Interferon-ε

A liposome-mediated transfection procedure was used to introduce murine interferon-ε expression vectors into baby hamster kidney cells (BHK-570; ATCC CRL 10314). These vectors comprised a dihydrofolate reductase gene, and nucleotide sequences that encode either untagged murine interferon-ε having the amino acid sequence of SEQ ID NO:24 or murine interferon-ε with a C-terminal Glu-Glu tag. The interferon genes were operably linked with a cytomegalovirus promoter. Transfected cells were selected by incubation with methotrexate to 3 μM.

To prepare conditioned media samples, cells approaching confluent growth were incubated in base Dulbecco's Modified Eagle Medium (high glucose) containing L-glutamine, sodium pyruvate, and HEPES buffer. The cultures were incubated for 48 hours, and then conditioned medium samples were collected, filter-sterilized, and stored at 4° C. Millipore Ultrafree-15 Centrifugal Filter Devices (molecular weight cut-off of 5000) were used to concentrate conditioned medium samples. In brief, filter columns were centrifuged chilled at approximately 1300×G for 30 minutes to reduce the volume 50-fold, and 50× concentrated conditioned medium was then sterilized with a 0.2 μM filter and stored at 4° C. The 50× concentrated conditioned medium was diluted in standard Daudi medium (RPMI 1640 with 2mM L-glutamine, 0.075% NaHCO$_3$, 20mM HEPES buffer, 1 mM sodium pyruvate, 4.5g/L glucose) for cell proliferation studies.

The effect of murine interferon-ε on human B cell lymphoma cells was tested with a Daudi cell proliferation assay. Daudi cells were harvested and diluted to 100,000 cells/ml in standard Daudi medium with 10% fetal bovine serum. Conditioned medium samples were diluted in serum-free Daudi medium, and the samples were added in 100 μl aliquots to the wells of a 96-well flat bottom plate in triplicate. Each well then received 10,000 cells (100 μl), and the cells and test samples were mixed with a multi-channel pipette. After a three-day incubation at 37° C., 1 μCi of $^3$H-thymidine was added per well, and the cells were incubated for six hours at 37° C. Daudi cells were harvested onto a filter mat, washed 10 times, and dried for one hour at 37° C. About 25 μl of scintillation fluid were added to each sample, and the counts per minute for each mixture were measured with a scintillation counter.

Figure 2:
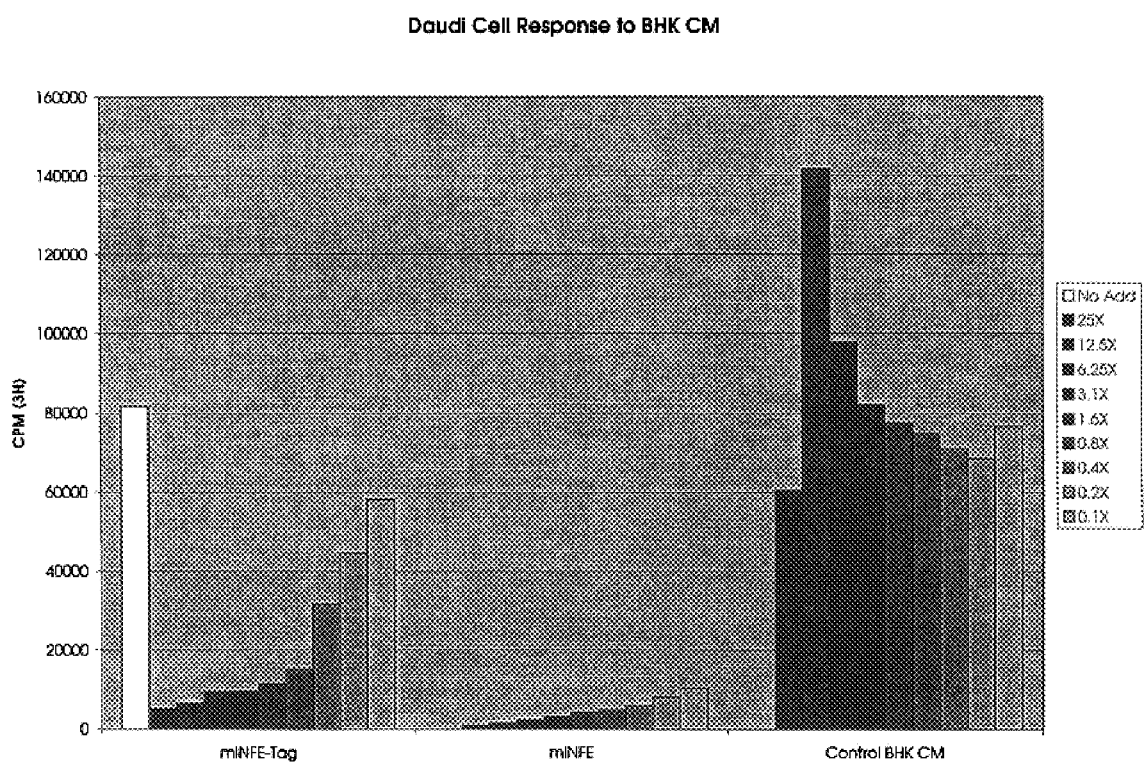
FIG. 2 shows the incorporation of tritiated thymidine by Daudi cells treated with various concentrations of conditioned media from recombinant baby hamster kidney (BHK) host cells that were transfected with an expression vector comprising a dihydrofolate reductase (DHFR) gene ("Control BHK CM"), a DHFR gene and a nucleotide sequence encoding murine interferon-ε ("mIFNE"), or a DHFR gene and a nucleotide sequence encoding murine interferon-ε with a Glu-Glu tag ("mIFNE-tag").

As shown in FIG. 2, the incorporation of tritiated thymidine was inhibited, in a dose-dependent manner, by treatment with conditioned medium from BHK cells transfected with either of the murine interferon-ε expression vectors. In contrast, Daudi cells showed an increase in tritiated thymidine incorporation when incubated with conditioned medium from BHK cells transfected with a dihydrofolate reductase expression vector that lacked a murine interferon-ε gene. These results show that murine interferon-ε inhibits the proliferation of human lymphoma cells, as indicated by a decrease in thymidine incorporation.

EXAMPLE 8

Anti-viral Activity of Murine Interferon-ε

The anti-viral activity of murine interferon-ε was examined using mouse fibroblast cells (L929) and human cervical carcinoma cells (HeLa). On the first day, 50,000 cells and various concentrations of conditioned medium samples were distributed per well of a multi-well plate. As described in Example 7, 50× concentrated conditioned medium was obtained from BHK-570 cells transfected with an expression vector that lacked a murine interferon-ε gene, an expression vector that included nucleotide sequence encoding untagged murine interferon-ε, or an expression vector that included a nucleotide sequence that encoded murine interferon-ε with a C-terminal Glu-Glu tag. Conditioned medium from control cells and from cells comprising the expression vector for untagged murine interferon-ε were tested with both L929 cells and HeLa cells, while conditioned medium from cells containing the expression vector for tagged murine interferon-ε was tested in L929 cells alone.

Following a 24 hour incubation at 37° C., the medium was removed, and replaced with medium containing encephalomyocarditis virus at a multiplicity of infection of 0.1. The cells were again incubated for 24 hours at 37° C. Culture wells were then scored visually for the presence of cytopathic effect, which was determined as shown in Table 7.

TABLE 7

| Designation | Observation of Cytopathic Effect (CPE) |
| --- | --- |
| − | no CPE |
| +/− | possible CPE (about 1% of monolayer surface) |
| + | CPE limited to one plaque (about 5% of the surface) |
| +1 | CPE limited to three plaques, affecting less than 25% of the monolayer |
| 1 | 25% CPE |
| 1–2 | 37% CPE |
| 2 | 50% CPE |
| 2–3 | 62% CPE |
| 3 | 75% CPE |
| 3–4 | 87% CPE |
| 4 | 100% CPE |

Figure 3:
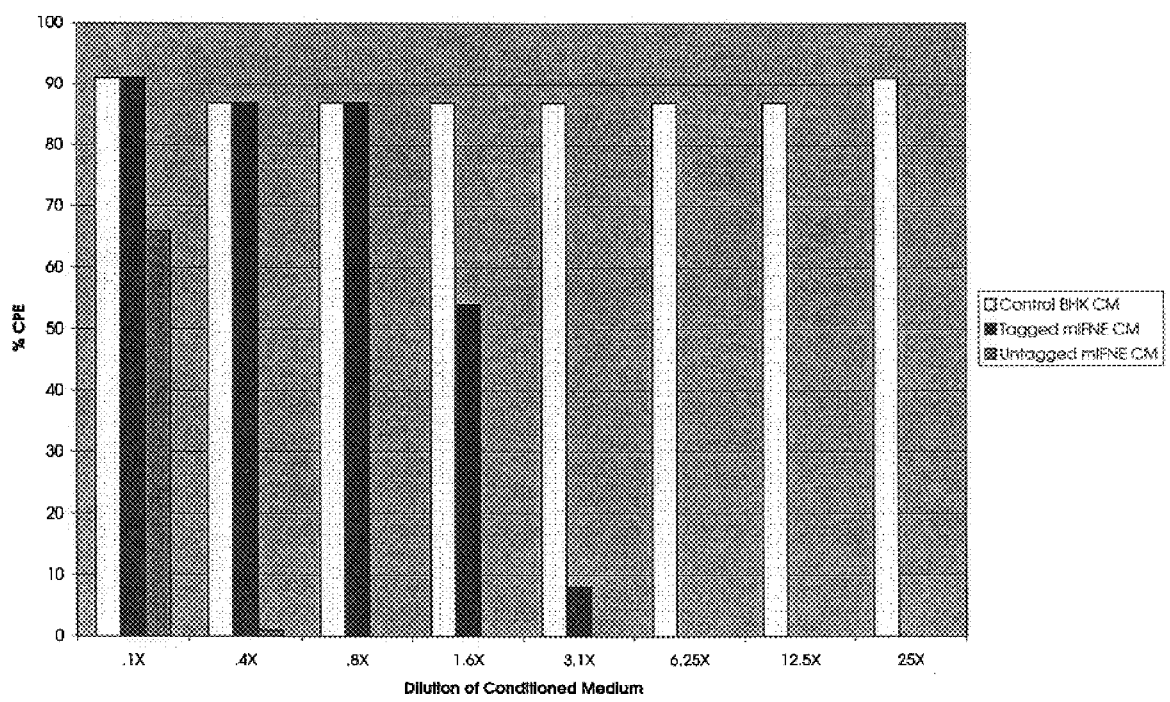
FIG. 3 shows the antiviral effect of murine interferon-ε on murine L929 cells infected with encephalomyocarditis virus. CPE: cytopathic effect; Control BHK CM: conditioned medium from recombinant baby hamster kidney (BHK) host cells transfected with an expression vector comprising a dihydrofolate reductase (DHFR) gene; Tagged mIFNE CM.

The results showed d that both conditioned medium from cells having either murine interferon-ε expression vector inhibited viral infection in L929 cell s in a dose-dependent manner, while conditioned medium from control BHK-570 cells failed to block the appearance of cytopathic effect See FIG. 3. As shown in FIG. 4, control medium did not inhibit viral infection in HeLa cells, whereas the appearance of cytopathic effect was inhibited in a dose-dependent manner when the cells were treated with conditioned medium from cells transfected with an expression vector for untagged murine interferon-ε.

EXAMPLE 9

Stimulation of Interferon-inducible Genes by Murine Interferon-ε

The ability of murine interferon-ε to stimulate the expression of known interferon-inducible genes was examined in murine and human cell lines. In these studies, the murine cells were provided by a wild-type murine BAF-3 cell line, which is an immortalized interleukin-3 dependent lymphoid cell line (see, for example, Rodriguez-Tarduchy et al., EMBO. J. 9:2997 (1990)). These cells were incubated in standard medium supplemented with murine interleukin-3 (2 ng/ml). About 24 hours before interferon treatment, the cells were incubated in standard medium without interleukin-3. A culture of human Daudi cells was prepared in standard medium.

Cells were treated for six hours with conditioned media (CM) or interferon-β as a control. Following this treatment, total RNA samples were collected from the cells using a standard technique, sample RNA was quantitated, and then treated with DNase. cDNA molecules encoding five interferon-inducible genes were synthesized with primers based upon known nucleotide sequences and SuperScript II RNase H-Reverse Transcriptase (Life Technologies, Inc; Rockville, Md.), using the manufacturer's suggested protocols. RT-PCR was then performed, and the products were analyzed by gel electrophoresis.

As shown in Table 8, murine interferon-ε stimulates the expression of phospholipid scramblase and 2–5A synthetase in both human and murine cell lines. Murine interferon-ε treatment also stimulates the expression of Interferon-stimulated Gene (ISG)-56k in the human cell line. These results show that murine interferon-ε can affect both murine and human cells. In contrast, neither the murine nor the human interferon-β appeared to be cross-species reactive in this study.

TABLE 8

| | Stimulation of Interferon-inducible Genes[2] | | | | |
| --- | --- | --- | --- | --- | --- |
| Treatment[1] | Human Scramblase | Murine Scramblase | Human 2-5A Synthetase | Murine 2-5A Synthetase | Human ISG-56k |
| Daudi Cells: | | | | | |
| m-interferon-β | − | N/A | − | N/A | + |
| h-interferon-β | +++ | N/A | +++ | N/A | +++ |
| Control CM | − | N/A | + | N/A | + |
| h-interferon-β | − | N/A | + | N/A | + |
| m-interferon-β | +++ | N/A | +++ | N/A | +++ |
| BAF-3 Cells: | | | | | |
| m-interferon-β | N/A[3] | +++ | N/A | +++ | N/A |
| h-interferon-β | N/A | + | N/A | + | N/A |
| Control CM | N/A | + | N/A | + | N/A |
| h-interferon-ε | N/A | + | N/A | + | N/A |
| m-interferon-ε | N/A | +++ | N/A | +++ | N/A |

[1]m-interferon-β: recombinant murine interferon-β (2.5 ng/ml; Research Diagnostics, Inc.; Flanders NJ); h-interteron-β: recombinant human interferon-β (2.5 ng/ml; Research Diagnostics, Inc.; Flanders NJ); control CM: conditioned medium at 0.125× (1:8 dilution) from BHK cells transfected with an expression vector that lacks an interferon gene; h-interferon-ε and m-interferon-ε: conditioned media at 0.125× (1:8 dilution) from BHK cells transfected with an expression vector comprising either a human interferon-ε gene or a murine interferon-ε gene.
[2]Illustrative references that describe interferon-inducibe genes include Zhou et al., J Biol. Chem. 272:18240 (1997) [human phospholipid scramblase]; Zhou et al., Biochemistry 37:2356 (1998) [murine phospholipid scramblase]; Wathelet et al., Eur. J. Biochem. 169:313 (1987) [human 2-5A synthetase]; Ghosh et al., J. Biol. Chem. 266:15293 (1991) [murine 2-5A synthetase]; and Wathelet et al., FEBS Lett. 231:164 (1988) [human ISG-56k].
[3]Not applicable.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

We claim:

1. An isolated nucleic molecule that encodes a polypeptide comprising amino acid residues 22 to 192 of SEQ ID NO:24.

2. The isolated nucleic acid molecule of claim 1, wherein the nucleic acid molecule comprises the nucleotide sequence of nucleotides 842 to 1354 of SEQ ID NO:23.

3. An expression vector, comprising a nucleic acid molecule encoding a polypeptide that comprises amino acid residues 22 to 192 of SEQ ID NO:24, a transcription promoter, and a transcription terminator, wherein the promoter is operably linked with the nucleic acid molecule, and wherein the nucleic acid molecule is operably linked with the transcription terminator.

4. A recombinant host cell comprising the expression vector of claim 3, wherein the host cell is selected from the group consisting of bacterium, yeast cell, fungal cell, insect cell, avian cell, mammalian cell, and plant cell.

5. The recombinant host cell of claim 4, wherein the host cell is a bacterium.

6. The recombinant host cell of claim 4, wherein the host cell is a yeast cell.

7. The recombinant host cell of claim 4, wherein the host cell is a fungal cell.

8. The recombinant host cell of claim 4, wherein the host cell is a insect cell.

9. The recombinant host cell of claim 4, wherein the host cell is a avian cell.

10. The recombinant host cell of claim 4, wherein the host cell is a mammalian cell.

11. The recombinant host cell of claim 4, wherein the host cell is a plant cell.

12. A method of producing a polypeptide that comprises amino acid residues 22 to 192 of SEQ ID NO:24, comprising culturing recombinant host cells that comprise the expression vector of claim 3, and that produce the polypeptide.

13. The method of claim 12, further comprising isolating the polypeptide from the cultured recombinant host cells.

14. A recombinant virus, comprising the expression vector of claim 3.

15. A composition, comprising a carrier and at least one of the expression vector of claim 3 or a recombinant virus that comprises the expression vector of claim 3.

16. The composition of claim 15, wherein the carrier is a pharmaceutically acceptable carrier.

17. The isolated nucleic acid molecule of claim 1, wherein the nucleic acid molecule encodes a polypeptide having an amino acid sequence consisting of amino acid residues 22 to 192 of SEQ ID NO:24.

18. The isolated nucleic acid molecule of claim 1, wherein the nucleic acid molecule encodes a polypeptide comprising amino acid residues 1 to 192 of SEQ ID NO:24.

19. The isolated nucleic acid molecule of claim 18, wherein the nucleic acid molecule encodes a polypeptide having an amino acid sequence consisting of amino acid residues 1 to 192 of SEQ ID NO:24.

20. The isolated nucleic acid molecule of claim 18, wherein the nucleic acid molecule comprises the nucleotide sequence of nucleotides 779 to 1354 of SEQ ID NO:23.

21. A vector, comprising the nucleic acid molecule of claim 1.

22. A vector, comprising the nucleic acid molecule of claim 18.

* * * * *